United States Patent
Okano et al.

(10) Patent No.: US 8,454,968 B2
(45) Date of Patent: Jun. 4, 2013

(54) METHOD FOR INDUCING IMMUNITY WITH A PEPTIDE FRAGMENT FROM HUMAN CAPRIN-1

(75) Inventors: Fumiyoshi Okano, Kanagawa (JP); Masaki Shimizu, Ehime (JP); Takanori Saito, Kanagawa (JP)

(73) Assignee: Toray Industries, Inc., Tokyo (JP)

( * ) Notice: Subject to any disclaimer, the term of this patent is extended or adjusted under 35 U.S.C. 154(b) by 14 days.

(21) Appl. No.: 13/056,122

(22) PCT Filed: Aug. 5, 2009

(86) PCT No.: PCT/JP2009/063881
§ 371 (c)(1),
(2), (4) Date: Jan. 27, 2011

(87) PCT Pub. No.: WO2010/016525
PCT Pub. Date: Feb. 11, 2010

(65) Prior Publication Data
US 2011/0123492 A1      May 26, 2011

(30) Foreign Application Priority Data

Aug. 5, 2008 (JP) ................................. 2008-202065

(51) Int. Cl.
*A61K 39/00* (2006.01)
*A61K 38/00* (2006.01)
*A61K 38/04* (2006.01)
*C12N 15/00* (2006.01)

(52) U.S. Cl.
USPC ......... 424/185.1; 514/1.1; 514/19.4; 530/328

(58) Field of Classification Search
None
See application file for complete search history.

(56) References Cited

U.S. PATENT DOCUMENTS

| | | | |
|---|---|---|---|
| 8,008,431 B2 * | 8/2011 | Weinschenk et al. | 530/300 |
| 2003/0190640 A1 | 10/2003 | Faris et al. | |
| 2005/0003390 A1 | 1/2005 | Axenovich et al. | |
| 2008/0075722 A1 | 3/2008 | DePinho et al. | |
| 2008/0107668 A1 * | 5/2008 | Philip et al. | 424/185.1 |
| 2010/0029573 A1 | 2/2010 | Weinschenk et al. | |

FOREIGN PATENT DOCUMENTS

| | | |
|---|---|---|
| CN | 1678338 A | 10/2005 |
| EP | 1557172 A1 | 5/2007 |
| WO | WO 02/083070 A2 | 10/2002 |
| WO | WO 2005/100998 A2 | 10/2005 |
| WO | WO-2005/116051 A2 | 12/2005 |
| WO | WO-2008/088583 A2 | 7/2008 |

OTHER PUBLICATIONS

Ellis et al., "Identification and Characterization of a Novel Protein (p137) Which Transcytoses Bidirectionally in Caco-2 Cells", The Journal of Biological Chemistry, vol. 270, No. 35, 1995, pp. 20717-20723.
Grill et al., "Activation/Division of Lymphocytes Results in Increased Levels of Cytoplasmic Activation/Proliferation-Associated Protein-1: Prototype of a New Family of Proteins", The Journal of Immunology, 172, 2004, pp. 2389-2400.
International Search Report, dated Oct. 6, 2009 issued in PCT/JP2009/063881.
Wang et al., "Absence of Caprin-1 Results in Defects in Cellular Proliferation", The Journal of Immunology, vol. 175, No. 7, 2005, pp. 4274-4282, ISSN: 0022-1767.
Extended European Search Report issued in corresponding application No. EP 09805008.1 on Apr. 19, 2012.
Rauch, J. and Gires, O. "SEREX, Proteomex, AMIDA, and beyond: Serological screening technologies for target identification," Proteomics Clin. Appl., vol. 2, No. 3, pp. 355-371, 2008.
Office Action issued on Aug. 31, 2012 in corresponding Chinese Application No. 200980130313.6.

* cited by examiner

*Primary Examiner* — Elly-Gerald Stoica
(74) *Attorney, Agent, or Firm* — Birch, Stewart, Kolasch & Birch, LLP

(57) ABSTRACT

The invention relates to an immunity-inducing agent comprising, as an active ingredient, at least one polypeptide having immunity-inducing activity that is selected from among polypeptides (a), (b), and (c): (a) a polypeptide of at least seven contiguous amino acids of the amino acid sequence shown by any even SEQ ID number selected from SEQ ID NOs: 2 to 30 listed in the Sequence Listing; (b) a polypeptide of at least seven amino acids having 90% or more sequence identity with the polypeptide (a); and (c) a polypeptide comprising the polypeptide (a) or (b) as a partial sequence thereof, or a recombinant vector comprising a polynucleotide encoding said polypeptide and capable of expressing said polypeptide in vivo.

8 Claims, 5 Drawing Sheets

US 8,454,968 B2

METHOD FOR INDUCING IMMUNITY WITH A PEPTIDE FRAGMENT FROM HUMAN CAPRIN-1

TECHNICAL FIELD

The present invention relates to a novel immunity-inducing agent that is useful as a therapeutic and/or preventive agent for cancer or the like.

BACKGROUND ART

Cancer is the overall leading cause of death. At present, the primary form of cancer treatment technique is surgical treatment, which is carried out in combination with radiation treatment and chemotherapy. In spite of the development of novel surgical techniques and the discovery of novel anticancer agents of recent years, outcomes from cancer treatment still remain unimproved, except in the cases of some types of cancer. In recent years, cancer antigens recognized by cytotoxic T cells that are reactive to cancer and genes encoding cancer antigens have been identified along with the development of molecular biology and cancer immunology, and expectations for antigen-specific immunotherapy have increased (Tsuyoshi Akiyoshi, Gan to Kagaku Ryouhou (Cancer and Chemotherapy), 1997, vol. 24, pp. 551-519, Cancer and Chemotherapy Publishers Inc., Japan).

Immunotherapy requires the cancer-cell-specific presence of a peptide, polypeptide, or protein that is recognized as a target antigen, as well as substantial absence thereof in normal cells from the viewpoint of alleviation of side effects. In 1991, Boon et al. (the Ludwig Institute for Cancer Research, Belgium) isolated the human melanoma antigen MAGE1 recognized by the CD8+ T cell via cDNA expression cloning using an autologous cancer cell line and cancer-reactive T cells (Bruggen P. et al., Science, 254: 1643-1647, 1991). Thereafter, the SEREX (serological identifications of antigens by recombinant expression cloning) method, which identifies the tumor antigen recognized by the antibody produced in response to autologous cancer in the body of a cancer patient via gene expression cloning was reported (Proc. Natl. Acad. Sci. U.S.A., 92: 11810-11813, 1995; and U.S. Pat. No. 5,698,396). Some cancer antigens have been isolated by such techniques (Int. J. Cancer, 72: 965-971, 1997; Cancer Res., 58: 1034-1041, 1998; Int. J. Cancer, 29: 652-658, 1998; Int. J. Oncol., 14: 703-708, 1999; Cancer Res., 56: 4766-4772, 1996; and Hum. Mol. Genet. 6: 33-39, 1997). In addition, clinical testing of cancer immunotherapy targeting some such antigitens has been initiated.

As in the case of humans, dogs and cats are known to suffer from a variety of tumors, such as mammary gland cancer, leukemia, and lymphoma, and tumors are highly ranked in statistics for canine or feline diseases. However, there are no effective therapeutic, preventive, or diagnostic agents for canine or feline cancer at present. Most dog or cat owners would not notice canine or feline tumors until tumors become advanced and enlarged. Even if tumors are removed via surgical operation or drugs for human use (e.g., anticancer drugs) are administered, tumors are often already beyond cure, and animals often die shortly after treatment. Under such circumstances, if therapeutic, preventive, and diagnostic agents for cancer that are effective for dogs or cats become available, application thereof for canine or feline cancer can be expected.

The cytoplasmic and proliferation-associated protein 1 (CAPRIN-1) is expressed when dormant normal cells are activated or undergo cell division. CAPRIN-1 is an intracellular protein that is known to form intracellular stress granules with RNA in the cell and to be associated with regulation of mRNA transportation and translation. CAPRIN-1 is also known by various other names, and examples thereof include the GPI-anchored membrane protein 1 and the membrane component surface marker 1 protein (M11S1). CAPRIN-1 has names that convey the impression that it has been known as a cell membrane protein. Such other names derive from a report to the effect that the CAPRIN-1 gene sequence has a GPI-binding region and it is a membrane protein expressed in a large-intestine-derived cell line (J. Biol. Chem., 270: 20717-20723, 1995). Later, however, it was known that the CAPRIN-1 gene sequence in this report was incorrect, and in the gene sequence, deletion of a single nucleotide from the CAPRIN-1 gene sequence currently registered in the GenBank or the like causes a frame shift, thereby leading to deletion of 80 amino acids from the C terminus, and therefore the resulting artifact (74 amino acids) was the GPI-binding region mentioned in the foregoing report. In addition, it was also known that the CAPRIN-1 gene sequence shown in the report also had an error at the 5' side, and 53 amino acid residues had been deleted from the N-terminus (J. Immunol., 172: 2389-2400, 2004). It has also been reported that the protein encoded by the CAPRIN-1 gene sequence currently registered in GenBank or the like is not a cell membrane protein (J. Immunol., 172: 2389-2400, 2004).

Based on the report of J. Biol. Chem., 270: 20717-20723, 1995, that CAPRIN-1 is a cell membrane protein, US 2008/0075722 and WO 2005/100998 describe that CAPRIN-1 can be a target of cancer therapy as a cell membrane protein under the name of M11S1. However, they do not include any specific descriptions in the Examples. As reported in J. Immunol., 172: 2389-2400, 2004, however, it has been heretofore accepted since US 2008/0075722 was filed that CAPRIN-1 is not expressed on a cell surface. It is apparent that the disclosures of US 2008/0075722 and WO 2005/100998 based only on the incorrect information that CAPRIN-1 is a cell membrane protein should not be understood as general technical knowledge in the art. In addition, there is no report that the expression level of CAPRIN-1 is higher in cancer cells such as breast cancer cells than in normal cells.

SUMMARY OF THE INVENTION

Problem to be Solved by the Invention

It is an object of the present invention to discover a novel polypeptide useful for a therapeutic and/or preventive agent for cancer and to provide use of such polypeptide as an immunity-inducing agent.

Means for Solving the Problem

The present inventors have conducted concentrated studies, and then they obtained cDNAs encoding proteins that bind to antibodies in the serum obtained from a cancer-bearing living body by the SEREX method using a canine-testicular-tissue-derived cDNA library and the serum of a dog afflicted with breast cancer, and they prepared a canine CAPRIN-1 polypeptide having the amino acid sequences shown by SEQ ID NOs: 6, 8, 10, 12, and 14 using such cDNAs. Using the human homologous gene of the obtained gene, also, they prepared a human CAPRIN-1 polypeptide having the amino acid sequences as shown by SEQ ID NOs: 2 and 4. Further, they found that such CAPRIN-1 polypeptides were expressed specifically in a breast cancer, brain tumor, leukemia, lymphoma, lung cancer, esophagus cancer, and colorectal cancer. Furthermore, they found that administration of such CAPRIN-1 polypeptides to living bodies would lead to induction of immunocytes against CAPRIN-1 polypeptides in the living bodies and regression of tumors in living bodies expressing the CAPRIN-1 genes. In addition, they found that the antibodies against such CAPRIN-1 polypeptides would disrupt cancer cells that express the CAPRIN-1 genes and induce antitumor effects in vivo. This has led to the completion of the present invention.

Accordingly, the present invention has the following features.

(1) An immunity-inducing agent comprising, as an active ingredient, at least one polypeptide having immunity-inducing activity and selected from the following polypeptides (a), (b), and (c), or a recombinant vector comprising a polynucleotide encoding such polypeptide and capable of expressing such polypeptide in vivo:

(a) a polypeptide of at least seven contiguous amino acids of the amino acid sequence shown by any even SEQ ID number selected from SEQ ID NOs: 2 to 30 listed in the Sequence Listing;

(b) a polypeptide of at least seven amino acids having 90% or more sequence identity with the polypeptide (a); and (c) a polypeptide comprising the polypeptide (a) or (b) as a partial sequence thereof.

(2) The immunity-inducing agent according to (1), wherein the polypeptide (b) is a polypeptide having 95% or more sequence identity with the polypeptide (a).

(3) The immunity-inducing agent according to (1), wherein the polypeptide having immunity-inducing activity is a polypeptide of at least seven contiguous amino acids of the amino acid sequence shown by any even SEQ ID number selected from SEQ ID NOs: 2 to 30 listed in the Sequence Listing or a polypeptide comprising such polypeptide as a partial sequence thereof.

(4) The immunity-inducing agent according to (3), wherein the polypeptide having immunity-inducing activity is a polypeptide comprising the amino acid sequence shown by any even SEQ ID number selected from SEQ ID NOs: 2 to 30 listed in the Sequence Listing.

(5) The immunity-inducing agent according to (3), wherein the polypeptide having immunity-inducing activity is a polypeptide of at least seven contiguous amino acids in the region of amino acid residues (aa) 41 to 400 or amino acid residues (aa) 503 to 564 of the amino acid sequence shown by any even SEQ ID number selected from SEQ ID NOs: 2 to 30 listed in the Sequence Listing except for SEQ ID NO: 6 and SEQ ID NO: 18 or a polypeptide comprising such polypeptide as a partial sequence thereof.

(6) The immunity-inducing agent according to (5), wherein the polypeptide having immunity-inducing activity is a polypeptide of the amino acid sequence shown by any of SEQ ID NOs: 43 to 76 in the Sequence Listing or a polypeptide of 8 to 12 amino acids comprising the amino acid sequence shown by any of SEQ ID NOs: 43 to 76 in the Sequence Listing as a partial sequence thereof.

(7) The immunity-inducing agent according to any of (1) to (6), which comprises, as an active ingredient, one or plural types of such polypeptides.

(8) The immunity-inducing agent according to (7), wherein the polypeptide is an agent for treating an antigen-presenting cell.

(9) The immunity-inducing agent according to any of (1) to (7), which is for use in the treatment or prevention of animal cancer.

(10) The immunity-inducing agent according to (9), wherein the cancer is breast cancer, brain tumor, leukemia, lymphoma, lung cancer, esophagus cancer, or colorectal cancer.

(11) The immunity-inducing agent according to (9), wherein the animal is a human, dog, or cat.

(12) The immunity-inducing agent according to any of (1) to (11), which further comprises an immunopotentiating agent.

(13) The immunity-inducing agent according to (12), wherein the immunopotentiating agent is at least one adjuvant or cytokine selected from the group consisting of Freund's incomplete adjuvant, Montanide, poly IC and a derivative thereof, CpG oligonucleotide, interleukin 12, interleukin 18, interferon α, interferon β, interferon ω, interferon γ, and Flt3 ligand.

(14) An isolated antigen-presenting cell comprising a complex of the above-mentioned polypeptide having immunity-inducing activity and an HLA molecule.

(15) An isolated T cell, which selectively binds to a complex of the above-mentioned polypeptide having immunity-inducing activity and an HLA molecule.

(16) A method for inducing immunity comprising administering to an individual at least one polypeptide having immunity-inducing activity and selected from the following polypeptides (a) to (c), or a recombinant vector comprising a polynucleotide encoding such polypeptide and capable of expressing such polypeptide in vivo:

(a) a polypeptide of at least seven contiguous amino acids of the amino acid sequence shown by any even SEQ ID number selected from SEQ ID NOs: 2 to 30 listed in the Sequence Listing;

(b) a polypeptide of at least seven amino acids having 90% or more sequence identity with the polypeptide (a); and (c) a polypeptide comprising the polypeptide (a) or (b) as a partial sequence thereof.

EFFECTS OF THE INVENTION

The present invention provides a novel immunity-inducing agent useful for treatment and/or prevention of cancer. As specifically described in the examples below, administration of the polypeptide used in the present invention to a cancer-bearing animal enables induction of an immunocyte in the body of such cancer-bearing animal, which further enables shrinkage or regression of existing cancer.

EMBODIMENTS FOR CARRYING OUT THE INVENTION

<Polypeptides>

Figure 1:
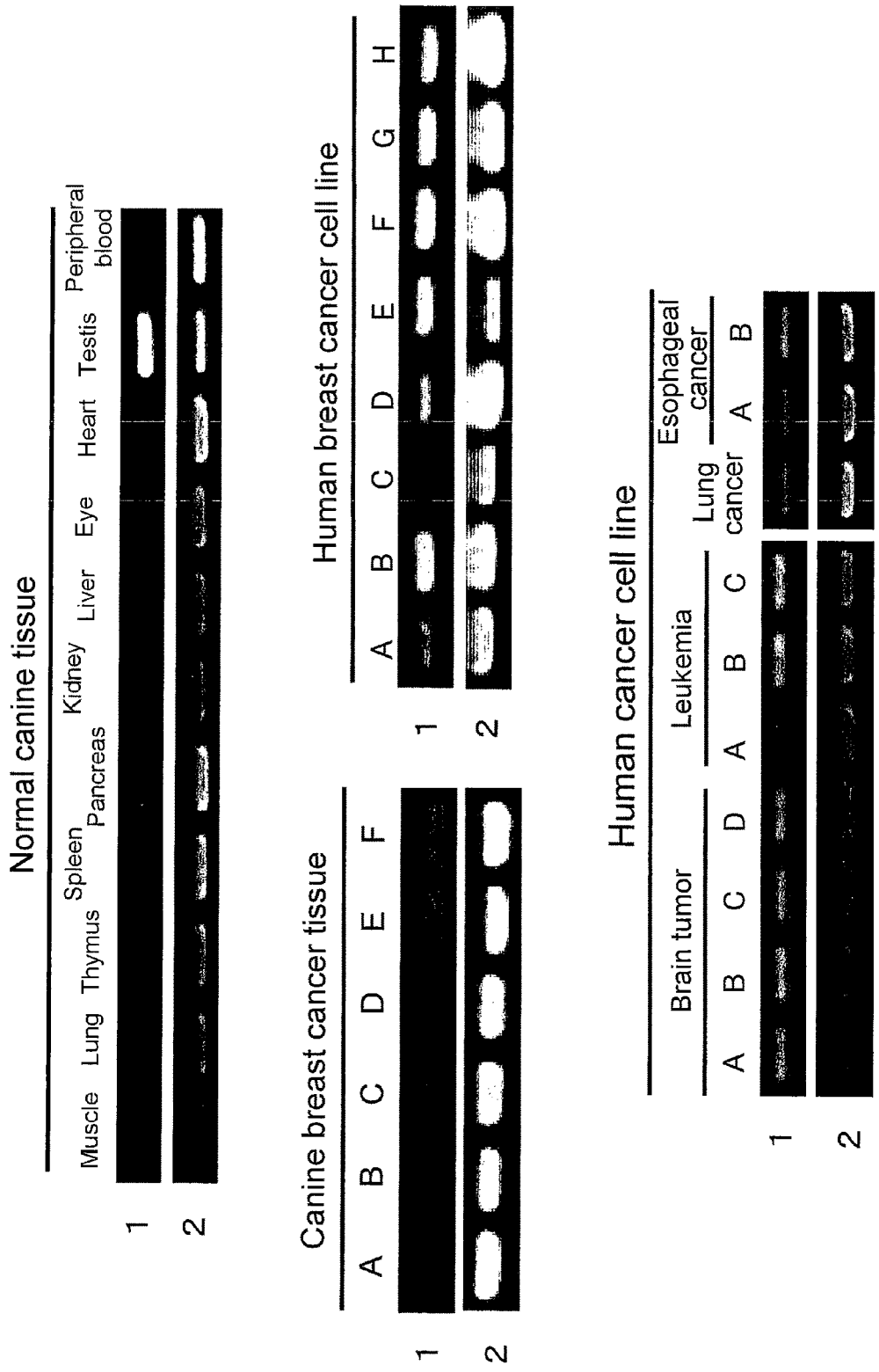
FIG. 1 shows the expression pattern of the gene encoding the CAPRIN-1 polypeptide in normal tissue and a tumor cell line. Reference number 1 represents the expression pattern of the gene encoding the CAPRIN-1 protein, and Reference number 2 represents the expression pattern of the GAPDH gene.

The polypeptides contained in the immunity-inducing agent of the present invention as an active ingredient include one or a plurality of polypeptides selected from the following polypeptides (a), (b), and (c):

(a) a polypeptide of at least seven contiguous amino acids in a polypeptide having the amino acid sequence shown by any even SEQ ID number selected from SEQ ID NOs: 2 to 30 listed in the Sequence Listing and having immunity-inducing activity;

(b) a polypeptide having 90% or more sequence identity with the polypeptide (a), consisting of at least 7 amino acids, and having immunity-inducing activity; and (c) a polypeptide comprising the polypeptide (a) or (b) as a partial sequence and having immunity-inducing activity.

The term "polypeptide" used herein refers to a molecule formed via peptide bonds among a plurality of amino acids. The term refers not only to a polypeptide molecule constituted by a large number of amino acids but also a low-molecular-weight molecule constituted by a small number of amino acids (an oligopeptide) and a full-length protein. In the present invention, the term "polypeptide" also refers to a protein of a full length sequence shown by any even SEQ ID number among SEQ ID NOs: 2 to 30.

The nucleotide sequences of polynucleotides encoding separate proteins consisting of the amino acid sequences as shown by even SEQ ID numbers among SEQ ID NOs: 2 to 30 (i.e., SEQ ID NOs: 2, 4, 6 . . . 28, and 30) are shown by odd SEQ ID numbers among SEQ ID NOs: 1 to 29 (i.e., SEQ ID NOs: 1, 3, 5 . . . 27, and 29).

The term "having the amino acid sequence" used herein refers to a sequence composed of amino acid residues in a particular order. For example, the term "a polypeptide having the amino acid sequence shown by SEQ ID NO: 2" refers to a polypeptide of 709 amino acid residues in length possessing the amino acid sequence shown by SEQ ID NO: 2, i.e., Met Pro Ser Ala Thr . . . (snip) . . . Gln Gln Val Asn. The term "a polypeptide having the amino acid sequence shown by SEQ ID NO: 2" may be occasionally abbreviated as "the polypeptide of SEQ ID NO: 2." The same applies to the expression "having the nucleotide sequence." In the context of that, the term "having" is interchangeable with the expression "consisting of:"

The term "immunity-inducing activity" used herein refers to the capacity for inducing an immunocyte that secretes cytokine, such as interferon or interleukin, in vivo.

Whether or not a polypeptide has immunity-inducing activity can be confirmed via, for example, known ELISPOT assay. Specifically, cells such as peripheral blood mononuclear cells are obtained from a living body to which a polypeptide to be assayed for the immunity-inducing activity has been administered, such cells are co-cultured in the presence of such polypeptide, and the production amount of cytokine and/or chemokine, such as IFN-γ or interleukin (IL), from the cells is measured with the use of a specific antibody, as described in the Examples below, for example. Thus, the number of immunocytes among the cells can be assayed. This enables evaluation of immunity-inducing activity.

Alternatively, a recombinant polypeptide prepared based on an amino acid sequence shown by any even SEQ ID number among SEQ ID NOs: 2 to 30 may be administered to a cancer-bearing animal, so that a tumor can be regressed by the immunity-inducing activity, as described in the Examples below. Thus, the immunity-inducing activity can be evaluated as the capacity for suppressing the growth of cancer cells expressing a polypeptide shown by any even SEQ ID number among SEQ ID NOs: 2 to 30 or the capacity for shrinking or eliminating cancer tissue (tumor) (hereafter, such capacity is referred to as "antitumor activity"). The antitumor activity of the polypeptides can be determined by, for example, actually administering such polypeptide to a cancer-bearing living body and examining whether or not the tumor is shrinked, as specifically described in the Examples below.

Alternatively, whether or not T cells stimulated by the polypeptide (i.e., T cells brought into contact with the antigen-presenting cells that present such polypeptide) exhibit cytotoxic activity on tumor cells in vitro may be examined to evaluate the antitumor activity of the polypeptide. T cells can be brought into contact with antigen-presenting cells via co-culture thereof in a liquid medium as described below. The cytotoxic activity can be assayed via a known technique referred to as the $^{51}$Cr-release assay technique described in, for example, Int. J. Cancer, 58: p. 317, 1994. When the polypeptides are used for treatment and/or prevention of cancer, it is preferable that the immunity-inducing activity be evaluated using the antitumor activity as an indicator, although a method of evaluation is not particularly limited.

The amino acid sequences shown by even SEQ ID numbers among SEQ ID NOs: 2 to 30 listed in the Sequence Listing disclosed by the present invention are the amino acid sequences of the CAPRIN-1 polypeptides isolated as the polypeptides binding to the antibodies existing specifically in the serum obtained from cancer-bearing dog and human, bovine, horse, mouse, and chicken homologues of such polypeptides by the SEREX method using the normal canine testicular tissue-derived cDNA library and the serum of a dog afflicted with breast cancer (see Example 1 below).

The polypeptide (a) indicated above is of at least 7 and preferably at least 8, 9, 10 or more contiguous amino acids in a polypeptide having an amino acid sequence shown by any even SEQ ID number among SEQ ID NOs: 2 to 30 and has immunity-inducing activity. Particularly preferably, such polypeptide has an amino acid sequence shown by any even SEQ ID number among SEQ ID NOs: 2 to 30. As known in the art, a polypeptide of at least about 7 amino acid residues can exert antigenicity. Accordingly, a polypeptide of at least seven contiguous amino acid residues of the amino acid sequence shown by any even SEQ ID number among SEQ ID NOs: 2 to 30 can exert antigenicity and immunogenicity. That is, a polypeptide of at least seven contiguous amino acid residues of the amino acid sequence shown by any even SEQ ID number among SEQ ID NOs: 2 to 30 can have immunity-inducing activity, and such polypeptide can be used for preparing the immunity-inducing agent of the present invention. Based on the fact that antibodies produced against an antigenic substance in vivo are polyclonal antibodies, a polypeptide composed of a larger number of amino acid residues can induce a larger variety of antibodies recognizing various sites of the antigenic substance, thereby enhancing the immunity-inducing activity. In order to enhance immunity-inducing activity, accordingly, the number of amino acid residues may be preferably at least 30 or more, or 50 or more, more preferably at least 100 or more, 150 or more, and further preferably at least 200 or more, or still preferably 250 or more.

As the principle of immunity induction via administration of a cancer antigen polypeptide, it is known that a polypeptide is incorporated into an antigen-presenting cell, the polypeptide is degraded by a peptidase in the cell into a smaller fragment (hereafter it may be referred to as an "epitope"), such fragment is presented on the cell surface, cytotoxic T cells or the like recognize such fragment and selectively kill the antigen-presenting cells. The size of a polypeptide presented on the antigen-presenting cell surface is relatively small, and it is about 7 to 30 in terms of the number of amino acids. From the viewpoint of presentation on the antigen-presenting cell, accordingly, it is sufficient that the polypeptide (a) is of about 7 to 30 and preferably about 8 to 30 or 9 to 30 contiguous amino acids in the amino acid sequences shown by any even SEQ ID number among SEQ ID NOs: 2 to 30. Such polypeptide of a relatively small size may be directly presented on the antigen-presenting cell surface without being incorporated into the antigen-presenting cell.

The polypeptide incorporated into the antigen-presenting cell is cleaved at random positions with a peptidase present in the cells, a variety of polypeptide fragments are generated, and such polypeptide fragments are presented on the antigen-presenting cell surface. If a large polypeptide such as a full-length sequence shown by any even SEQ ID number among SEQ ID NOs: 2 to 30 is administered, accordingly, polypeptide fragments that are effective for immunity induction mediated by antigen-presenting cells via degradation in the antigen-presenting cell are naturally generated. Thus, a large-size polypeptide can be preferably used for immunity induction mediated by antigen-presenting cells, and the number of amino acids may be at least 30, more preferably at least 100, further preferably at least 200, and still further preferably at least 250.

Further, the polypeptide of the present invention can be screened for a peptide being a possible epitope with the use of a matching medium that can search for a peptide serving as a possible epitope having a binding motif for each HLA type, such as the HLA Peptide Binding Predictions of Bioinformatics & Molecular Analysis Selection (BIMAS) (http://bimas.dcrt.nih.gov/molbio/hlabind/index.html). Specifically, a polypeptide of at least seven contiguous amino acids in the region of amino acid residues (aa) 41 to 400 or amino acid residues (aa) 503 to 564 in the amino acid sequences shown by any even SEQ ID number selected from among SEQ ID NOs: 2 to 30 except for SEQ ID NO: 6 and SEQ ID NO: 18 or a polypeptide comprising such polypeptide as a partial sequence thereof is preferable. In the polypeptide of SEQ ID NO: 2, a polypeptide shown by any of SEQ ID NOs: 43 to 76 is more preferable.

The polypeptide (b) above is derived from the polypeptide (a) by substitution, deletion, addition, and/or insertion of a small number of (preferably one or several) amino acid residues, it has 80% or more, 85% or more, preferably 90% or more, more preferably 95% or more, further preferably 98% or more, 99% or more, or 99.5% or more sequence identity with the original sequence, and it has immunity-inducing activity. When a small number of (preferably one or several) amino acid residues are substituted with, deleted from, added to, or inserted into the amino acid sequence of the protein antigen, in general, it is extensively known in the art that the resulting protein occasionally has substantially the same antigenicity or immunogenicity with that of the original protein. Thus, the polypeptide (b) above is capable of exerting the immunity-inducing activity and it can be thus used for preparing the immunity-inducing agent of the present invention. Alternatively, the polypeptide (b) above is preferably a polypeptide having an amino acid sequence derived from the amino acid sequence shown by any even SEQ ID number among SEQ ID NOs: 2 to 30 by substitution, deletion, addition, and/or insertion of one or several amino acid residues. The term "several" used herein refers to an integer from 2 to 10, preferably an integer from 2 to 6, and further preferably an integer from 2 to 4.

The term "sequence identity" used herein regarding the amino acid sequence or nucleotide sequence represents a percentage (%) determined by aligning two amino acid sequences (or nucleotide sequences) to be compared so as to maximize the number of matching amino acid residues (or nucleotides) and dividing the number of matched amino acid residues (or the number of matched nucleotides) by the total number of amino acid residues (or the total number of nucleotides). When aligning the sequences as described above, a gap is adequately inserted into one or both of the two sequences to be compared, according to need. Such sequence alignment can be carried out with the use of a well-known program, for example, BLAST, FASTA, or CLUSTAL W (Karlin and Altschul, Proc. Natl. Acad. Sci. U.S.A., 87: 2264-2268, 1993; Altschul et al., Nucleic Acids Res., 25: 3389-3402, 1997). When a gap is inserted, the total number of amino acid residues (or the total number of nucleotides) is the number of residues (or the number of nucleotides) counted by designating a gap as an amino acid residue (or a nucleotide). When the total number of amino acid residues (or the total number of nucleotides) thus determined differs between the two sequences to be compared, identity (%) is determined by dividing the number of the matched amino acid residues (or the number of nucleotides) by the total number of amino acid residues (or the total number of nucleotides) of a longer sequence.

A preferable amino acid substitution is a conservative amino acid substitution. Twenty types of amino acids constituting a naturally-occurring protein can be classified into groups of amino acids having similar properties: i.e., neutral amino acids having low-polarity side chains (Gly, Ile, Val, Leu, Ala, Met, and Pro); neutral amino acids having hydrophilic side chains (Asn, Gln, Thr, Ser, Tyr, and Cys); acidic amino acids (Asp, and Glu); basic amino acids (Arg, Lys, and His); and aromatic amino acids (Phe, Tyr, Trp, and His). It is known that substitution within such groups; i.e., conservative substitution, would not alter polypeptide properties in many cases. When amino acid residues in the polypeptide (a) of the present invention are substituted, accordingly, substitution may be carried out within such groups, so that a possibility of maintaining the immunity-inducing activity can be enhanced. In the present invention, however, the altered polypeptide may have non-conservative substitution, provided that the resulting polypeptide has immunity-inducing activity equivalent or substantially equivalent to that of an unaltered polypeptide.

The polypeptide (c) comprises the polypeptide (a) or (b) as a partial sequence thereof and has immunity-inducing activity. Specifically, the polypeptide (c) corresponds to the polypeptide (a) or (b) to which other amino acid(s) or polypeptide(s) are added at one or both ends thereof and having immunity-inducing activity. Such polypeptide can be used for preparing the immunity-inducing agent of the present invention.

The above-mentioned polypeptide can be chemically synthesized in accordance with, for example, the Fmoc (fluorenylmethyloxycarbonyl) method or the tBoc (t-butyloxycarbonyl) method (the Japanese Biochemical Society (ed.), Seikagaku Jikken Kouza (the Course for Biochemical Experiment) 1, Tanpakushitsu no Kagaku (Chemistry of Protein) IV, Kagaku Shushoku to Peptide Gousei (Chemical Modification and Peptide Synthesis), Tokyo Kagaku Dojin, Japan, 1981). Also, a variety of commercially available peptide synthesizers can be used to synthesize the polypeptide in accordance with a conventional technique. Further, known genetic engineering techniques (e.g., Sambrook et al., Molecular Cloning, vol. 2, Current Protocols in Molecular Biology, 1989, Cold Spring Harbor Laboratory Press; and Ausubel et al., Short Protocols in Molecular Biology, vol. 3, A compendium of Methods from Current Protocols in Molecular Biology, 1995, John Wiley & Sons) may be employed to prepare a polynucleotide encoding the above polypeptide, the resulting polypeptide may be incorporated into an expression vector and then introduced into a host cell, and the polypeptide may be produced in such host cell to obtain the target polypeptide.

A polynucleotide encoding the above polypeptide can be easily prepared via a known genetic engineering technique or a conventional technique using a commercially available nucleic acid synthesizer. For example, DNA having the nucleotide sequence of SEQ ID NO: 1 can be prepared by performing PCR with the use of the human chromosome DNA or cDNA library as a template and a pair of primers designed so as to amplify the nucleotide sequence shown by SEQ ID NO: 1. Similarly, DNA having the nucleotide sequence of SEQ ID NO: 5 can be prepared with the use of the canine chromosome DNA or cDNA library as the template. PCR conditions can be adequately determined. For example, a reaction cycle of denaturation at 94° C. for 30 seconds, annealing at 55° C. for 30 seconds to 1 minute, and extension at 72° C. for 2 minutes with the use of thermostable DNA polymerase (e.g., Taq polymerase) and $Mg^{2+}$-containing PCR buffer is repeated 30 times, followed by the reaction at 72° C. for 7 minutes, although the reaction conditions are not limited thereto. PCR techniques, conditions, and the like are described in, for example, Ausubel et al., Short Protocols in Molecular Biology, vol. 3, A compendium of Methods from Current Protocols in Molecular Biology, 1995, John Wiley & Sons (Chapter 15, in particular). Also, adequate probes or primers may be prepared based on the information of the nucleotide sequences and the amino acid sequences shown by SEQ ID NOs: 1 to 30 in the Sequence Listing of the present invention, and human, canine, bovine, or other cDNA libraries may be screened for with the use of such probes or primers, so that DNA of interest can be isolated. cDNA libraries are preferably prepared from cells, organs, or tissue in which a protein shown by any even SEQ ID number among SEQ ID NOs: 2 to 30 is expressed. Procedures, such as preparation of probes or primers, construction of cDNA library, screening of cDNA library, and cloning of target genes, described above are known in the art. For example, such procedures can be carried out in accordance with the methods described in Sambrook et al., Molecular Cloning, vol. 2, Current Protocols in Molecular Biology, 1989), Ausubel et al. (as above). DNA encoding polypeptide (a) above can be obtained from DNA thus obtained. Since a codon encoding each amino acid is known, a nucleotide sequence of a polynucleotide encoding a particular amino acid sequence can be easily identified. Accordingly, the nucleotide sequence of a polynucleotide encoding polypeptide (b) or (c) can be easily identified, and such polynucleotide can also be easily synthesized with the use of a commercially available nucleic acid synthesizer in accordance with a conventional technique.

The host cells may be any cells, provided that the aforementioned polypeptide can be expressed therein. The host cells include, but not limited to, an *E. coli* cell as prokaryotic cells; and monkey kidney cells (COS1), chinese hamster ovary (CHO) cells, the human embryonic kidney cell line (HEK293), and the fetal mouse skin cell line (NIH3T3), budding yeast cells, dividing yeast cells, silk worm cells, and xenopus egg cells as eukaryotic cells When prokaryotic host cells are used, expression vectors having, for example, an origin, a promoter, a ribosome-binding site, a multi-cloning site, a terminator, a drug-tolerant gene, and an auxotrophic complementary gene that can be replicated in prokaryotic cells, are used. Examples of *E. coli* expression vectors include pUC, pBluescriptII, the pET expression system, and the pGEX expression system. DNA encoding the above polypeptide may be incorporated into such expression vector, prokaryotic host cells may be transformed with such vector, and the resulting transformant may be cultured. Thus, a polypeptide encoded by the DNA can be expressed in prokaryotic host cells. In this case, such polypeptide can be expressed in the form of a fusion protein with another protein.

When eukaryotic host cells are used, eukaryotic cell expression vectors having, for example, a promoter, a splicing region, and a poly(A) addition site are used. Examples of such expression vectors include pKA1, pCDM8, pSVK3, pMSG, pSVL, pBK-CMV, pBK-RSV, EBV, pRS, pcDNA3, and pYES2 vectors. As described above, DNA encoding the above polypeptide may be incorporated into such expression vector, eukaryotic host cells may be transformed with such vector, and the resulting transformant may then be cultured. Thus, a polypeptide encoded by the DNA can be expressed in eukaryotic host cells. When pIND/V5-His, pFLAG-CMV-2, pEGFP-N1, pEGFP-Cl, or other expression vectors are used, the polypeptide can be expressed in the form of a fusion protein with a variety of tags, such as His tag (e.g., $(His)_6$ to $(His)_{10}$), FLAG tag, myc tag, HA tag, or GFP.

Expression vectors can be introduced into host cells via conventional techniques, such as electroporation, the calcium phosphate method, the liposome method, the DEAE-dextran method, microinjection, virus infection, lipofection, or binding with a cell-permeable peptide.

The target polypeptide can be isolated and purified from host cells by employing known separation techniques in combination. Examples thereof include, but are not limited to, treatment with the use of a denaturing agent such as urea or a surfactant, ultrasonication, enzyme digestion, salting out or fractional precipitation with a solvent, dialysis, centrifugation, ultrafiltration, gel filtration, SDS-PAGE, isoelectric focusing, ion exchange chromatography, hydrophobic chromatography, affinity chromatography, and reverse phase chromatography.

Some polypeptides obtained by such methods are in the form of fusion proteins with any other proteins as described above. Examples thereof include fusion proteins with glutathione-S-transferase (GST) or His tag. Such polypeptides in the form of fusion proteins are within the scope of the present invention as polypeptide (c). Further, polypeptides expressed in transformed cells are translated, and the translated polypeptides occasionally undergo various types of modification in the cells. Such post-translationally modified polypeptides are also within the scope of the present invention, provided that such polypeptides have immunity-inducing activity. Examples of such post-translational modification include elimination of N-terminal methionine, N-terminal acetylation, sugar chain addition, limited degradation with intracellular protease, myristoylation, isoprenylation and phosphorylation.

<Immunity-Inducing Agent>

As specifically described in the examples below, administration of the above-mentioned polypeptide having immunity-inducing activity to a cancer-bearing living body enables regression of an existing tumor. Thus, the immunity-inducing agent of the present invention can be used as a therapeutic and/or preventive agent for cancer.

The terms "tumor" and "cancer" used herein refer to malignant neoplasms, and these terms are used interchangeably with each other.

In this case, target cancers are those expressing a gene encoding a polypeptide comprising an amino acid sequence shown by any even SEQ ID number among SEQ ID NOs: 2 to 30 or a partial sequence thereof consisting of at least 7 contiguous amino acids. Preferably, such cancers are breast cancer, brain tumor, leukemia, lung cancer, lymphoma, mast cell tumor, esophagus cancer, and colorectal cancer. Examples of such specified cancers include, but are not limited to, mammary gland cancer, combined mammary gland cancer, malignant mixed tumor of the mammary gland, intraductal papillary adenocarcinoma, chronic lymphocytic leukemia, gastrointestinal lymphoma, digestive lymphoma, and small to medium cell lymphoma.

Target animals are mammalians, and examples thereof include mammalian animals, including primates, pet animals, livestock animals, and competitive animals, with humans, dogs, and cats being particularly preferable.

The immunity-inducing agent of the present invention may be administered orally or parenterally to an organism. Parenteral administration, such as intramuscular, subcutaneous, intravenous, or intraarterial administration, is preferable. When such immunity-inducing agent is used for the purpose of cancer treatment, the agent can be administered to the regional lymph node in the vicinity of the tumor to be treated, so as to improve the antitumor effects as described in the examples below. The dose may be any amount as long as it is effective for immunity induction. When the agent is used for treatment and/or prevention of cancer, for example, an amount effective for treatment and/or prevention of cancer is sufficient, and such amount can be altered depending on, for example, the body weight, sex (i.e., male or female), or symptom of an animal. The amount effective for treatment and/or prevention of cancer is adequately determined in accordance with the tumor size, symptoms, or other conditions. In general, an effective amount for a target animal per day is 0.0001 μg to 1,000 μg, and preferably 0.001 μg to 1,000 μg, and the agent can be administered via a single dose or a plurality of doses. Preferably, the agent is administered via several separate doses every several days or months. As specifically described in the examples below, the immunity-inducing agent of the present invention enables regression of an existing tumor. Thus, the agent can exert the antitumor effects on a small number of cancer cells in an early developmental stage. Use thereof before the onset of cancer or after treatment leads to prevention of the development or recurrence of cancer. Specifically the immunity-inducing agent of the present invention is useful for treatment and prevention of cancer.

The immunity-inducing agent of the present invention may consist of a polypeptide, or it may be adequately mixed with an additive that is suitable for a relevant dosage form, such as a pharmaceutically acceptable carrier, a diluent, an excipient, or the like. Methods of preparing an agent and additives that can be used are well-known in the medical preparation field, and any methods and additives can be employed. Specific examples of additives include, but are not limited to: diluents, such as physiological buffer solutions; excipients, such as sugar, lactose, corn starch, calcium phosphate, sorbitol, and glycine; binders, such as syrup, gelatin, gum Arabic, sorbitol, polyvinyl chloride, and tragacanth; and lubricants, such as magnesium stearate, polyethylene glycol, talc, and silica. Examples of forms of preparations include oral agents, such as tablets, capsules, granules, powders, and syrup solutions, and parenteral agents, such as inhalants, injection preparations, suppositories, and liquid drugs. Such agents can be prepared by common methods.

The immunity-inducing agent of the present invention can be used in combination with an immunopotentiating agent capable of potentiating an immunological response in vivo.

The immunopotentiating agent may be incorporated into the immunity-inducing agent of the present invention, or it may be administered to a patient as another composition in combination with the immunity-inducing agent of the present invention.

The term "patient" used herein refers to an animal, a mammalian animal in particular, and it is preferably a human, dog, or cat.

An example of the immunopotentiating agent is an adjuvant. An adjuvant provides an antigen reservoir (outside the cell or in the macrophage), it activates the macrophage, and it stimulates lymphocytes in a given tissue. Thus, an adjuvant can potentiate an immunological response and enhance the antitumor effects. When the immunity-inducing agent of the present invention is used for treatment and/or prevention of cancer, accordingly, it is particularly preferable that the immunity-inducing agent further comprise an adjuvant in addition to the polypeptide as an active ingredient. Various types of adjuvants are well-known in the art, and any such adjuvants can be used. Specific examples thereof include: MPL (SmithKline Beecham); an equivalent obtained by purification and acid hydrolysis of a lipopolysaccharide of *Salmonella minnesota* Re 595; QS21 (SmithKline Beecham); a pure saponin QA-21 purified from the *Quillja saponaria* extract; DQS21 disclosed in the PCT application (WO 96/33739, SmithKline Beecham); QS-7, QS-17, QS-18, and QS-L1 (So et al., Molecules and Cells, 1997, 7: 178-186); Freund's incomplete adjuvant; Freund's complete adjuvant; vitamin E; Montanide; alum; CpG oligonucleotide (e.g., Kreig et al., Nature, 1995, 374: 546-549); poly IC and a derivative thereof (e.g., poly ICLC); and various water-in-oil emulsions prepared from biodegradable oil, such as squalene and/or tocopherol. Freund's incomplete adjuvant, Montanide, poly I:C, a derivative thereof, and CpG oligonucleotide are particularly preferable. The rate of the adjuvant mixed with a polypeptide is typically about 1:10 to 10:1, preferably about 1:5 to 5:1, and further preferably about 1:1. It should be noted that adjuvants are not limited to those exemplified above, and other adjuvants known in the art can also be used at the time of administration of the immunity-inducing agent of the present invention (e.g., Goding, Monoclonal Antibodies: Principles and Practice, vol. 2, 1986). A method for preparing a mixture of polypeptide and adjuvant or an emulsion is well-known to a person skilled in the field of immunization.

As the immunopotentiating agent, factors that stimulate an immunological response of interest can be used in addition to the aforementioned adjuvants. For example, various cytokines that stimulate lymphocytes or antigen-presenting cells can be used as the immunopotentiating agent in combination with the immunity-inducing agent of the present invention.

Many cytokines that can potentiate immunological responses are known in the art. Examples thereof include, but are not limited to, interleukin-12 (IL-12), GM-CSF, IL-18, interferon α, interferon γ, interferon ω, interferon γ, and Flt3 ligand that are known to potentiate the protective effects of a vaccine. Such factor can be used as the immunopotentiating agent and can be administered to a patient in the form of a mixture thereof with the immunity-inducing agent of the present invention or in combination with the immunity-inducing agent of the present invention as another composition.

<Antigen-Presenting Cell>

Further, the above-mentioned polypeptides may be brought into contact with antigen-presenting cells in vitro to present such polypeptides to the antigen-presenting cells. Specifically, the polypeptides (a) to (c) can be used as agents for treating the antigen-presenting cells. Examples of antigen-presenting cells include dendritic cells, B cells, and macrophages, and dendritic cells or B cells having MHC class 1 molecules are preferably used. A variety of MHC class 1 molecules have been identified and well-known. Human MHC molecules are referred to as "HLA." Examples of HLA class 1 molecules include HLA-A, HLA-B, and HLA-C. Specific examples include HLA-A1, HLA-A0201, HLA-A0204, HLA-A0205, HLA-A0206, HLA-A0207, HLA-A11, HLA-A24, HLA-A31, HLA-A6801, HLA-B7, HLA-B8, HLA-B2705, HLA-B37, HLA-Cw0401, and HLA-Cw0602.

Dendritic cells or B cells having MHC class 1 molecules can be prepared from the peripheral blood by a well-known technique. For example, dendritic cells are induced from the bone marrow, umbilical blood, or peripheral blood of a patient with the use of the granulocyte-macrophage colony-stimulating factors (GM-CSF) and IL-3 (or IL-4), and tumor-associated peptides are added to the culture system. Thus, tumor-specific dendritic cells can be induced.

Administration of an effective amount of such dendritic cells enables induction of a response desirable for cancer treatment. Examples of cells that can be used include the bone marrow and the umbilical blood provided by a healthy individual and the bone marrow and the peripheral blood of the patient. When the patient's own autologous cells are used, a safety level is high, and serious side effects can be avoided. The peripheral blood or bone marrow may be a fresh, hypothermically stored, or cryopreserved sample. The peripheral blood may be prepared by culturing the whole blood or by culturing the separated leukocyte components, with the latter being preferable from the viewpoint of efficiency. Further, mononuclear cells may be isolated from the leukocyte components. When the sample is prepared from the bone marrow or umbilical blood, the entire cells that constitute the bone marrow may be cultured, or mononuclear cells may be separated therefrom and cultured. The peripheral blood, the leukocyte component thereof, and the bone marrow cells comprise mononuclear cells, hematopoietic stem cells, immature dendritic cells, or CD4+ cells from which dendritic cells originate. Cytokines may be of a naturally-occurring or gene recombinant type, and methods for producing the same are not limited, provided that safety and physiological activities thereof have been verified. Preferably, the minimum requirement of samples with verified medical qualities is used. The concentration of cytokine added is not particularly limited, provided that dendritic cells are induced. In general, the total cytokine concentration of approximately 10 to 1,000 ng/ml is preferable, and about 20 to 500 ng/ml is further preferable. Culture can be conducted with the use of a well-known medium that is generally used for leukocyte culture. A culture temperature is not particularly limited, provided that leukocytes can be multiplied, and the human body temperature (i.e., approximately 37° C.) is the most preferable. A gaseous environment during culture is not particularly limited, provided that leukocytes can be multiplied. Aeration with 5% $CO_2$ is preferable. Further, a culture duration is not particularly limited, provided that a necessary number of cells is induced. It is generally 3 days to 2 weeks. An adequate apparatus can be used for cell separation or culture, and it is preferable that such apparatus have the approved medical safety and stable and simple operability. In particular, cell culture apparatuses are not limited to common containers, such as petri-dishes, flasks, and bottles, and laminated or multistage containers, roller bottles, spinner bottles, bag-type culture apparatus, hollow fiber columns, or the like can also be used.

The above-mentioned polypeptides can be brought into contact with antigen-presenting cells in vitro via a well-known technique. For example, antigen-presenting cells can be cultured in a coluture solution containing such polypeptides. Peptide concentration in a medium is not particularly limited. In general, it is about 1 to 100 μg/ml, and preferably about 5 to 20 μg/ml. Cell density during culture is not particularly limited, and it is generally about $10^3$ to $10^7$ cells/ml, and preferably about $5×10^4$ to $5×10^6$ cells/ml. It is preferable that culture be conducted at 37° C. in 5% $CO_2$ in accordance with a conventional technique. A peptide length that can be presented on the antigen-presenting cell surface is generally about 30 amino acid residues at maximum. When antigen-presenting cells are brought into contact with polypeptides in vitro, accordingly, the length of the polypeptide may be adjusted to about 30 amino acid residues or less, although the length is not particularly limited thereto.

By culturing antigen-presenting cells in the presence of the polypeptides, peptides are incorporated into MHC molecules of the antigen-presenting cells and presented on the surfaces thereof. Thus, the isolated antigen-presenting cells containing the complex of polypeptides and MHC molecules can be prepared with the use of such polypeptides. Such antigen-presenting cells can present the polypeptides to T cells in vivo or in vitro, induce cytotoxic T cells specific for the polypeptides, and multiply such T cells.

The thus-prepared antigen-presenting cells containing the complex of polypeptides and MHC molecules may be brought into contact with T cells in vitro, so that cytotoxic T cells specific for such polypeptides can be induced and multiplied. It can be achieved by culturing the antigen-presenting cells together with the T cells in a liquid medium. For example, culture can be conducted by suspending antigen-presenting cells in a liquid medium, introducing the resulting suspension into a container such as wells of a microplate, and adding T cells thereto. The mixing ratio of antigen-presenting cells to T cells at the time of coculture is not particularly limited, and it is generally about 1:1 to 1:10, and preferably about 1:5 to 1:20 in terms of the cell count. Also, the density of antigen-presenting cells suspended in a liquid medium is not particularly limited, and it is generally about 100 to $10^7$ cells/ml, and preferably about $10^4$ to $10^6$ cells/ml. Co-culture is preferably carried out in accordance with a conventional technique at 37° C. in 5% $CO_2$. A culture duration is not particularly limited, and it is generally 2 days to 3 weeks, and preferably about 4 days to 2 weeks. It is preferable that coculture be carried out in the presence of a single type or a plurality of types of interleukins, such as IL-2, IL-6, IL-7, and IL-12. In such a case, IL-2 or IL-7 concentration is generally about 5 U/ml to 20 U/ml, IL-6 concentration is generally about 500 U/ml to 2,000 U/ml, and IL-12 concentration is generally about 5 ng/ml to 20 ng/ml, although the concentration is not limited thereto. The unit "U" used herein indicates a unit of activity. Co-culture may be repeated once or several times with the addition of fresh antigen-presenting cells. For example, the culture supernatant after coculture is discarded, coculture is further carried out with the addition of a suspension of fresh antigen-presenting cells, and such procedure may be repeated once or several times. Coculture conditions may be as described above.

Cytotoxic T cells specific for the polypeptides are induced and multiplied via the co-culture. Thus, isolated T cells that selectively bind to the complex of polypeptides and MHC molecules can be prepared with the use of the above polypeptides.

As described in the Examples below, genes encoding polypeptides of any even SEQ ID number among SEQ ID NOs: 2 to 30 are expressed specifically in the breast cancer cells, the leukemia cells, and the lymphoma cells. Accordingly, it is considered that a significantly larger number of polypeptides of even SEQ ID numbers among SEQ ID NOs: 2 to 30 are present in such cancer cells than in normal cells. When some polypeptides in cancer cells are presented to the MHC molecules on the cancer cell surface and the cytotoxic T cells prepared as described above are administered into a living body, cytotoxic T cells can disrupt cancer cells using the same as a marker. Since the antigen-presenting cells presenting the polypeptides are capable of inducing and multiplying cytotoxic T cells specific for the polypeptides in vivo, administration of the antigen-presenting cells into a living body can also disrupt cancer cells. That is, the cytotoxic T cells prepared with the use of the polypeptides or the antigen-presenting cells are useful as the therapeutic and/or preventive agent for cancer as with the immunity-inducing agent of the present invention.

When the isolated antigen-presenting cells or isolated T cells are administered to a living body, it is preferable that such isolated cells are prepared from the antigen-presenting cells or T cells sampled from the patient who receives the treatment with the use of the polypeptides (a) to (c) in order to avoid an immunological response that recognize such cells as foreign matter and attacks such cells in vivo.

The route of administration of a therapeutic and/or preventive agent for cancer comprising, as an active ingredient, the antigen-presenting cells or isolated T cells is preferably a parenteral route, such as intravenous or intraarterial administration. A dosage is adequately selected in accordance with the symptom, the purpose of administration, and other conditions, and in general, 1 to $10^{13}$ cells, and preferably $10^6$ to $10^9$ cells are used for administration, and such cells are preferably administered once every several days or several months. A preparation may be, for example, a suspension of cells in a physiological buffered saline solution, and it can be used in combination with other antitumor agents or cytokines. Also, one or more additives well-known in the medical preparation field can be added.

<Gene-Based Vaccine>

Polynucleotides encoding the polypeptides (a) to (c) may be expressed in the body of a target animal, so that antibody production or cytotoxic T cells can be induced in the body, and effects equivalent to those attained via polypeptide administration can be attained. Specifically, the immunity-inducing agent of the present invention may comprise polynucleotides encoding the polypeptides (a) to (c) and comprise, as an active ingredient, a recombinant vector capable of expressing such polypeptide in vivo. Such recombinant vector capable of expressing an antigen polypeptide is also referred to as a "gene-based vaccine."

A vector used for preparing a gene-based vaccine is not particularly limited, provided that it can express polypeptides of interest in the target animal cells (preferably mammalian animal cells). It may be a plasmid or virus vector, and any vector known in the gene-based vaccine field may be used. Polynucleotides, such as DNA or RNA encoding the polypeptides, can be easily prepared in accordance with a conventional technique as described above. Also, the polynucleotides can be incorporated into a vector by a method well-known in the art.

Preferably, a gene-based vaccine is administered parenterally (e.g., intramuscular, subcutaneous, intravenous, or intraarterial administration), and the dosage can be adequately selected in accordance with an antigen type or other conditions. A dosage is generally about 0.1 mg to 100 mg, and preferably about 1 µg to 10 mg, in terms of the weight of the gene-based vaccine per kg of the body weight.

Examples of methods involving the use of virus vectors include methods in which the polynucleotide encoding the above polypeptide is incorporated into the RNA virus or DNA virus, such as retrovirus, lentivirus, adenovirus, adeno-associated virus, herpes virus, vaccinia virus, poxvirus, poliovirus, or Sindbis virus, and the target animal is infected therewith. Methods involving the use of retrovirus, adenovirus, adeno-associated virus, or vaccinia virus are particularly preferable.

Examples of other methods include a method in which an expression plasmid is directly administered into the muscle (the DNA vaccine method), the liposome method, the Lipofectin method, microinjection, the calcium phosphate method, and electroporation, with the DNA vaccine method and the liposome method being particularly preferable.

The gene encoding the polypeptide used in the present invention is actually allowed to function as a pharmaceutical product by the in vivo method in which the gene is introduced directly into the body or the ex vivo method in which a given cell is sampled from a target animal, the gene is introduced into the cell ex vivo, and the cell is then returned into the body (Nikkei Science (the Japanese version of Scientific American), April 1994, pp. 20-45, Japan; Gekkan Yakuji (the Pharmaceuticals Monthly), 1994, vol. 36, No. 1, pp. 23-48, Japan; Jikken Igaku Zoukan (an extra number of Experimental Medicine), 1994, vol. 12, No. 15, Japan; and cited documents thereof). The in vivo method is more preferable.

When a pharmaceutical agent is administered via the in vivo method, the agent can be administered through an adequate route in accordance with diseases, symptoms, and other conditions of the target of treatment. For example, administration can be carried out intravenously, intraarterially, subcutaneously, or intramuscularily. When the agent is administered via the in vivo method, for example, the agent can be in the form of a liquid drug. In general, the agent is in the form of an injection preparation containing DNA encoding the peptide of the present invention as an active ingredient, and common carriers may be added according to need. Also, the liposome or membrane fusion liposome (e.g., hemagglutinating virus of Japan (HVJ)-liposome) comprising the DNA can be in the form of a liposome preparation such as a suspension, cryogen, or cryogen condensed by centrifugation.

In the present invention, the term "the nucleotide sequence shown by SEQ ID NO: 1" refers not only to the nucleotide sequence that is actually shown by SEQ ID NO: 1 but also a sequence complementary thereto. Accordingly, the term "a polynucleotide having the nucleotide sequence shown by SEQ ID NO: 1" refers to a single-stranded polynucleotide having the nucleotide sequence that is actually shown by SEQ ID NO: 1, a single-stranded polynucleotide comprising a nucleotide sequence complementary thereto, and a double-stranded polynucleotide comprised of such single-stranded polynucleotides. When preparing a polynucleotide encoding the polypeptide used in the present invention, an adequate nucleotide sequence is to be selected. A person skilled in the art would readily select such adequate sequence.

EXAMPLES

Hereafter, the present invention is described in greater detail with reference to the Examples, although the technical scope of the present invention is not limited to the concrete examples below.

Example 1

Acquisition of Novel Cancer Antigen Protein by the SEREX Method (1) Preparation of cDNA Library Total RNA was extracted from the testicular tissue of a healthy dog by the acid guanidium-phenol-chloroform method, and poly(A) RNA was purified with the use of the Oligotex-dT30 mRNA purification Kit (Takara Shuzo Co., Ltd.) in accordance with the protocols included in the kit.

The canine testis cDNA phage library was synthesized using the obtained mRNA (5 µg). The cDNA phage library was prepared using the cDNA Synthesis Kit, the ZAP-cDNA Synthesis Kit, and the ZAP-cDNA GigapackIII Gold Cloning Kit (STRATAGENE) in accordance with the protocols included in the kits. The size of the prepared cDNA phage library was $7.73 \times 10^5$ pfu/ml.

(2) Screening of cDNA Library with the Use of Serum

Immuno screening was carried out using the canine testis cDNA phage library prepared above. Specifically, host E. coli cells (XL1-Blue MRF') was infected with the phage library in 2,210 clones per a NZY agarose plate (Φ90×15 mm), cultured at 42° C. for 3 to 4 hours to form plaques, the plate was covered with the nitrocellulose membrane (Hybond C Extra: GE Healthcare Bio-Science) infiltrated with IPTG (isopropyl-β-D-thiogalactoside) at 37° C. for 4 hours to induce and express proteins, and the proteins were transferred onto the membrane. Thereafter, the membrane was recovered, immersed in TBS containing 0.5% dried skim milk (10 mM Tris-HCl, 150 mM NaCl, pH 7.5), and shaken at 4° C. overnight to block a non-specific reaction. The filter was allowed to react with the 500-fold diluted serum of a clinically affected dog at room temperature for 2 to 3 hours.

As the serum of the clinically affected dog, the serum sampled from a dog with breast cancer was used. The serum samples were stored at −80° C. and pretreated immediately before use. The serum samples were pretreated in the following manner. Specifically, host E. coli cells (XL1-BLue MRF') were infected with the λZAP Express phages into which no foreign genes had been introduced, and culture was then conducted on the NZY plate medium at 37° C. overnight. Subsequently, 0.2 M NaHCO$_3$ buffer (pH 8.3) containing 0.5M NaCl was added to the plate, the plate was allowed to stand at 4° C. for 15 hours, and the supernatant was recovered as an E. coli/phage extract. Subsequently, the recovered E. coli/phage extract was allowed to flow through the NHS-column (GE Healthcare Bio-Science), and proteins derived from E. coli/phages were immobilized thereon. The serum of a clinically affected dog was allowed to flow through the protein-immobilized column for reacting therewith, and antibodies that had adsorbed to E. coli and phages were removed from the serum. The serum fraction that had flowed through the column was diluted 500-fold with TBS containing 0.5% dried skim milk, and the resultant was used as an immuno-screening sample.

The membrane onto which such treated serum and above-mentioned fusion protein had been blotted was washed 4 times with TBS-T (0.05% Tween 20/TBS), the goat anti-dog IgG (goat anti-dog IgG-h+I HRP conjugated: BETHYL Laboratories), which had been diluted 5,000-fold with TBS containing 0.5% dried skim milk as the secondary antibody, was allowed to react therewith at room temperature for 1 hour, detection was carried out via the enzymatic color-developing reaction using the NBT/BCIP reaction solution (Roche), colonies that correspond to the region positive for the color-development were removed from the NZY agarose plate (Φ90×15 mm), and the removed colonies were dissolved in 500 µl of SM buffer (100 mM NaCl, 10 mM MgClSO$_4$, 50 mM Tris-HCl, 0.01% gelatin, pH 7.5). The secondary and the tertiary screenings were repeated until the color-development-positive colonies represented single clones in the same manner as described above, and 5 positive clones were isolated as a result of screening 30,940 phage clones that react with IgG in the serum.

(3) Homology Search of Isolated Antigen Gene

In order to subject the 5 positive clones isolated in the above-described manner to nucleotide sequence analysis, phage vectors were converted into plasmid vectors. Specifically, 200 µl of a solution of host E. coli (XL1-Blue MRF') adjusted at OD$_{600}$ of 1.0 was mixed with 250 µl of the purified phage solution and 1 µl of ExAssist helper phage (STRATAGENE), the resultant was subjected to the reaction at 37° C. for 15 minutes, 3 ml of LB medium was added, culture was conducted at 37° C. for 2.5 to 3 hours, the culture product was incubated in a water bath at 70° C. for 20 minutes immediately thereafter, the resultant was centrifuged at 4° C. and 1,000×g for 15 minutes, and the supernatant was recovered as a phagemid solution. Subsequently, 200 µl of a solution of phagemid host E. coli (SOLR) adjusted at OD$_{600}$ of 1.0 was mixed with 10 µl of the purified phage solution, the resultant was subjected to the reaction at 37° C. for 15 minutes, 50 µl thereof was seeded on LB agar medium containing ampicillin (final concentration: 50 µg/ml), and culture was conducted at 37° C. overnight. A single colony of the transformed SOLR was picked up and cultured in LB agar medium containing ampicillin (final concentration: 50 µg/ml) at 37° C., and plasmd DNA having an insert of interest was purified using the QIAGEN plasmid Miniprep Kit (QIAGEN).

The purified plasmid was subjected to analysis of the full-length sequence of the insert via primer walking using the T3 primer of SEQ ID NO: 31 and the T7 primer of SEQ ID NO: 32. The gene sequences shown by SEQ ID NOs: 5, 7, 9, 11, and 13 were obtained via the sequence analysis. The nucleotide sequences of the genes and the amino acid sequences thereof (SEQ ID NOs: 6, 8, 10, 12, and 14) were used to perform homology search with the known genes with the use of a homology search program, BLAST (http://www.ncbi.nlm.nih.gov/BLAST/). As a result, all the 5 obtained genes were found to encode CAPRIN-1. Sequence identity among the 5 genes was as follows: the nucleotide sequence identity of 100% and the amino acid sequence identity of 99% in regions to be translated into proteins. Sequence identity of the gene with a gene encoding a human homologue was as follows: the nucleotide sequence identity of 94% and the amino acid sequence identity of 98% in regions to be translated into proteins. The nucleotide sequences of the human homologues are shown by SEQ ID NOs: 1 and 3 and the amino acid sequences thereof are shown by SEQ ID NOs: 2 and 4.

Sequence identity of the obtained canine gene with a gene encoding a bovine homologue was as follows: the nucleotide sequence identity of 94% and the amino acid sequence identity of 97% in regions to be translated into proteins. The nucleotide sequence of the bovine homologue is shown by SEQ ID NO: 15 and the amino acid sequence thereof is shown by SEQ ID NO: 16. Sequence identity between the gene encoding the human homologue and the gene encoding the bovine homologue was as follows: the nucleotide sequence identity of 94% and the amino acid sequence identity of 93% to 97% in regions to be translated into proteins. Sequence identity of the obtained canine gene with a gene encoding a horse homologue was as follows: the nucleotide sequence identity of 93% and the amino acid sequence identity of 97% in regions to be translated into proteins. The nucleotide sequence of the horse homologue is shown by SEQ ID NO: 17 and the amino acid sequence thereof is shown by SEQ ID NO: 18. Sequence identity between the gene encoding the human homologue and the gene encoding the horse homologue was as follows: the nucleotide sequence identity of 93% and the amino acid sequence identity of 96% in regions to be translated into proteins. Sequence identity of the obtained canine gene with a gene encoding a mouse homologue was as follows: the nucleotide sequence identity of 87% to 89% and the amino acid sequence identity of 95% to 97% in regions to be translated into proteins. The nucleotide sequences of the mouse homologues are shown by SEQ ID NOs: 19, 21, 23, 25, and 27 and the amino acid sequences thereof are shown by SEQ ID NOs: 20, 22, 24, 26, and 28. Sequence identity between a gene encoding a human homologue and a gene encoding a mouse homologue was as follows: the nucleotide sequence identity of 89% to 91% and the amino acid sequence identity of 95% to 96% in regions to be translated into proteins. Sequence identity of the obtained canine gene with a gene encoding a chicken homologue was as follows: the nucleotide sequence identity of 82% and the amino acid sequence identity of 87% in regions to be translated into proteins. The nucleotide sequence of the chicken homologue is shown by SEQ ID NO: 29 and the amino acid sequence thereof is shown by SEQ ID NO: 30. Sequence identity between a gene encoding a human homologue and a gene encoding a chicken homologue was as follows: the nucleotide sequence identity of 81% to 82% and the amino acid sequence identity of 86% in regions to be translated into proteins.

(4) Gene Expression Analysis in Tissue

Expression of the genes obtained in the above-described manner in canine and human normal tissues and various cell strains was examined via reverse transcription-PCR (RT-PCR). Reverse transcription was carried out in the following manner Specifically, total RNA was extracted from 50 to 100 mg of tissue samples and 5 to $10 \times 10^6$ cell strains with the use of the TRIzol reagent (Invitrogen) in accordance with the protocol included therein. cDNA was synthesized with the use of the extracted total RNA using the Superscript First-Strand Synthesis System for RT-PCR (Invitrogen) in accordance with the protocol included therein. PCR was carried out using primers specific for the obtained genes (shown by SEQ ID NOs: 33 and 34) in the following manner. Specifically, reagents (0.25 µl of the sample prepared via reverse transcription, 2 µM each of the primers, 0.2 mM each of dNTPs, and 0.65 U of ExTaq polymerase (Takara Shuzo Co., Ltd.)) were mixed with an accompanying buffer to be adjusted to match the total volume of 25 µl. The resultant was subjected to the reaction of 30 cycles at 94° C. for 30 seconds, 60° C. for 30 seconds, and 72° C. for 30 seconds using the Thermal Cycler (BIO RAD). The above gene-specific primers were used to amplify a region from nucleotides 206 to 632 of the nucleotide sequence shown by SEQ ID NO: 5 (i.e., the canine CAPRIN-1 gene) and a region from nucleotides 698 to 1124 of the nucleotide sequence shown by SEQ ID NO: 1 (i.e., the human CAPRIN-1 gene). For comparison, GAPDH-specific primers (as shown by SEQ ID NOs: 35 and 36) were simultaneously used. As a result, potent expression was observed in a healthy canine testis tissue, and expression was observed in canine breast cancer and adenocarcinoma tissue, shown in FIG. 1. Further, expression of the human homologue of the obtained gene was also examined, and expression thereof was observed only in the testis in the case of normal tissue, as with the case of the canine CAPRIN-1 gene. However, expression thereof was detected in a wide variety of cancer cell lines, such as breast cancer, brain tumor, leukemia, lung cancer, and esophagus cancer cell lines, and, in particular, expression thereof was observed in many breast cancer cell lines. The results demonstrate that CAPRIN-1 expression is not observed in normal tissues other than the testis tissue, however, CAPRIN-1 is expressed in many cancer cells, and breast cancer cell lines, in particular.

In FIG. 1, Reference number 1 on the vertical axis shows the expression pattern of the gene identified above and Reference number 2 shows the expression pattern of the control GAPDH gene.

(5) Immunohistochemical Staining (5)-1: CAPRIN-1 Expression in Mouse and Canine Normal Tissue Mice (Balb/c, female) and dogs (beagle dogs, female) were exsanguinated under ether anesthesia and under ketamine/isoflurane anesthesia, the abdominal cavity was opened, and organs (stomach, liver, eyeball, thymus, muscle, bone marrow, uterus, small intestine, esophagus, heart, kidney, salivary gland, large intestine, mammary gland, brain, lung, skin, adrenal gland, ovary, pancreas, spleen, and bladder) were independently transferred to a PBS-containing 10-cm dish. The organs were incised in PBS and immobilized with 0.1 M phosphate buffer containing 4% paraformaldehyde (PFA) (pH 7.4) under reflux conditions overnight. A reflux solution was discarded, the tissue surfaces of the organs were rinsed with PBS, a PBS solution containing 10% sucrose was introduced into a 50-ml centrifuge tube, and tissues were introduced therein and shaken at 4° C. for 2 hours using a rotor. The resultant was transferred into a PBS solution containing 20% sucrose, it was allowed to stand at 4° C. until the tissues settled, and then it was transferred into a PBS solution containing 30% sucrose and allowed to stand at 4° C. until the tissues settled. The tissues were removed and necessary regions were excised using a surgical scalpel. Subsequently, the OCT compound (Tissue Tek) was applied on the tissue surface, and the tissues were then placed on the Cryomold. After the Cryomold was placed on dry ice and rapidly frozen, the tissues were sliced to a thickness of 10 µm to 20 µm using the cryostat (LEICA), and the tissue slices on glass slides were air-dried with a hair drier for 30 minutes to prepare glass slides having tissue slices thereon. Subsequently, the glass slides were introduced into a staining jar filled with PBS-T (physiological saline containing 0.05% Tween 20), PBS-T was replaced with fresh PBS-T every 5 minutes, and this procedure was repeated 3 times. Extra moisture around the slices was wiped off using Kimwipes, the slices were encircled with Dakopen (DAKO), a MOM mouse Ig blocking reagent (VECTASTAIN) was placed on the mouse tissue as a blocking solution, a PBS-T solution containing 10% fetal bovine serum was placed on the canine tissue as a blocking solution, and they were allowed to stand in a moist chamber at room temperature for 1 hour. Subsequently, a solution adjusted to comprise a monoclonal antibody against CAPRIN-1 having the heavy-chain variable region of SEQ ID NO: 78 and the light-chain variable region of SEQ ID NO: 79 at 10 μg/ml with a blocking solution, which reacts with the cancer cell surface prepared in Reference Example 1, was applied thereon, and the resultant was allowed to stand in a moist chamber at 4° C. overnight. After the glass slides were washed 3 times with PBS-T for 10 minutes, the MOM biotin-labeled anti-IgG antibody (VECTASTAIN) diluted 250-fold with a blocking solution was added and was then allowed to stand in a moist chamber at room temperature for 1 hour. After the slides were washed 3 times with PBS-T for 10 minutes, an avidin-biotin ABC reagent (VECTASTAIN) was applied thereon, and the slides were allowed to stand in a moist chamber at room temperature for 5 minutes. After the slides were washed 3 times with PBS-T for 10 minutes, a DAB color-developing solution (10 mg of DAB+10 μl of 30% $H_2O_2$/0.05 M Tris-HCl, pH 7.6, 50 ml) was applied thereon, and the slides were allowed to stand in a moist chamber at room temperature for 30 minutes. The slides were rinsed with distilled water, a hematoxylin reagent (DAKO) was applied thereon, and the slides were allowed to stand at room temperature for 1 minute, followed by rinsing with distilled water. The glass slides were successively dipped in 70%, 80%, 90%, 95%, and 100% ethanol solutions for 1 minute each and then allowed to stand in xylene overnight. The glass slides were removed, mounted with Glycergel Mounting Medium (DAKO), and then observed. As a result, weak CAPRIN-1 expression was observed within cells of the salivary gland, kidney, colon, and gastric tissues; however, expression thereof was not observed on cell surfaces, and no expression was observed in tissues derived from other organs.

(5)-2: CAPRIN-1 Expression in Canine Breast Cancer Tissue

The 108 frozen breast cancer tissue specimens of dogs, which had been diagnosed to have malignant breast cancer via pathological diagnosis, were used to prepare slides comprising frozen slices thereon and to carry out immunohistochemical staining with the use of a monoclonal antibody against CAPRIN-1 having the heavy-chain variable region of SEQ ID NO: 78 and the light-chain variable region of SEQ ID NO: 79 in the same manner as described above. As a result, CAPRIN-1 expression was observed in 100 of the 108 specimens (92.5%), and CAPRIN-1 expression was found to be particularly potent on the cancer cell surface with a high grade of atypism.

(5)-3: CAPRIN-1 Expression in Human Breast Cancer Tissue

Immunohistochemical staining was carried out on 188 breast cancer tissue specimens on the paraffin-embedded human breast cancer tissue array (BIOMAX). The human breast cancer tissue array was treated at 60° C. for 3 hours, the array was introduced into a staining jar filled with xylene, xylene was replaced with fresh xylene every 5 minutes, and this procedure was repeated 3 times. Subsequently, the similar procedures were repeated with the use of ethanol and PBS-T instead of xylene. The human breast cancer tissue array was introduced into a staining jar filled with 10 mM citrate buffer containing 0.05% Tween 20 (pH 6.0), the array was treated at 125° C. for 5 minutes, and the array was allowed to stand at room temperature for at least 40 minutes.

Extra moisture around the slices was wiped off using Kimwipes, the tissue was encircled with Dakopen, and an adequate amount of Peroxidase Block (DAKO) was added dropwise thereto. After the array was allowed to stand at room temperature for 5 minutes, the array was introduced into a staining jar filled with PBS-T, PBS-T was replaced with fresh PBS-T every 5 minutes, and this procedure was repeated 3 times. A PBS-T solution containing 10% FBS was applied thereon as a blocking solution, and it was allowed to stand in a moist chamber at room temperature for 1 hour. Subsequently, a solution adjusted to comprise a monoclonal antibody against CAPRIN-1 having the heavy-chain variable region of SEQ ID NO: 78 and the light-chain variable region of SEQ ID NO: 79 at 10 μg/ml with a PBS-T solution containing 5% FBS, which reacts with the cancer cell surface prepared in Reference Example 1, was applied thereon, and the array was allowed to stand in a moist chamber at 4° C. overnight. After the array was washed 3 times with PBS-T for 10 minutes, an adequate amount of the Peroxidase Labelled Polymer Conjugated (DAKO) was added dropwise thereto, and the array was then allowed to stand in a moist chamber at room temperature for 30 minutes. After the array was washed 3 times with PBS-T for 10 minutes, a DAB color-developing solution (DAKO) was applied thereon, the array was allowed to stand at room temperature for about 10 minutes, and the color-developing solution was discarded. The array was washed 3 times with PBS-T for 10 minutes, rinsed with distilled water, successively dipped in 70%, 80%, 90%, 95%, and 100% ethanol solutions for 1 minute each, and then allowed to stand in xylene overnight. The glass slides were removed, mounted with Glycergel Mounting Medium (DAKO), and then observed. As a result, potent CAPRIN-1 expression was observed in 138 of the entire 188 breast cancer tissue specimens (73%).

(5)-4: CAPRIN-1 Expression in Human Malignant Brain Tumor

Immunohistochemical staining was carried out on 247 malignant brain tumor tissue specimens on the paraffin-embedded human malignant brain tumor tissue array (BIOMAX), with a monoclonal antibody against CAPRIN-1 having the heavy-chain variable region of SEQ ID NO: 78 and the light-chain variable region of SEQ ID NO: 79 in the same manner as in (5)-3 above. As a result, potent CAPRIN-1 expression was observed in 227 of the entire 247 malignant brain tumor tissue specimens (92%). (5)-5: CAPRIN-1 expression in human breast cancer-metastasized lymph node Immunohistochemical staining was carried out on 150 breast cancer-metastasized lymph node tissue specimens on the paraffin-embedded human breast cancer-metastasized lymph node tissue array (BIOMAX), with a monoclonal antibody against CAPRIN-1 having the heavy-chain variable region of SEQ ID NO: 78 and the light-chain variable region of SEQ ID NO: 79 in the same manner as in (5)-3 above. As a result, potent CAPRIN-1 expression was observed in 136 of the entire 150 breast cancer-metastasized lymph node specimens (90%). CAPRIN-1 expression was found to be potent in cancer tissue metastasized from breast cancer.

Reference Example 1

Preparation of Monoclonal Antibody Against CAPRIN-1

100 μg of the antigen protein of SEQ ID NO: 2 prepared in Example 2 (human CAPRIN-1) was mixed with the equivalent amount of the MPL+TDM adjuvant (Sigma Corporation), and the mixture was used as an antigen solution per mouse. The antigen solution was administered intraperitoneally to 6-week-old Balb/c mice (Japan SLC, Inc.), and the solution was administered 3 more times every week. The spleen removed 3 days after the final immunization was sandwiched between two sterilized glass slides, grounded, washed with PBS(−) (Nissui), and centrifuged at 1,500 rpm for 10 minutes, and the supernatant was removed. This procedure was repeated 3 times to obtain spleen cells. The obtained spleen cells were mixed with the SP2/0 mouse myeloma cells (purchased from ATCC) at 10:1, a PEG solution prepared by mixing 200 μl of RPMI 1640 medium containing 10% FBS with 800 μl of PEG1500 (Boehringer) heated at 37° C. was added thereto, and the resultant was allowed to stand for 5 minutes to perform cell fusion. The resultant was centrifuged at 1,700 rpm for 5 minutes, the supernatant was removed, cells were suspended in 150 ml of RPMI 1640 medium containing 15% FBS to which 2% equivalents of a HAT solution (Gibco) had been added (HAT selection medium), and 100 μl each thereof was seeded per well of 15 96-well plates (Nunc). Culture was conducted for 7 days at 37° C. in 5% $CO_2$ to obtain hybridomas resulting from fusion of spleen cells with myeloma cells.

Hybridomas were selected using the binding affinity of the antibody produced by the resulting hybridomas to the CAPRIN-1 protein as the indicator. The CAPRIN-1 protein solution (1 μg/ml) prepared in Example 2 was added to the 96-well plate in amounts of 100 μl per well, and the plate was allowed to stand at 4° C. for 18 hours. Wells were washed 3 times with PBS-T, a 0.5% bovine serum albumin (BSA) solution (Sigma Corporation) was added in amounts of 400 μl per well, and the plate was allowed to stand at room temperature for 3 hours. The solution was removed, wells were washed 3 times with 400 μl of PBS-T per well, the culture supernatants of the hybridomas obtained above were added in amounts of 100 μl per well, and the plate was allowed to stand at room temperature for 2 hours. After wells were washed 3 times with PBS-T, the HRP-labeled anti-mouse IgG (H+L) antibody (Invitrogen) diluted 5,000-fold with PBS was added in amounts of 100 μl per well, and the plate was allowed to stand at room temperature for 1 hour. After wells were washed 3 times with PBS-T, a TMB substrate solution (Thermo) was added in amounts of 100 μl per well, and the plate was allowed to stand for 15 to 30 minutes to perform a color-developing reaction. After color was developed, 1N sulfuric acid was added in amounts of 100 μl per well to terminate the reaction, and the absorbance at 450 nm and that at 595 nm were assayed using an absorption spectrometer. As a result, a plurality of hybridomas producing antibodies with high absorbance values were selected.

The selected hybridomas were added to a 96-well plate in amounts of 0.5 cells per well and cultured. One week later, some hybridomas were observed to form single colonies in wells. The cells in such wells were further cultured, and hybridomas were selected using the binding affinity of antibodies produced from the cloned hybridomas to the CAPRIN-1 protein as the indicator. The CAPRIN-1 protein solution (1 μg/ml) prepared in Example 2 was added to a 96-well plate in amounts of 100 μl per well and the plate was allowed to stand at 4° C. for 18 hours. After the wells were washed 3 times with PBS-T, a 0.5% BSA solution was added in amounts of 400 μl per well, and the plate was allowed to stand at room temperature for 3 hours. The solution was removed, the wells were washed 3 times with 400 μl of PBS-T per well, the culture supernatants of the hybridomas obtained above were added in amounts of 100 μl per well, and the plate was allowed to stand at room temperature for 2 hours. After the wells were washed 3 times with PBS-T, the HRP-labeled anti-mouse IgG (H+L) antibody (Invitrogen) diluted 5,000-fold with PBS was added in amounts of 100 μl per well, and the plate was allowed to stand at room temperature for 1 hour. After the wells were washed 3 times with PBS-T, a TMB substrate solution (Thermo) was added in amounts of 100 μl per well, and the plate was allowed to stand for 15 to 30 minutes to perform a color-developing reaction. After color was developed, 1N sulfuric acid was added in amounts of 100 μl per well to terminate the reaction, and the absorbance at 450 nm and that at 595 nm were assayed using an absorption spectrometer. As a result, a plurality of hybridoma strains producing monoclonal antibodies showing reactivity with the CAPRIN-1 protein were obtained, the culture supernatant of hybridomas were purified using a protein G carrier to obtain 150 monoclonal antibodies binding to the CAPRIN-1 protein.

Subsequently, monoclonal antibodies having reactivity with the surfaces of the breast cancer cells expressing CAPRIN-1 were selected from among the above monoclonal antibodies. Specifically, $10^6$ cells of human breast cancer cell line, MDA-MB-231V, were centrifuged in a 1.5-ml micro centrifuge tube, 100 μl of the hybridoma supernatants prepared above was added thereto, and the resultants were allowed to stand on ice for 1 hour. After the plate was washed with PBS, the FITC-labeled goat anti-mouse IgG antibody (Invitrogen) diluted 500-fold with PBS containing 0.1% fetal bovine serum was added, and the plate was allowed to stand on ice for 1 hour. After the plate was washed with PBS, fluorescence intensity was measured using the FACSCalibur (Becton Dickinson). Separately, as a control, the same procedure was carried out except for adding a medium instead of the antibodies. As a result, 11 monoclonal antibodies exhibiting stronger fluorescence intensity than the control; i.e., 11 monoclonal antibodies reacting with the breast cancer cell surfaces, were selected. The sequence of the heavy-chain variable region of one of such monoclonal antibodies is shown by SEQ ID NO: 78 and that of the light-chain variable region thereof is shown by SEQ ID NO: 79.

Example 2

Preparation of Canine and Human Novel Cancer Antigen Proteins (1) Preparation of Recombinant Protein A recombinant protein was prepared using the gene of SEQ ID NO: 5 obtained in Example 1 in the manner described below. Reagents (the vector (1 μl) prepared from the phagemid solution obtained in Example 1 and subjected to sequence analysis, 0.4 μM each of two types of primers containing NdeI and KpnI restriction sites (SEQ ID NOs: 37 and 38), 0.2 mM of dNTPs, and 1.25 U of PrimeSTAR HS polymerase (Takara Shuzo Co., Ltd.)) were mixed with the accompanying buffer to be adjusted to match the total volume of 50 μl. The resultant was subjected to the reaction of 30 cycles at 98° C. for 10 seconds and 68° C. for 1.5 minutes using the Thermal Cycler (BIO RAD). The two above types of primers were used to amplify a region encoding the full-length amino acid sequence of SEQ ID NO: 6. After PCR was carried out, the amplified DNA was electrophoresed on 1% agarose gel, and a DNA fragment of about 1.4 kbp was purified using the QIAquick Gel Extraction Kit (QIAGEN).

The purified DNA fragment was ligated to the pCR-Blunt cloning vector (Invitrogen). The resultant was transformed into *E. coli*, the plasmid was recovered, and the amplified gene fragment was confirmed to match the sequence of interest via sequencing. The plasmid, which had been found to match the sequence of interest, was treated with the NdeI and KpnI restriction enzymes, the resultant was purified with the QIAquick Gel Extraction Kit, and the gene sequence of interest was inserted into an *E. coli* expression vector (pET30b, Novagen) treated with the NdeI and KpnI restriction enzymes. Use of this vector enables production of a His-tag-fused recombinant protein. The plasmid was transformed into *E. coli* BL21 (DE3) and induced with 1 mM IPTG to express the protein of interest in *E. coli*.

Separately, a recombinant protein of the canine homologous gene was prepared using the gene of SEQ ID NO: 7 in the manner described below. Reagents (cDNA (1 µl), expression of which was confirmed via RT-PCR among the tissue or cellular cDNA prepared in Example 1, 0.4 µM each of two types of primers containing NdeI and KpnI restriction sites (SEQ ID NOs: 39 and 40), 0.2 mM of dNTPs, and 1.25 U of PrimeSTAR HS polymerase (Takara Shuzo Co., Ltd.)) were mixed with an accompanying buffer to be adjusted to match the total volume of 50 µl. The resultant was subjected to the reaction of 30 cycles at 98° C. for 10 seconds and 68° C. for 2.5 minutes, using the Thermal Cycler (BIO RAD). The two above types of primers were used to amplify a region encoding the full-length amino acid sequence of SEQ ID NO: 8. After PCR was carried out, the amplified DNA was electrophoresed on 1% agarose gel, and a DNA fragment of about 2.2 kbp was purified using the QIAquick Gel Extraction Kit (QIAGEN).

The purified DNA fragment was ligated to the pCR-Blunt cloning vector (Invitrogen). The resultant was transformed into *E. coli*, the plasmid was recovered, and the amplified gene fragment was confirmed to match the sequence of interest via sequencing. The plasmid, which had been found to match the sequence of interest, was treated with the NdeI and KpnI restriction enzymes, the resultant was purified with the QIAquick Gel Extraction Kit, and the gene sequence of interest was inserted into an *E. coli* expression vector (pET30b, Novagen) treated with the NdeI and KpnI restriction enzymes. Use of this vector enables production of a His-tag-fused recombinant protein. The plasmid was transformed into *E. coli* BL21 (DE3) and induced with 1 mM IPTG to express the protein of interest in *E. coli*.

A recombinant protein of the human homologous gene was prepared using the gene of SEQ ID NO: 1 in the manner described below. Reagents (cDNA (1 µl), expression of which was confirmed via RT-PCR among the tissue or cellular cDNA prepared in Example 1, 0.4 µM each of two types of primers containing SacI and XhoI restriction sites (SEQ ID NOs: 41 and 42), 0.2 mM of dNTPs, and 1.25 U of PrimeSTAR HS polymerase (Takara Shuzo Co., Ltd.)) were mixed with an accompanying buffer to be adjusted to match the total volume of 50 µl. The resultant was subjected to the reaction of 30 cycles at 98° C. for 10 seconds and 68° C. for 2.5 minutes, using the Thermal Cycler (BIO RAD). The two above types of primers were used to amplify a region encoding the full-length amino acid sequence of SEQ ID NO: 2. After PCR was carried out, the amplified DNA was electrophoresed on 1% agarose gel, and a DNA fragment of about 2.1 kbp was purified using the QIAquick Gel Extraction Kit (QIAGEN).

The purified DNA fragment was ligated to the pCR-Blunt cloning vector (Invitrogen). The resultant was transformed into *E. coli*, the plasmid was recovered, and the amplified gene fragment was confirmed to match the sequence of interest via sequencing. The plasmid, which had been found to match the sequence of interest, was treated with the SacI and XhoI restriction enzymes, the resultant was purified with the QIAquick Gel Extraction Kit, and the gene sequence of interest was inserted into an *E. coli* expression vector (pET30a, Novagen) treated with the SacI and XhoI restriction enzymes. Use of this vector enables production of a His-tag-fused recombinant protein. The plasmid was transformed into *E. coli* BL21 (DE3) and induced with 1 mM IPTG to express the protein of interest in *E. coli*.

(2) Purification of Recombinant Protein

Recombinant *E. coli* cells expressing the gene of SEQ ID NO: 1, 5, or 7 obtained above were cultured in LB medium containing 30 µg/ml kanamycin at 37° C. until the absorbance at 600 nm became around 0.7, isopropyl-β-D-1-thiogalactopyranoside was added to a final concentration of 1 mM, and culture was conducted at 37° C. for 4 hours. Thereafter, the cells were centrifuged at 4,800 rpm for 10 minutes and harvested. The cell pellet was suspended in phophate-buffered physiological saline, the resultant was centrifuged at 4,800 rpm for an additional 10 minutes, and the cells were then washed.

The cells were suspended in phophate-buffered physiological saline and ultrasonically disrupted on ice. The solution of ultrasonically disrupted *E. coli* cells was centrifuged at 6,000 rpm for 20 minutes, the resulting supernatant was designated as a soluble fraction, and the precipitate was designated as an insoluble fraction.

The soluble fraction was added to a nickel-chelating column prepared in accordance with a conventional technique (carrier: Chelateing Sepharose™ Fast Flow (GE Health Care); column volume: 5 ml; equilibration buffer: 50 mM hydrochloride buffer, pH 8.0). An unadsorbed fraction was washed out with 10 column volumes of 50 mM hydrochloride buffer (pH 8.0) and 20 mM phosphate buffer containing 20 mM imidazole (pH 8.0), followed by elution with 6 bed volumes of 20 mM phosphate buffer containing 100 mM imidazole (pH 8.0) immediately thereafter. The fraction eluted with 20 mM phosphate buffer containing 100 mM imidazole (pH 8.0), in which elution of the protein of interest had been confirmed via. Coomassie staining, was added to a strong-anion-exchange column (carrier: Q Sepharose™ Fast Flow (GE Health Care); column volume: 5 ml; 20 mM phosphate buffer (pH 8.0) as an equilibration buffer). An unadsorbed fraction was washed out with 10 column volumes of 20 mM phosphate buffer (pH 7.0) and 20 mM phosphate buffer containing 200 mM sodium chloride (pH 7.0), followed by elution with 5 bed volumes of 20 mM phosphate buffer containing 400 mM sodium chloride (pH 7.0) immediately thereafter. The purified fractions of proteins each comprising the amino acid sequences shown by SEQ ID NOs: 2, 6, and 8 were obtained and then designated as materials for administration test.

A fraction (200 µl) of the purified samples obtained by the method described above was dispensed into 1 ml of a reaction buffer (20 mM Tris-HCl, 50 mM NaCl, 2 mM $CaCl_2$, pH 7.4), 2 µl of enterokinase (Novagen) was added, the resultant was allowed to stand at room temperature overnight, the reaction was allowed to proceed, a His tag was cleaved, and purification was then carried out using the Enterokinase Cleavage Capture Kit (Novagen) in accordance with the accompanying protocols. Subsequently, 1.2 ml of the purified sample obtained by the method described above was subjected to the buffer replacement with phosphate buffered saline (Nissui) via ultrafiltration using Nanosep 10K Omega (Pall), aseptic filtration was carried out through HT Tuffryn Acrodisc (pore size: 0.22 µm, Pall), and the resultant was used for the following experiment.

Example 3

Test of Administration of Recombinant Protein to Cancer-Bearing Dog (1) Antitumor Evaluation A cancer-bearing dog (breast cancer) having a tumor on the epidermis was subjected to evaluation of the antitumor effects of the recombinant protein purified above.

The recombinant polypeptide having the amino acid sequence shown by SEQ ID NO: 6 purified in the above-described manner (100 µg, 0.5 ml) was mixed with the equivalent amount of the Freund's incomplete adjuvant (Wako Pure Chemical Industries, Ltd.) to prepare a cancer therapeutic agent. The resulting agent was administered 3 times in total to the regional lymph node in the vicinity of the tumor, as an initial-administration, and 3 days and 7 days thereafter. As a result, a tumor about 86 mm$^3$ in size when the cancer therapeutic agent was administered shrank to 55 mm$^3$, 30 mm$^3$, and 20 mm$^3$ 10 days, 20 days, and 30 days after the initial administration, respectively.

A mixture of 0.5 ml of the recombinant polypeptide having the amino acid sequence shown by SEQ ID NO: 2 and 0.5 ml of the Freund's incomplete adjuvant was administered to another dog having breast cancer 3 times in total in the same manner as described above. Also, 100 μg of canine interleukin 12 was administered together with the agent subcutaneously. As a result, a tumor about 123 mm$^3$ in size when the cancer therapeutic agent was administered completely regressed 45 days after the initial administration of the cancer therapeutic agent.

Further, a mixture of 0.5 ml of the recombinant polypeptide having the amino acid sequence shown by SEQ ID NO: 8 and 0.5 ml of the Freund's incomplete adjuvant was administered to another dog having breast cancer 3 times in total in the same manner as described above. Also, 100 μg of canine interleukin 12 was administered together with the agent subcutaneously. As a result, a tumor about 96 mm$^3$ in size when the cancer therapeutic agent was administered completely regressed 27 days after the initial administration of the cancer therapeutic agent.

(2) Evaluation of Immunity-Inducing Capacity

The blood samples of the clinically affected dogs to which the recombinant polypeptides having the amino acid sequences shown by SEQ ID NO: 6, SEQ ID NO: 2, and SEQ ID NO: 8 had been administered in the administration test conducted in (1) above were obtained before administration and 10 days and 30 days after the initial administration, peripheral blood mononuclear cells were separated in accordance with a conventional technique, and the capacity of the recombinant proteins for immunity induction was evaluated via the ELISpot assay of IFNγ using the peripheral blood mononuclear cells.

70% ethanol was added to a 96-well plate (MultiScreen-IP, MAIPS4510, Millipore) in amounts of 100 μl/well, the plate was allowed to stand for 5 minutes, ethanol was aspirated off, the plate was washed with sterilized water, 200 mM sodium bicarbonate (pH 8.2) was added in amounts of 300 μl/well, the plate was allowed to stand for 5 minutes, sodium bicarbonate was aspirated off, and the plate was washed. Subsequently, the anti-canine interferon γ monoclonal antibody (clone142529, MAB781, R&D) added to 200 mM sodium bicarbonate was added to the plate in amounts of 0.5 μg/well, incubation was carried out at 37° C. overnight, and the primary antibody was solid-phased. After the primary antibody in the solution was aspirated off, a blocking solution (1% BSA-5% sucrose-200 mM sodium bicarbonate, pH 8.2) was added in amounts of 300 μl/well, and incubation was carried out at 4° C. overnight to block the plate. After the blocking solution was aspirated off, RPMI medium containing 10% fetal bovine serum (Invitrogen) was added in amounts of 300 μl/well, the plate was allowed to stand for 5 minutes, and the medium was aspirated off. Thereafter, canine peripheral blood mononuclear cells suspended in RPMI medium containing 10% fetal bovine serum were added to the plate in amounts of 5×10$^5$ cells/well, the dog-derived polypeptide or human-derived polypeptide used for administration were added thereto in amounts of 10 μl/well, and culture was conducted at 37° C. in 5% $CO_2$ for 24 hours to produce interferon γ from immunocytes among peripheral blood mononuclear cells. After culture was conducted, the medium was removed, and wells were washed 6 times with a wash (0.1% Tween 20-200 mM sodium bicarbonate, pH 8.2). The rabbit anti-dog polyclonal antibodies diluted 1.000-fold with the blocking solution were added to the plate in amounts of 100 μl/well and then incubated at 4° C. overnight. After the wells were washed 3 times with the wash, the HRP-labeled anti-rabbit antibodies diluted 1,000-fold with the blocking solution were added to the plate in amounts of 100 μl/well, and the reaction was allowed to proceed at 37° C. for 2 hours. After the wells were washed 3 times with the wash, a color was developed with the aid of a Konica immunostain (Konica), and the wells was washed with water to terminate the reaction. After the reaction was terminated, the membrane was dried, and the number of the developed spots was counted using the KS Elispot (Carl Zeiss). As a result, no spots were detected in the peripheral blood mononuclear cells of clinically affected dogs before polypeptide administration. In the case after polypeptides were administered, however, 13 and 82 spots were detected in the peripheral blood mononuclear cells obtained from the clinically affected dogs to which the recombinant polypeptide having the amino acid sequence shown by SEQ ID NO: 6 had been administered, 10 and 30 days after the administration. In the case of clinically affected dogs to which the recombinant polypeptide having the amino acid sequence shown by SEQ ID NO: 2 had been administered, 53 and 189 spots were detected in the peripheral blood mononuclear cells 10 and 30 days after the administration. In the case of clinically affected dogs to which the recombinant polypeptide having the amino acid sequence shown by SEQ ID NO: 8 had been administered, 32 and 117 spots were detected in the peripheral blood mononuclear cells 10 and 30 days after the administration.

The above results demonstrate that immunocytes that produce interferon γ specifically in response to the recombinant proteins that have been administered are induced in clinically affected dogs to which the recombinant polypeptide had been administered. The results also demonstrate that the immune reactions in which such immunocytes play a central role, produce the antitumor effects described in (1) above.

Example 4

Antitumor Effects of DNA Vaccines

A recombinant plasmid was prepared using the gene of SEQ ID NO: 19 in the following manner. Reagents (cDNA (1 μl) extracted in the same manner as in Example 1(4) from the mouse colorectal cancer cell line (CT26, purchased from ATCC) in which CAPRIN-1 expression had been observed, 0.4 μM each of two types of primers (shown by SEQ ID NOs: 80 and 81), 0.2 mM of dNTPs, and 1.25 U of PrimeSTAR HS polymerase) were mixed with an accompanying buffer to be adjusted to match the total volume of 50 μl. The resultant was subjected to PCR of 30 cycles at 98° C. for 10 seconds, 55° C. for 15 seconds, and 72° C. for 4 minutes, using a Thermal Cycler. The two above types of primers were used to amplify a region encoding the full-length amino acid sequence of SEQ ID NO: 20. After PCR was carried out, the amplified DNA was electrophoresed on 1% agarose gel, and a DNA fragment of about 2,100 by was purified using the QIAquick Gel Extraction Kit.

The purified DNA fragment was ligated to the pCR-Blunt cloning vector (Invitrogen). The resultant was transformed into E. coli, the plasmid was recovered, the sequence of the fragment was analyzed, and a plasmid having an amplified gene fragment matching with the sequence of interest was obtained. The plasmid was treated with the EcoRI restriction enzyme, the resultant was purified with the QIAquick Gel Extraction Kit, and the gene sequence of interest was inserted into a mammalian expression vector (pcDNA3.1, Invitrogen) treated with the EcoRI restriction enzyme in accordance with a conventional technique.

50 μg of gold particles (Bio Rad), 100 μl of spermidine (SIGMA), and 100 μl of 1M $CaCl_2$ were added to 100 μg of plasmid DNA prepared above, the mixture was agitated by a vortex, and the resultant was allowed to stand at room temperature for 10 minutes (hereafter referred to as "gold-DNA particles"). After the mixture was centrifuged at 3,000 rpm for 1 minute, the supernatant was discarded, and the particles were washed 3 times with 100% ethanol. 100% ethanol (6 ml) was added to the gold-DNA particles, the resultant was thoroughly agitated by a vortex, and the gold-DNA particles were introduced into the Tefzel Tubing (Bio Rad) and precipitated on the wall. Ethanol in the Tefzel Tubing to which the gold-DNA particles had adrered was air-dried, and the dried tube was cut in a length suitable for gene gun applications.

CT26 cells were transplanted subcutaneously into the dorsal regions of 20 Balb/c mice (Japan SLC, Inc.) in amounts of $10^6$ cells/mouse and grown to a tumor diameter of approximately 7 mm. Thereafter, the tube prepared above was fixed on the gene gun, the cells were percutaneously administered into the abdominal cavities of shaved mice at a pressure of 400 psi using a pure helium gas (the amount of plasmid DNA inoculated is 2 μg/mouse), and the antitumor effects were evaluated.

As a result, tumors became enlarged in 10 control mice to which empty plasmids comprising no CAPRIN-1 genes had been administered, and all the 10 mice died 63 days after tumor transplantation. In the case of 10 mice to which plasmids comprising the CAPRIN-1 genes inserted therein had been administered, however, tumors completely regressed by 25 days after tumor transplantation, and all mice remained alive 63 days after tumor transplantation when all control mice died.

Example 5

Induction of Peptide Epitope-Reactive CD8+ T Cells (1) Prediction of HLA-A0201-Binding Peptide Motif and HLA-A24-Binding Peptide Motif The amino acid sequence information of the human CAPRIN-1 polypeptide was obtained from the GenBank. In order to predict an HLA-A0201-binding peptide motif and an HLA-A24-binding peptide motif, the amino acid sequence of the human CAPRIN-1 polypeptide was analyzed via a computer prediction program using known BIMAS softwares (available at http://bimas.dcrt.nih.gov/molbio/hla_bind/), 29 types of peptides shown by SEQ ID NO: 43 to SEQ ID NO: 71 predicted to be capable of binding to the HLA-A0201 molecules and 5 types of peptides shown by SEQ ID NO: 72 to SEQ ID NO: 76 predicted to be capable of binding to the HLA-A24 molecules were selected.

(2) Induction of Peptide Epitope-Reactive CD8+ T Cells

The peripheral blood was separated from an HLA-A0201-positive healthy individual, overlaid on the lymphocyte separation medium (OrganonpTeknika, Durham, N.C.), and centrifuged at 1,500 rpm at room temperature for 20 minutes. A PBMC-containing fraction was recovered and washed 3 (or more) times in cold phosphate buffer to obtain peripheral blood mononuclear cells (PBMCs). The obtained PBMCs were suspended in 20 ml of AIM-V medium (Life Technologies) and adhered to a culture flask (Falcon) at 37° C. in 5% $CO_2$ for 2 hours. The nonadhered cells were used for T cell preparation, and the adhered cells were used for dendritic cell preparation.

The adhered cells were cultured in AIM-V medium in the presence of IL-4 (1,000 U/ml) and GM-CSF (1,000 U/ml). The medium was exchanged with another AIM-V medium to which IL-4 (1,000 U/ml), GM-CSF (1,000 U/ml), IL-6 (1,000 U/ml, Genzyme, Cambridge, Mass.), IL-1β (10 ng/ml, Genzyme, Cambridge, Mass.), and TNF-α (10 ng/ml, Genzyme, Cambridge, Mass.) had been added 6 days later, culture was conducted for an additional 2 days, and the obtained nonadhered cell population was used as dendritic cells.

The prepared dendritic cells were suspended in AIM-V medium at a cell density of $1 \times 10^6$ cells/ml, the peptides shown by SEQ ID NO: 43 to SEQ ID NO: 71 predicted to be capable of binding to the HLA-A0201 molecules selected in (1) above were added thereto at 10 μg/ml, and culture was conducted using a 96-well plate at 37° C. in 5% $CO_2$ for 4 hours. After culture was conducted, the cells were irradiated with X-rays (3,000 rad), washed with AIM-V medium, suspended in AIM-V medium containing 10% human AB serum (Nabi, Miami, Fla.), IL-6 (1,000 U/ml), and IL-12 (10 ng/ml, Genzyme, Cambridge, Mass.), and added to a 24-well plate in amounts of $1 \times 10^5$ cells/well. Further, the prepared T cell population was added in amounts of $1 \times 10^6$ cells/well and cultured at 37° C. in 5% $CO_2$. The culture supernatants were discarded 7 days later, the dendritic cells treated with peptides obtained in the above-described manner and then irradiated with X-rays were suspended in AIM-V medium containing 10% human AB serum (Nabi, Miami, Fla.), IL-7 (10 U/ml, Genzyme, Cambridge, Mass.), and IL-2 (10 U/ml, Genzyme, Cambridge, Mass.) (cell density: $1 \times 10^5$ cells/ml), the cells were added to a 24-well plate in amounts of $1 \times 10^5$ cells/well, and culture was further conducted. After such procedure was repeated 4 to 6 times every 7 days, the stimulated T cells were recovered, and CD8+ T cell induction was confirmed via flow cytometry.

Regarding the peptides of SEQ ID NO: 72 to SEQ ID NO: 76 predicted to be capable of binding to the HLA-A24 molecules, induction of peptide epitope-reactive CD8+ T cells was also attempted in the same manner as described above with the use of dendritic cells and T cell population induced from the peripheral blood of an HLA-A24-positive healthy individual.

As a negative control, a peptide having a sequence outside the scope of the present invention (SEQ ID NO: 77) was used.

Example 6

Figure 2:
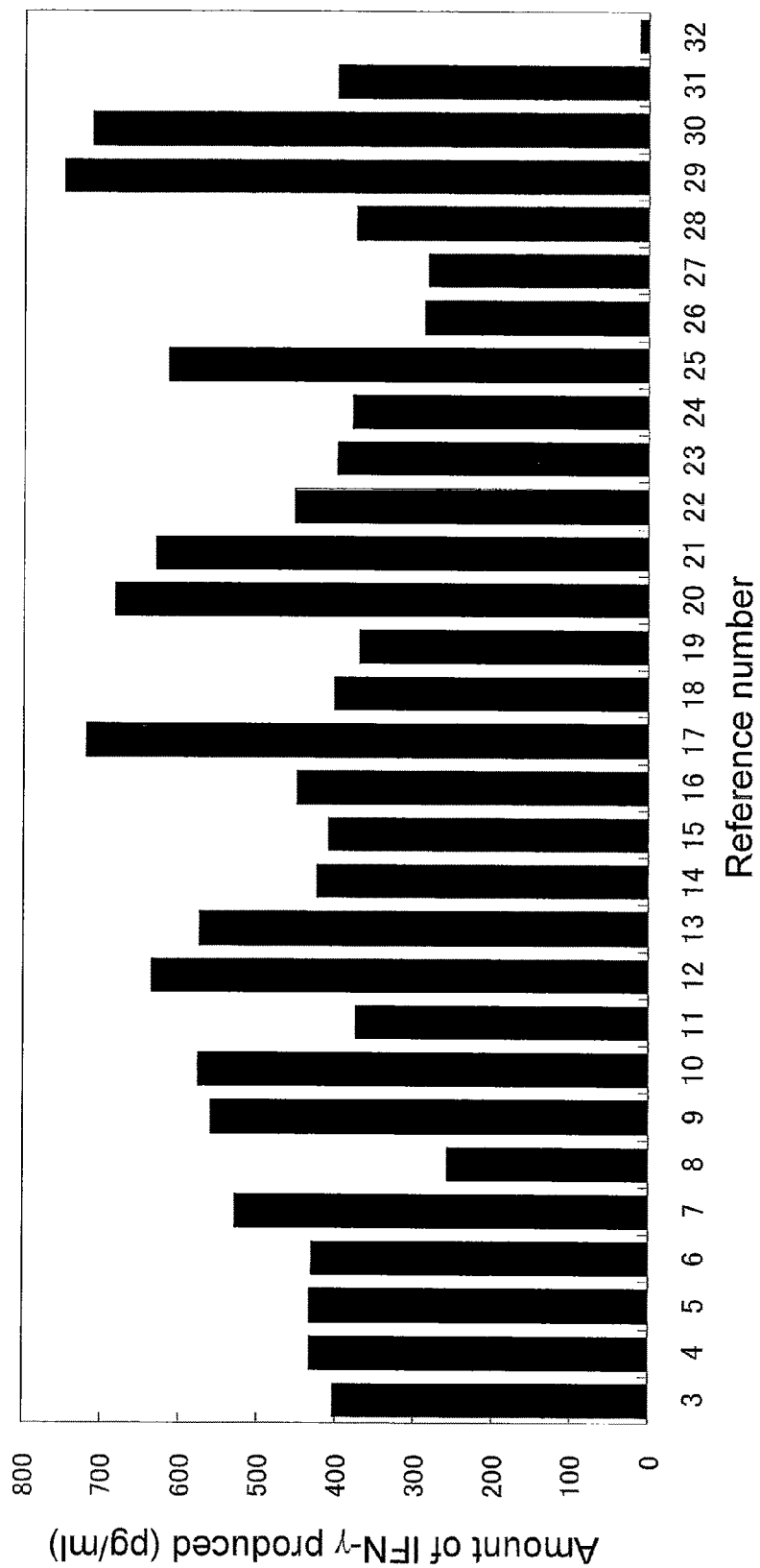
In FIG. 2, Reference numbers 3 to 31 on the horizontal axis each represent the capacity of HLA-A0201+ CD8+ T cells for producing IFN-γ stimulated by the T2 cells pulsed with the peptides of SEQ ID NOs: 43 to 71. Reference number 32 represents the results regarding a negative control peptide of SEQ ID NO: 77 (a peptide having a sequence outside the scope of the present invention).

Determination of Cytotoxic T Cell Antigen Epitope (1) Capacity for IFN-γ Production In order to determine the specificity of the T cells that had been observed to grow to peptide epitopes, among the T cells induced in Example 5(2), $5 \times 10^3$ T cells were added to $5 \times 10^4$ HLA-A0201 molecules-expressing T2 cells (Salter R D et al., Immunogenetics, 21: 235-246, 1985, T2 cells were purchased from ATCC) pulsed with the peptides predicted to be capable of binding to the HLA-A0201 molecules (the peptides were added to AIM-V medium at 10 μg/ml and cultured at 37° C. in 5% $CO_2$ for 4 hours), and the resultant was cultured on a 96-well plate in AIM-V medium containing 10% human AB serum for 24 hours. The supernatants were collected after culturing, and the amount of IFN-γ produced was measured via ELISA. As a result, IFN-γ production was observed more in the culture supernatants obtained from the wells in which T2 cells pulsed with the peptides of SEQ ID NO: 43 to SEQ ID NO: 71 were used than in the culture supernatants obtained from the wells in which T2 cells not pulsed with peptides were used (FIG. 2). The results demonstrate that the above peptides are T cell epitope peptides capable of specifically stimulating the proliferation of HLA-A0201+ CD8+ T cells to induce IFN-γ production.

Figure 3:
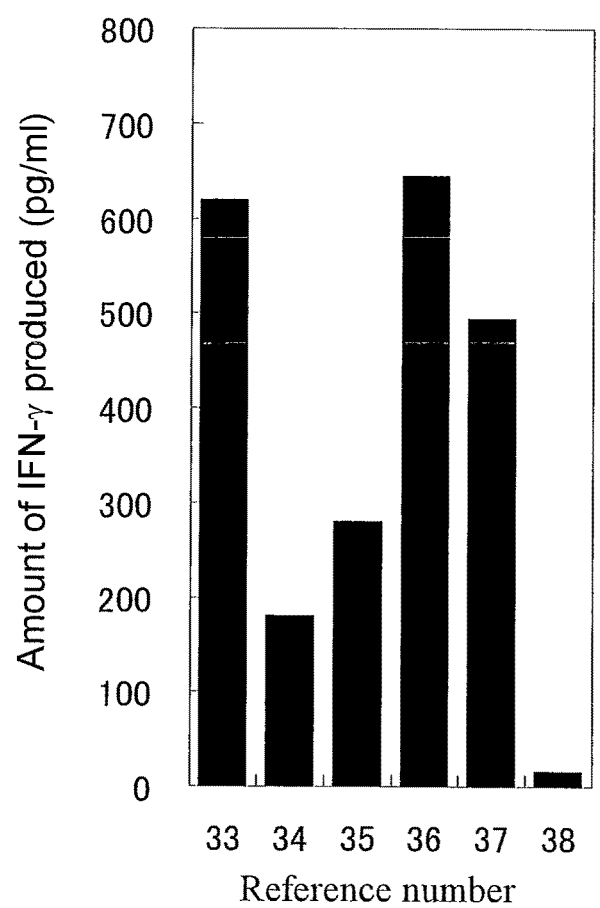
In FIG. 3, Reference numbers 33 to 37 on the horizontal axis each represent the capacity of the HLA-A24+ CD8+ T cells for producing IFN-γ stimulated by the JTK-LCL cells pulsed with the peptides of SEQ ID NOs: 72 to 76. Reference number 38 represents the results regarding a negative control of SEQ ID NO: 77.

In the same manner as described above, specificity of the peptide epitope-reactive CD8+ T cells induced with the use of the peptides of SEQ ID NO: 72 to SEQ ID NO: 76 in Example 5(2) to the peptide epitopes was determined in the following manner. Specifically, IFN-γ production level by the T cells against the peptide-pulsed JTK-LCL cells expressing the HLA-A24 molecules (the JTK-LCL cells were purchased from RIKEN, Japan) was measured via ELISA. As a result, IFN-γ production was observed more in the culture supernatants obtained from the wells in which JTK-LCL cells pulsed with the peptides of SEQ ID NO: 72 to SEQ ID NO: 76 were used than in the culture supernatants obtained from the wells in which JTK-LCLcells not pulsed with peptides were used (FIG. 3). The results demonstrate that the peptides of SEQ ID NO: 72 to SEQ ID NO: 76 are T cell epitope peptides capable of specifically stimulating the proliferation of HLA-A24+ CD8+ T cells to induce IFN-γ production.

(2) Cytotoxicity Evaluation

Figure 4:
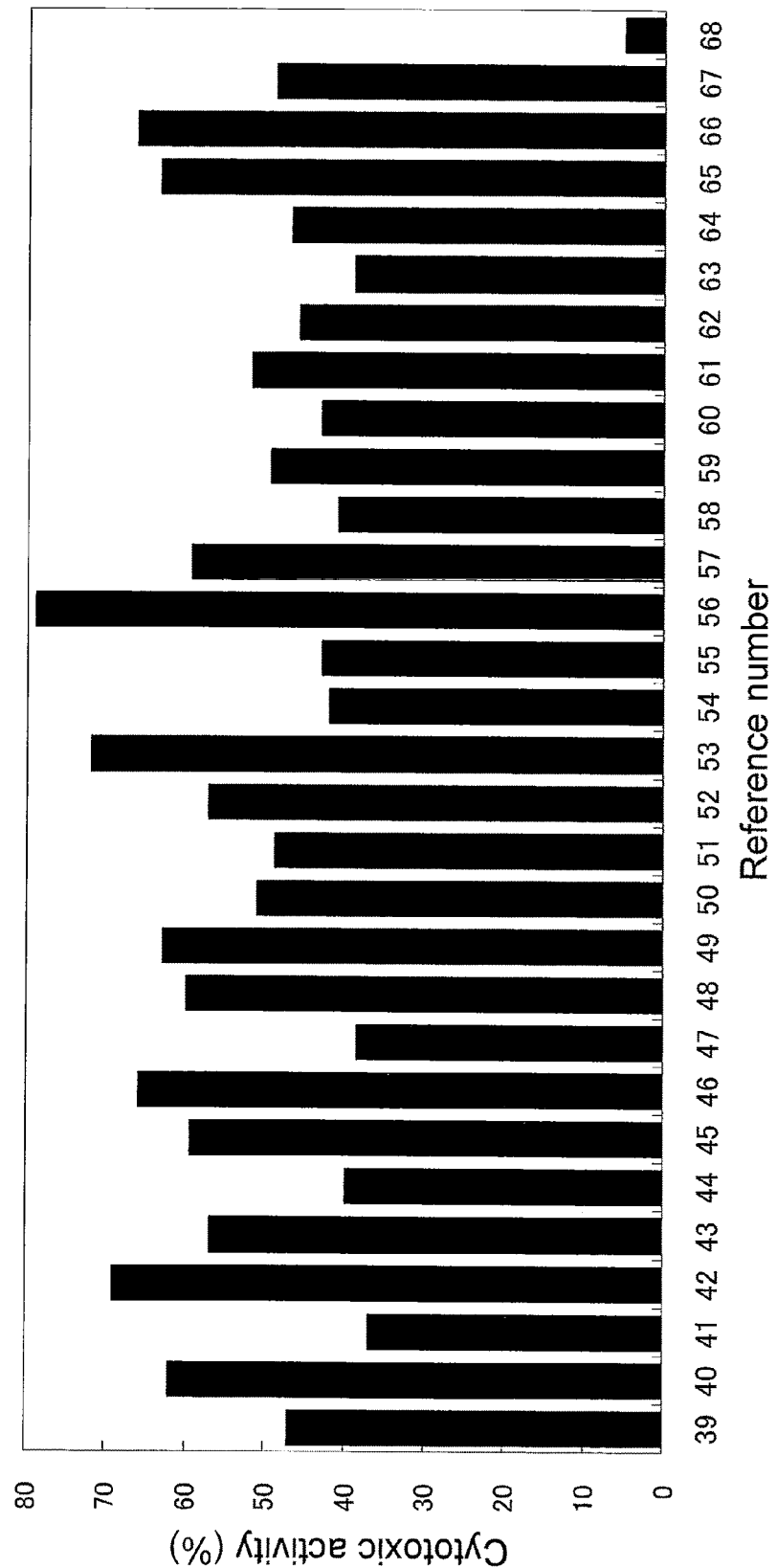
In FIG. 4, Reference numbers 39 to 67 on the horizontal axis each represent the cytotoxic activity of the HLA-A0201+ CD8+ T cells stimulated with the use of the peptides of SEQ ID NOs: 43 to 71 on the U-87MG cells. Reference number 68 represents the cytotoxic activity of the CD8+ T cells induced with the use of a negative control peptide (SEQ ID NO: 77).

Subsequently, whether or not peptides of SEQ ID NO: 43 to SEQ ID NO: 71 used in the present invention were presented on the HLA-A0201 molecules on the HLA-A0201+ tumor cells expressing the human CAPRIN-1 polypeptide and whether or not the CD8+ T cells stimulated with the peptides were capable of destroying the HLA-A0201+ tumor cells expressing the human CAPRIN-1 polypeptide were examined. $10^6$ cells of U-87MG human glioma cells (purchased from ATCC), which were verified to express the human CAPRIN-1 polypeptide, were collected in a 50-ml centrifuge tube, 100 μCi chromium-51 was added, and incubation was carried out at 37° C. for 2 hours. Thereafter, the cells were washed 3 times with RPMI medium (Gibco) containing 10% fetal bovine serum (hereafter referred to as "FBS," Gibco) and added to a 96-well V-bottom plate in amounts of $10^3$ cells/well. Further, $5\times10^4$ HLA-A0201+ and peptide epitope-reactive CD8+ T cells stimulated with the peptides suspended in RPMI medium containing 10% FBS were added, and culture was conducted at 37° C. in 5% $CO_2$ for 4 hours. After the culture, the amount of chromium-51 in the culture supernatant released from the disrupted tumor cells was measured to determine the cytotoxic activity of the peptide-stimulated CD8+ T cells. As a result, the peptide-stimulated HLA-A0201+ CD8+ T cells were found to have cytotoxic activity against U-87MG cells (FIG. 4). In contrast, the CD8+ T cells induced with the use of a negative control peptide (SEQ ID NO: 77) did not show cytotoxic activity. Thus, the peptides used in the present invention (i.e., peptides of SEQ ID NO: 43 to SEQ ID NO: 71) were found to be presented on the HLA-A0201 molecules on the HLA-A0201+ tumor cells expressing the human CAPRIN-1 polypeptide. Further, the peptides were also found to be capable of inducing CD8+ cytotoxic T cells that could disrupt such tumor cells.

Figure 5:
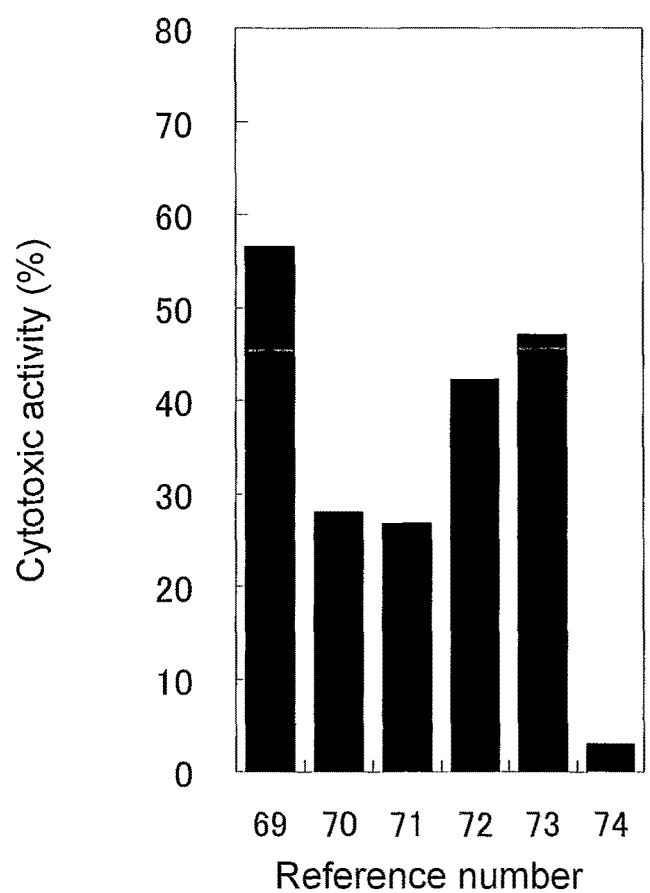
In FIG. 5, Reference numbers 69 to 73 on the horizontal axis each represent the cytotoxic activity of the HLA-A24+ CD8+ T cells stimulated with the use of the peptides of SEQ ID NOs: 72 to 76 on the JTK-LCL cells. Reference number 74 represents the cytotoxic activity of the CD8+ T cells induced with the use of a negative control peptide (SEQ ID NO: 77).

Subsequently, whether or not peptides of SEQ ID NO: 72 to SEQ ID NO: 76 were presented on the HLA-A24 molecules on the HLA-A24+ tumor cells expressing the human CAPRIN-1 polypeptide and whether or not the CD8+ T cells stimulated with the peptides were capable of disrupting the HLA-A24+ tumor cells expressing the human CAPRIN-1 polypeptide were examined in the same manner as described above. Chromium-51 was incorporated into the HLA-A24+ JTK-LCL cells expressing the human CAPRIN-1 polypeptide, HLA-A24+ and peptide epitope-reactive. CD8+ T cells were added, culture was conducted, and the amount of chromium-51 in the culture supernatant released from the disrupted cells was measured. As a result, the HLA-A24+ CD8+ T cells stimulated with the peptides of SEQ ID NO: 72 to SEQ ID NO: 76 were found to have the cytotoxic activity against the JTK-LCL cells (FIG. 5). Thus, the peptides of SEQ ID NO: 72 to SEQ ID NO: 76 were found to be presented on the HLA-A24 molecules on the HLA-A24+ cells expressing the human CAPRIN-1 polypeptide, and the peptides were found to be capable of inducing CD8+ cytotoxic T cells capable of disrupting such cells. The CD8+ T cells induced with the use of a negative control peptide (SEQ ID NO: 77) did not exhibit cytotoxicity.

In order to determine the cytotoxic activity, $5\times10^4$ CD8+ T cells stimulated and induced by the peptides used in the present invention were mixed with $10^3$ U-87MG or JTK-LCL cells into which chromium-51 had been incorporated, cultured for 4 hours, and the amount of chromium-51 released into the medium after culture was measured. The cytotoxic activity used herein means the cytotoxic activity of the CD8+ T cells against the U-87MG cells or the JTK-LCL cells (i.e., target cells) determined according to the following equation*.

Cytotoxic activity (%)=amount of chromium-51 released from U-87MG or JTK-LCL cell upon addition of CD8+ T cell/amount of chromium-51 released from target cell upon addition of 1N hydrochloric acid×100     Equation*

INDUSTRIAL APPLICABILITY

The present invention is industrially useful for the purpose of treatment and prevention of cancer.

This description includes part or all of the disclosure of the description and/or drawings of Japanese Patent Application No. 2008-202065, to which the present application claims the priority. Also, all publications, patents, and patent applications cited herein are incorporated herein by reference in their entirety.

Sequence Listing Free Text
SEQ ID NO: 31: T3 primer
SEQ ID NO: 32: T7 primer
SEQ ID NOs: 33 to 34: primers
SEQ ID NOs: 35 to 36: GAPDH primers
SEQ ID NOs: 37 to 42 and 80 to 81: primers

The invention claimed is:

1. A method for inducing immunity comprising administering to an individual at least one polypeptide having immunity-inducing activity and selected from the following polypeptides (a) to (c), or a recombinant vector comprising a polynucleotide encoding said polypeptide and capable of expressing said polypeptide in vivo:

(a) a polypeptide of the amino acid sequence shown by SEQ ID NO: 60;

(b) a polypeptide having 85% or more sequence identity with the polypeptide (a); and (c) a polypeptide of 8 to 12 amino acids comprising the polypeptide (a) or (b).

2. The method according to claim 1, wherein one or plural types of said polypeptides are administered.

3. The method according to claim 2, wherein the polypeptide is an agent for treating an antigen-presenting cell.

4. The method according to claim 1, wherein said individual is an animal in need of treatment for cancer.

5. The method according to claim 4, wherein the cancer is selected from breast cancer, brain tumor, leukemia, lymphoma, lung cancer, esophagus cancer, or colorectal cancer.

6. The method according to claim 4, wherein the animal is a human, dog, or cat.

7. The method according to claim 1, wherein said method further comprises administering an immunopotentiating agent.

8. The method according to claim 7, wherein the immunopotentiating agent is at least one adjuvant or cytokine selected from the group consisting of Freund's incomplete adjuvant, Montanide, poly IC and a derivative thereof, CpG oligonucleotide, interleukin 12, interleukin 18, interferon $\alpha$, interferon $\beta$, interferon $\omega$, interferon $\gamma$, and Flt3 ligand.

* * * * *

SEQUENCE LISTING

<160> NUMBER OF SEQ ID NOS: 81

<210> SEQ ID NO 1
<211> LENGTH: 5562
<212> TYPE: DNA

<213> ORGANISM: Homo sapiens
<220> FEATURE:
<221> NAME/KEY: CDS
<222> LOCATION: (190)..(2319)
<223> OTHER INFORMATION:

<400> SEQUENCE: 1

```
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccacccttg cccctcagc tgcccactcg tgatttccag cggcctccgc     180 gcgcgcacg atg ccc tcg gcc acc agc cac agc ggg agc ggc agc aag tcg    231
           Met Pro Ser Ala Thr Ser His Ser Gly Ser Gly Ser Lys Ser
           1               5                  10 tcc gga ccg cca ccg ccg tcg ggt tcc tcc ggg agt gag gcg gcc gcg       279
Ser Gly Pro Pro Pro Pro Ser Gly Ser Ser Gly Ser Glu Ala Ala Ala
15                  20                  25                  30 gga gcc ggg gcc gcc gcg ccg gct tct cag cac ccc gca acc ggc acc       327
Gly Ala Gly Ala Ala Ala Pro Ala Ser Gln His Pro Ala Thr Gly Thr
                35                  40                  45 ggc gct gtc cag acc gag gcc atg aag cag att ctc ggg gtg atc gac       375
Gly Ala Val Gln Thr Glu Ala Met Lys Gln Ile Leu Gly Val Ile Asp
        50                  55                  60 aag aaa ctt cgg aac ctg gag aag aaa aag ggt aag ctt gat gat tac       423
Lys Lys Leu Arg Asn Leu Glu Lys Lys Lys Gly Lys Leu Asp Asp Tyr
    65                  70                  75 cag gaa cga atg aac aaa ggg gaa agg ctt aat caa gat cag ctg gat       471
Gln Glu Arg Met Asn Lys Gly Glu Arg Leu Asn Gln Asp Gln Leu Asp
80                  85                  90 gcc gtt tct aag tac cag gaa gtc aca aat aat ttg gag ttt gca aaa       519
Ala Val Ser Lys Tyr Gln Glu Val Thr Asn Asn Leu Glu Phe Ala Lys
95                 100                 105                 110 gaa tta cag agg agt ttc atg gca cta agt caa gat att cag aaa aca       567
Glu Leu Gln Arg Ser Phe Met Ala Leu Ser Gln Asp Ile Gln Lys Thr
                115                 120                 125 ata aag aag aca gca cgt cgg gag cag ctt atg aga gaa gaa gct gaa       615
Ile Lys Lys Thr Ala Arg Arg Glu Gln Leu Met Arg Glu Glu Ala Glu
        130                 135                 140 cag aaa cgt tta aaa act gta ctt gag cta cag tat gtt ttg gac aaa       663
Gln Lys Arg Leu Lys Thr Val Leu Glu Leu Gln Tyr Val Leu Asp Lys
    145                 150                 155 ttg gga gat gat gaa gtg cgg act gac ctg aaa caa ggt ttg aat gga       711
Leu Gly Asp Asp Glu Val Arg Thr Asp Leu Lys Gln Gly Leu Asn Gly
160                 165                 170 gtg cca ata ttg tcc gaa gag gag ttg tca ttg ttg gat gaa ttc tat       759
Val Pro Ile Leu Ser Glu Glu Glu Leu Ser Leu Leu Asp Glu Phe Tyr
175                 180                 185                 190 aag cta gta gac cct gaa cgg gac atg agc ttg agg ttg aat gaa cag       807
Lys Leu Val Asp Pro Glu Arg Asp Met Ser Leu Arg Leu Asn Glu Gln
                195                 200                 205 tat gaa cat gcc tcc att cac ctg tgg gac ctg ctg gaa ggg aag gaa       855
Tyr Glu His Ala Ser Ile His Leu Trp Asp Leu Leu Glu Gly Lys Glu
        210                 215                 220 aaa cct gta tgt gga acc acc tat aaa gtt cta aag gaa att gtt gag       903
Lys Pro Val Cys Gly Thr Thr Tyr Lys Val Leu Lys Glu Ile Val Glu
    225                 230                 235 cgt gtt ttt cag tca aac tac ttt gac agc acc cac aac cac cag aat       951
Arg Val Phe Gln Ser Asn Tyr Phe Asp Ser Thr His Asn His Gln Asn
240                 245                 250 ggg ctg tgt gag gaa gaa gag gca gcc tca gca cct gca gtt gaa gac       999
Gly Leu Cys Glu Glu Glu Glu Ala Ala Ser Ala Pro Ala Val Glu Asp
```

```
                  255                 260                 265                 270 cag gta cct gaa gct gaa cct gag cca gca gaa gag tac act gag caa       1047
Gln Val Pro Glu Ala Glu Pro Glu Pro Ala Glu Glu Tyr Thr Glu Gln
                    275                 280                 285 agt gaa gtt gaa tca aca gag tat gta aat aga cag ttc atg gca gaa       1095
Ser Glu Val Glu Ser Thr Glu Tyr Val Asn Arg Gln Phe Met Ala Glu
                    290                 295                 300 aca cag ttc acc agt ggt gaa aag gag cag gta gat gag tgg aca gtt       1143
Thr Gln Phe Thr Ser Gly Glu Lys Glu Gln Val Asp Glu Trp Thr Val
                    305                 310                 315 gaa acg gtt gag gtg gta aat tca ctc cag cag caa cct cag gct gca       1191
Glu Thr Val Glu Val Val Asn Ser Leu Gln Gln Gln Pro Gln Ala Ala
                    320                 325                 330 tcc cct tca gta cca gag ccc cac tct ttg act cca gtg gct cag gca       1239
Ser Pro Ser Val Pro Glu Pro His Ser Leu Thr Pro Val Ala Gln Ala
335                 340                 345                 350 gat ccc ctt gtg aga aga cag cga gta caa gac ctt atg gca caa atg       1287
Asp Pro Leu Val Arg Arg Gln Arg Val Gln Asp Leu Met Ala Gln Met
                    355                 360                 365 cag ggt ccc tat aat ttc ata cag gat tca atg ctg gat ttt gaa aat       1335
Gln Gly Pro Tyr Asn Phe Ile Gln Asp Ser Met Leu Asp Phe Glu Asn
                    370                 375                 380 cag aca ctt gat cct gcc att gta tct gca cag cct atg aat cca aca       1383
Gln Thr Leu Asp Pro Ala Ile Val Ser Ala Gln Pro Met Asn Pro Thr
                    385                 390                 395 caa aac atg gac atg ccc cag ctg gtt tgc cct cca gtt cat tct gaa       1431
Gln Asn Met Asp Met Pro Gln Leu Val Cys Pro Pro Val His Ser Glu
                    400                 405                 410 tct aga ctt gct cag cct aat caa gtt cct gta caa cca gaa gcg aca       1479
Ser Arg Leu Ala Gln Pro Asn Gln Val Pro Val Gln Pro Glu Ala Thr
415                 420                 425                 430 cag gtt cct ttg gta tca tcc aca agt gag ggg tac aca gca tct caa       1527
Gln Val Pro Leu Val Ser Ser Thr Ser Glu Gly Tyr Thr Ala Ser Gln
                    435                 440                 445 ccc ttg tac cag cct tct cat gct aca gag caa cga cca cag aag gaa       1575
Pro Leu Tyr Gln Pro Ser His Ala Thr Glu Gln Arg Pro Gln Lys Glu
                    450                 455                 460 cca att gat cag att cag gca aca atc tct tta aat aca gac cag act       1623
Pro Ile Asp Gln Ile Gln Ala Thr Ile Ser Leu Asn Thr Asp Gln Thr
                    465                 470                 475 aca gca tca tca tcc ctt cct gct gcg tct cag cct caa gta ttt cag       1671
Thr Ala Ser Ser Ser Leu Pro Ala Ala Ser Gln Pro Gln Val Phe Gln
                    480                 485                 490 gct ggg aca agc aaa cct tta cat agc agt gga atc aat gta aat gca       1719
Ala Gly Thr Ser Lys Pro Leu His Ser Ser Gly Ile Asn Val Asn Ala
495                 500                 505                 510 gct cca ttc caa tcc atg caa acg gtg ttc aat atg aat gcc cca gtt       1767
Ala Pro Phe Gln Ser Met Gln Thr Val Phe Asn Met Asn Ala Pro Val
                    515                 520                 525 cct cct gtt aat gaa cca gaa act tta aaa cag caa aat cag tac cag       1815
Pro Pro Val Asn Glu Pro Glu Thr Leu Lys Gln Gln Asn Gln Tyr Gln
                    530                 535                 540 gcc agt tat aac cag agc ttt tct agt cag cct cac caa gta gaa caa       1863
Ala Ser Tyr Asn Gln Ser Phe Ser Ser Gln Pro His Gln Val Glu Gln
                    545                 550                 555 aca gag ctt cag caa gaa cag ctt caa aca gtg gtt ggc act tac cat       1911
Thr Glu Leu Gln Gln Glu Gln Leu Gln Thr Val Val Gly Thr Tyr His
                    560                 565                 570 ggt tcc cca gac cag tcc cat caa gtg act ggt aac cac cag cag cct       1959
Gly Ser Pro Asp Gln Ser His Gln Val Thr Gly Asn His Gln Gln Pro
```

-continued

| | | | |
|---|---|---|---|
| 575 | 580 | 585 | 590 |

| | |
|---|---|
| cct cag cag aac act gga ttt cca cgt agc aat cag ccc tat tac aat<br>Pro Gln Gln Asn Thr Gly Phe Pro Arg Ser Asn Gln Pro Tyr Tyr Asn<br>                  595                    600                    605 | 2007 |
| agt cgt ggt gtg tct cgt gga ggc tcc cgt ggt gct aga ggc ttg atg<br>Ser Arg Gly Val Ser Arg Gly Gly Ser Arg Gly Ala Arg Gly Leu Met<br>        610                    615                    620 | 2055 |
| aat gga tac cgg ggc cct gcc aat gga ttc aga gga gga tat gat ggt<br>Asn Gly Tyr Arg Gly Pro Ala Asn Gly Phe Arg Gly Gly Tyr Asp Gly<br>              625                    630                    635 | 2103 |
| tac cgc cct tca ttc tct aac act cca aac agt ggt tat aca cag tct<br>Tyr Arg Pro Ser Phe Ser Asn Thr Pro Asn Ser Gly Tyr Thr Gln Ser<br>        640                    645                    650 | 2151 |
| cag ttc agt gct ccc cgg gat tac tct ggc tat caa cgg gat gga tat<br>Gln Phe Ser Ala Pro Arg Asp Tyr Ser Gly Tyr Gln Arg Asp Gly Tyr<br>655                    660                    665                    670 | 2199 |
| cag cag aat ttc aag cga ggc tct ggg cag agt gga cca cgg gga gcc<br>Gln Gln Asn Phe Lys Arg Gly Ser Gly Gln Ser Gly Pro Arg Gly Ala<br>                  675                    680                    685 | 2247 |
| cca cga ggt cgt gga ggg ccc cca aga ccc aac aga ggg atg ccg caa<br>Pro Arg Gly Arg Gly Gly Pro Pro Arg Pro Asn Arg Gly Met Pro Gln<br>        690                    695                    700 | 2295 |
| atg aac act cag caa gtg aat taa tctgattcac aggattatgt ttaatcgcca<br>Met Asn Thr Gln Gln Val Asn<br>        705 | 2349 |
| aaaacacact ggccagtgta ccataatatg ttaccagaag agttattatc tatttgttct | 2409 |
| cccttttcagg aaacttattg taaagggact gttttcatcc cataaagaca ggactacaat | 2469 |
| tgtcagcttt ctattacctg gatatggaag gaaactattt ttactctgca tgttctgtcc | 2529 |
| taagcgtcat cttgagcctt gcacatgata ctcagattcc tcacccttgc ttaggagtaa | 2589 |
| aacaatatac tttacagggt gataataatc tccatagtta tttgaagtgg cttgaaaaag | 2649 |
| gcaagattga cttttatgac attggataaa atctacaaat cagccctcga gttattcaat | 2709 |
| gataactgac aaactaaatt atttccctag aaaggaagat gaaaggagtg gagtgtggtt | 2769 |
| tggcagaaca actgcatttc acagcttttc cagttaaatt ggagcactga acgttcagat | 2829 |
| gcataccaaa ttatgcatgg gtcctaatca cacatataag gctggctacc agctttgaca | 2889 |
| cagcactgtt catctggcca aacaactgtg gttaaaaaca catgtaaaat gcttttaac | 2949 |
| agctgatact gtataagaca aagccaagat gcaaaattag ctttgattg cacttttg | 3009 |
| aaaaatatgc aacaaatatg ggatgtaatc cggatggccg cttctgtact taatgtgaaa | 3069 |
| tatttagata ccttttgaa cacttaacag tttctttgag acaatgactt tgtaaggat | 3129 |
| tggtactatc tatcattcct tatgacatgt acattgtctg tcactaatcc ttggatttg | 3189 |
| ctgtattgtc acctaaattg gtacaggtac tgatgaaaat ctcagtgga taatcataac | 3249 |
| actctcggtc acatgttttt ccttcagctt gaaagctttt ttttaaaagg aaagatacc | 3309 |
| aaatgcctgc tgctaccacc cttttcaatt gctatctttt gaaaggcacc agtatgtgtt | 3369 |
| ttagattgat ttccctgttt cagggaaatc acgacagta gtttcagttc tgatggtata | 3429 |
| agcaaaacaa ataaaacgtt tataaaagtt gtatcttgaa acactggtgt tcaacagcta | 3489 |
| gcagcttatg tgattcaccc catgccacgt tagtgtcaca aattttatgg tttatctcca | 3549 |
| gcaacatttc tctagtactt gcacttatta tctttttgtct aatttaacct taactgaatt | 3609 |
| ctccgtttct cctggaggca tttatattca gtgataattc cttcccttag atgcataggg | 3669 |
| agagtctcta aatttgatgg aaatggacac ttgagtagtg acttagcctt atgtactctg | 3729 |

```
ttggaatttg tgctagcagt ttgagcacta gttctgtgtg cctaggaagt taatgctgct    3789
tattgtctca ttctgacttc atggagaatt aatcccacct ttaagcaaag gctactaagt    3849
taatggtatt ttctgtgcag aaattaaatt ttatttcag catttagccc aggaattctt     3909
ccagtaggtg ctcagctatt taaaaacaaa actattctca acattcatc attagacaac     3969
tggagttttt gctggttttg taacctacca aaatggatag gctgttgaac attccacatt    4029
caaaagtttt gtagggtggt gggaaatggg ggatcttcaa tgtttatttt aaaataaaat    4089
aaaataagtt cttgactttt ctcatgtgtg gttgtggtac atcatattgg aagggttaac    4149
ctgttacttt ggcaaatgag tatttttttg ctagcacctc cccttgcgtg ctttaaatga    4209
catctgcctg ggatgtacca caaccatatg ttacctgtat cttaggggaa tggataaaat    4269
atttgtggtt tactgggtaa tccctagatg atgtatgctt gcagtcctat ataaaactaa    4329
atttgctatc tgtgtagaaa ataatttcat gacatttaca atcaggactg aagtaagttc    4389
ttcacacagt gacctctgaa tcagtttcag agaagggatg ggggagaaaa tgccttctag    4449
gttttgaact tctatgcatt agtgcagatg ttgtgaatgt gtaaaggtgt tcatagtttg    4509
actgtttcta tgtatgtttt ttcaaagaat tgttccttt tttgaactat aattttctt      4569
tttttggtta ttttaccatc acagtttaaa tgtatatctt ttatgtctct actcagacca    4629
tatttttaaa ggggtgcctc attatggggc agagaacttt tcaataagtc tcattaagat    4689
ctgaatcttg gttctaagca ttctgtataa tatgtgattg cttgtcctag ctgcagaagg    4749
ccttttgttt ggtcaaatgc atattttagc agagtttcaa ggaaatgatt gtcacacatg    4809
tcactgtagc ctcttggtgt agcaagctca catacaaaat acttttgtat atgcataata    4869
taaatcatct catgtggata tgaaacttct ttttaaaac ttaaaaggt agaatgttat      4929
tgattacctt gattagggca gttttatttc cagatcctaa taattcctaa aaaatatgga    4989
aaagttttt ttcaatcatt gtaccttgat attaaaacaa atatcctta agtatttcta      5049
atcagttagc ttctacagtt cttttgtctc cttttatatg cagctcttac gtgggagact    5109
tttccactta aaggagacat agaatgtgtg cttattctca gaaggttcat taactgaggt    5169
gatgagttaa caactagttg agcagtcagc ttcctaagtg ttttaggaca tttgttcatt    5229
atattttccg tcatataact agaggaagtg gaatgcagat aagtgccgaa ttcaaaccct    5289
tcattttatg tttaagctcc tgaatctgca ttccacttgg gttgttttta agcattctaa    5349
atttagttg attataagtt agatttcaca gaatcagtat tgcccttgat cttgtccttt     5409
ttatggagtt aacggggagg aagacccctc aggaaaacga aagtaaattg ttaaggctca    5469
tcttcatacc ttttccatt ttgaatccta caaaaatact gcaaagact agtgaatgtt      5529
taaaattaca ctagattaaa taatatgaaa gtc                                 5562
```

<210> SEQ ID NO 2
<211> LENGTH: 709
<212> TYPE: PRT
<213> ORGANISM: Homo sapiens

<400> SEQUENCE: 2

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys

```
            50                  55                  60
Leu Arg Asn Leu Glu Lys Lys Gly Lys Leu Asp Asp Tyr Gln Glu
 65                  70                  75                  80

Arg Met Asn Lys Gly Glu Arg Leu Asn Gln Asp Gln Leu Asp Ala Val
                 85                  90                  95

Ser Lys Tyr Gln Glu Val Thr Asn Asn Leu Glu Phe Ala Lys Glu Leu
                100                 105                 110

Gln Arg Ser Phe Met Ala Leu Ser Gln Asp Ile Gln Lys Thr Ile Lys
            115                 120                 125

Lys Thr Ala Arg Arg Glu Gln Leu Met Arg Glu Ala Glu Gln Lys
130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
                180                 185                 190

Val Asp Pro Glu Arg Asp Met Ser Leu Arg Leu Asn Glu Gln Tyr Glu
                195                 200                 205

His Ala Ser Ile His Leu Trp Asp Leu Leu Glu Gly Lys Glu Lys Pro
                210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Ala Ala Ser Ala Pro Ala Val Glu Asp Gln Val
                260                 265                 270

Pro Glu Ala Glu Pro Glu Pro Ala Glu Glu Tyr Thr Glu Gln Ser Glu
            275                 280                 285

Val Glu Ser Thr Glu Tyr Val Asn Arg Gln Phe Met Ala Glu Thr Gln
            290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
                340                 345                 350

Leu Val Arg Arg Gln Arg Val Gln Asp Leu Met Ala Gln Met Gln Gly
                355                 360                 365

Pro Tyr Asn Phe Ile Gln Asp Ser Met Leu Asp Phe Glu Asn Gln Thr
            370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
                420                 425                 430

Pro Leu Val Ser Ser Thr Ser Glu Gly Tyr Thr Ala Ser Gln Pro Leu
                435                 440                 445

Tyr Gln Pro Ser His Ala Thr Glu Gln Arg Pro Gln Lys Glu Pro Ile
            450                 455                 460

Asp Gln Ile Gln Ala Thr Ile Ser Leu Asn Thr Asp Gln Thr Thr Ala
465                 470                 475                 480
```

```
Ser Ser Ser Leu Pro Ala Ala Ser Gln Pro Gln Val Phe Gln Ala Gly
            485                 490                 495

Thr Ser Lys Pro Leu His Ser Ser Gly Ile Asn Val Asn Ala Ala Pro
        500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
        530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
        610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Arg Gly Gly Pro Pro Arg Pro Asn Arg Gly Met Pro Gln Met Asn
        690                 695                 700

Thr Gln Gln Val Asn
705

<210> SEQ ID NO 3
<211> LENGTH: 3553
<212> TYPE: DNA
<213> ORGANISM: Homo sapiens
<220> FEATURE:
<221> NAME/KEY: CDS
<222> LOCATION: (190)..(2274)
<223> OTHER INFORMATION:

<400> SEQUENCE: 3
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccacccttg cccctcagc tgcccactcg tgatttccag cggcctccgc     180 gcgcgcacg atg ccc tcg gcc acc agc cac agc ggg agc ggc agc aag tcg    231
            Met Pro Ser Ala Thr Ser His Ser Gly Ser Gly Ser Lys Ser
             1                5                  10 tcc gga ccg cca ccg ccg tcg ggt tcc tcc ggg agt gag gcg gcc gcg    279
Ser Gly Pro Pro Pro Pro Ser Gly Ser Ser Gly Ser Glu Ala Ala Ala
 15                 20                  25                  30 gga gcc ggg gcc gcc gcg ccg gct tct cag cac ccc gca acc ggc acc    327
Gly Ala Gly Ala Ala Ala Pro Ala Ser Gln His Pro Ala Thr Gly Thr
                35                  40                  45 ggc gct gtc cag acc gag gcc atg aag cag att ctc ggg gtg atc gac    375
Gly Ala Val Gln Thr Glu Ala Met Lys Gln Ile Leu Gly Val Ile Asp
         50                  55                  60 aag aaa ctt cgg aac ctg gag aag aaa aag ggt aag ctt gat gat tac    423
```

```
              Lys Lys Leu Arg Asn Leu Glu Lys Lys Gly Lys Leu Asp Asp Tyr
                      65                  70                  75 cag gaa cga atg aac aaa ggg gaa agg ctt aat caa gat cag ctg gat           471
Gln Glu Arg Met Asn Lys Gly Glu Arg Leu Asn Gln Asp Gln Leu Asp
        80                  85                  90 gcc gtt tct aag tac cag gaa gtc aca aat aat ttg gag ttt gca aaa           519
Ala Val Ser Lys Tyr Gln Glu Val Thr Asn Asn Leu Glu Phe Ala Lys
 95                 100                 105                 110 gaa tta cag agg agt ttc atg gca cta agt caa gat att cag aaa aca           567
Glu Leu Gln Arg Ser Phe Met Ala Leu Ser Gln Asp Ile Gln Lys Thr
                115                 120                 125 ata aag aag aca gca cgt cgg gag cag ctt atg aga gaa gaa gct gaa           615
Ile Lys Lys Thr Ala Arg Arg Glu Gln Leu Met Arg Glu Glu Ala Glu
            130                 135                 140 cag aaa cgt tta aaa act gta ctt gag cta cag tat gtt ttg gac aaa           663
Gln Lys Arg Leu Lys Thr Val Leu Glu Leu Gln Tyr Val Leu Asp Lys
        145                 150                 155 ttg gga gat gat gaa gtg cgg act gac ctg aaa caa ggt ttg aat gga           711
Leu Gly Asp Asp Glu Val Arg Thr Asp Leu Lys Gln Gly Leu Asn Gly
    160                 165                 170 gtg cca ata ttg tcc gaa gag gag ttg tca ttg ttg gat gaa ttc tat           759
Val Pro Ile Leu Ser Glu Glu Glu Leu Ser Leu Leu Asp Glu Phe Tyr
175                 180                 185                 190 aag cta gta gac cct gaa cgg gac atg agc ttg agg ttg aat gaa cag           807
Lys Leu Val Asp Pro Glu Arg Asp Met Ser Leu Arg Leu Asn Glu Gln
                195                 200                 205 tat gaa cat gcc tcc att cac ctg tgg gac ctg ctg gaa ggg aag gaa           855
Tyr Glu His Ala Ser Ile His Leu Trp Asp Leu Leu Glu Gly Lys Glu
            210                 215                 220 aaa cct gta tgt gga acc acc tat aaa gtt cta aag gaa att gtt gag           903
Lys Pro Val Cys Gly Thr Thr Tyr Lys Val Leu Lys Glu Ile Val Glu
        225                 230                 235 cgt gtt ttt cag tca aac tac ttt gac agc acc cac aac cac cag aat           951
Arg Val Phe Gln Ser Asn Tyr Phe Asp Ser Thr His Asn His Gln Asn
    240                 245                 250 ggg ctg tgt gag gaa gaa gag gca gcc tca gca cct gca gtt gaa gac           999
Gly Leu Cys Glu Glu Glu Glu Ala Ala Ser Ala Pro Ala Val Glu Asp
255                 260                 265                 270 cag gta cct gaa gct gaa cct gag cca gca gaa gag tac act gag caa          1047
Gln Val Pro Glu Ala Glu Pro Glu Pro Ala Glu Glu Tyr Thr Glu Gln
                275                 280                 285 agt gaa gtt gaa tca aca gag tat gta aat aga cag ttc atg gca gaa          1095
Ser Glu Val Glu Ser Thr Glu Tyr Val Asn Arg Gln Phe Met Ala Glu
            290                 295                 300 aca cag ttc acc agt ggt gaa aag gag cag gta gat gag tgg aca gtt          1143
Thr Gln Phe Thr Ser Gly Glu Lys Glu Gln Val Asp Glu Trp Thr Val
        305                 310                 315 gaa acg gtt gag gtg gta aat tca ctc cag cag caa cct cag gct gca          1191
Glu Thr Val Glu Val Val Asn Ser Leu Gln Gln Gln Pro Gln Ala Ala
    320                 325                 330 tcc cct tca gta cca gag ccc cac tct ttg act cca gtg gct cag gca          1239
Ser Pro Ser Val Pro Glu Pro His Ser Leu Thr Pro Val Ala Gln Ala
335                 340                 345                 350 gat ccc ctt gtg aga aga cag cga gta caa gac ttg atg gca caa atg          1287
Asp Pro Leu Val Arg Arg Gln Arg Val Gln Asp Leu Met Ala Gln Met
                355                 360                 365 cag ggt ccc tat aat ttc ata cag gat tca atg ctg gat ttt gaa aat          1335
Gln Gly Pro Tyr Asn Phe Ile Gln Asp Ser Met Leu Asp Phe Glu Asn
            370                 375                 380 cag aca ctt gat cct gcc att gta tct gca cag cct atg aat cca aca          1383
```

-continued

```
          Gln Thr Leu Asp Pro Ala Ile Val Ser Ala Gln Pro Met Asn Pro Thr
                      385                 390                 395 caa aac atg gac atg ccc cag ctg gtt tgc cct cca gtt cat tct gaa       1431
Gln Asn Met Asp Met Pro Gln Leu Val Cys Pro Pro Val His Ser Glu
400                 405                 410 tct aga ctt gct cag cct aat caa gtt cct gta caa cca gaa gcg aca       1479
Ser Arg Leu Ala Gln Pro Asn Gln Val Pro Val Gln Pro Glu Ala Thr
415                 420                 425                 430 cag gtt cct ttg gta tca tcc aca agt gag ggg tac aca gca tct caa       1527
Gln Val Pro Leu Val Ser Ser Thr Ser Glu Gly Tyr Thr Ala Ser Gln
                435                 440                 445 ccc ttg tac cag cct tct cat gct aca gag caa cga cca cag aag gaa       1575
Pro Leu Tyr Gln Pro Ser His Ala Thr Glu Gln Arg Pro Gln Lys Glu
        450                 455                 460 cca att gat cag att cag gca aca atc tct tta aat aca gac cag act       1623
Pro Ile Asp Gln Ile Gln Ala Thr Ile Ser Leu Asn Thr Asp Gln Thr
        465                 470                 475 aca gca tca tca tcc ctt cct gct gcg tct cag cct caa gta ttt cag       1671
Thr Ala Ser Ser Ser Leu Pro Ala Ala Ser Gln Pro Gln Val Phe Gln
    480                 485                 490 gct ggg aca agc aaa cct tta cat agc agt gga atc aat gta aat gca       1719
Ala Gly Thr Ser Lys Pro Leu His Ser Ser Gly Ile Asn Val Asn Ala
495                 500                 505                 510 gct cca ttc caa tcc atg caa acg gtg ttc aat atg aat gcc cca gtt       1767
Ala Pro Phe Gln Ser Met Gln Thr Val Phe Asn Met Asn Ala Pro Val
                515                 520                 525 cct cct gtt aat gaa cca gaa act tta aaa cag caa aat cag tac cag       1815
Pro Pro Val Asn Glu Pro Glu Thr Leu Lys Gln Gln Asn Gln Tyr Gln
        530                 535                 540 gcc agt tat aac cag agc ttt tct agt cag cct cac caa gta gaa caa       1863
Ala Ser Tyr Asn Gln Ser Phe Ser Ser Gln Pro His Gln Val Glu Gln
    545                 550                 555 aca gag ctt cag caa gaa cag ctt caa aca gtg gtt ggc act tac cat       1911
Thr Glu Leu Gln Gln Glu Gln Leu Gln Thr Val Val Gly Thr Tyr His
560                 565                 570 ggt tcc cca gac cag tcc cat caa gtg act ggt aac cac cag cag cct       1959
Gly Ser Pro Asp Gln Ser His Gln Val Thr Gly Asn His Gln Gln Pro
575                 580                 585                 590 cct cag cag aac act gga ttt cca cgt agc aat cag ccc tat tac aat       2007
Pro Gln Gln Asn Thr Gly Phe Pro Arg Ser Asn Gln Pro Tyr Tyr Asn
                595                 600                 605 agt cgt ggt gtg tct cgt gga ggc tcc cgt ggt gct aga ggc ttg atg       2055
Ser Arg Gly Val Ser Arg Gly Gly Ser Arg Gly Ala Arg Gly Leu Met
        610                 615                 620 aat gga tac cgg ggc cct gcc aat gga ttc aga gga gga tat gat ggt       2103
Asn Gly Tyr Arg Gly Pro Ala Asn Gly Phe Arg Gly Gly Tyr Asp Gly
        625                 630                 635 tac cgc cct tca ttc tct aac act cca aac agt ggt tat aca cag tct       2151
Tyr Arg Pro Ser Phe Ser Asn Thr Pro Asn Ser Gly Tyr Thr Gln Ser
    640                 645                 650 cag ttc agt gct ccc cgg gat tac tct ggc tat caa cgg gat gga tat       2199
Gln Phe Ser Ala Pro Arg Asp Tyr Ser Gly Tyr Gln Arg Asp Gly Tyr
655                 660                 665                 670 cag cag aat ttc aag cga ggc tct ggg cag agt gga cca cgg gga gcc       2247
Gln Gln Asn Phe Lys Arg Gly Ser Gly Gln Ser Gly Pro Arg Gly Ala
                675                 680                 685 cca cga ggt aat att ttg tgg tgg tga tcctagctcc taagtggagc             2294
Pro Arg Gly Asn Ile Leu Trp Trp
                690 ttctgttctg gccttggaag agctgttaat agtctgcatg ttaggaatac atttatcctt    2354
```

```
tccagacttg ttgctaggga ttaaatgaaa tgctctgttt ctaaaactta atcttggacc   2414
caaattttaa ttttgaatg atttaatttt ccctgttact atataaactg tcttgaaaac   2474
tagaacatat tctcttctca gaaaagtgt ttttccaact gaaaattatt tttcaggtcc    2534
taaaacctgc taaatgtttt taggaagtac ttactgaaac attttgtaa gacattttg    2594 gaatgagatt gaacatttat ataaatttat tattcctctt tcatttttt gaaacatgcc    2654 tattatattt tagggccaga cacccttaa tggccggata agccatagtt aacatttaga    2714
gaaccattta gaagtgatag aactaatgga atttgcaatg cctttggac ctctattagt    2774 gatataaata tcaagttatt tctgactttt aaacaaaact cccaaattcc taacttattg   2834
agctatactt aaaaaaatt acaggtttag agagtttttt gttttctttt tactgttgga    2894
aaactacttc ccattttggc aggaagttaa cctatttaac aattagagct agcatttcat   2954
gtagtctgaa attctaaatg gttctctgat ttgagggagg ttaaacatca aacaggtttc   3014
ctctattggc cataacatgt ataaaatgtg tgttaaggag gaattacaac gtactttgat   3074
ttgaatacta gtagaaactg gccaggaaaa aggtacattt ttctaaaaat taatggatca   3134
cttgggaatt actgacttga ctagaagtat caaaggatgt ttgcatgtga atgtgggtta   3194
tgttctttcc caccttgtag catattcgat gaaagttgag ttaactgata gctaaaaatc   3254
tgttttaaca gcatgtaaaa agttatttta tctgttaaaa gtcattatac agttttgaat   3314
gttatgtagt ttcttttaa cagtttaggt aataaggtct gttttcattc tggtgctttt    3374
attaattttg atagtatgat gttacttact actgaaatgt aagctagagt gtacactaga   3434
atgtaagctc catgagagca ggtaccttgt ctgtcttctc tgctgtatct attcccaacg   3494
cttgatgatg gtgcctggca catagtaggc actcaataaa tatttgttga atgaatgaa    3553

<210> SEQ ID NO 4
<211> LENGTH: 694
<212> TYPE: PRT
<213> ORGANISM: Homo sapiens

<400> SEQUENCE: 4

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
```

-continued

```
            165                 170                 175
Ile Leu Ser Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
            195                 200                 205

His Ala Ser Ile His Leu Trp Asp Leu Leu Glu Gly Lys Glu Lys Pro
            210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                    245                 250                 255

Cys Glu Glu Glu Glu Ala Ala Ser Ala Pro Ala Val Glu Asp Gln Val
                    260                 265                 270

Pro Glu Ala Glu Pro Glu Pro Ala Glu Tyr Thr Glu Gln Ser Glu
            275                 280                 285

Val Glu Ser Thr Glu Tyr Val Asn Arg Gln Phe Met Ala Glu Thr Gln
            290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                    325                 330                 335

Ser Val Pro Glu Pro His Ser Leu Thr Pro Val Ala Gln Ala Asp Pro
                    340                 345                 350

Leu Val Arg Arg Gln Arg Val Gln Asp Leu Met Ala Gln Met Gln Gly
                    355                 360                 365

Pro Tyr Asn Phe Ile Gln Asp Ser Met Leu Asp Phe Glu Asn Gln Thr
            370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                    405                 410                 415

Leu Ala Gln Pro Asn Gln Val Pro Val Gln Pro Glu Ala Thr Gln Val
                    420                 425                 430

Pro Leu Val Ser Ser Thr Ser Glu Gly Tyr Thr Ala Ser Gln Pro Leu
            435                 440                 445

Tyr Gln Pro Ser His Ala Thr Glu Gln Arg Pro Gln Lys Glu Pro Ile
            450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                    485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
            515                 520                 525

Val Asn Glu Pro Glu Thr Leu Lys Gln Gln Asn Gln Tyr Gln Ala Ser
            530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                    565                 570                 575

Pro Asp Gln Ser His Gln Val Thr Gly Asn His Gln Gln Pro Pro Gln
            580                 585                 590
```

```
Gln Asn Thr Gly Phe Pro Arg Ser Asn Gln Pro Tyr Tyr Asn Ser Arg
            595                 600                 605

Gly Val Ser Arg Gly Ser Arg Gly Ala Arg Gly Leu Met Asn Gly
    610                 615                 620

Tyr Arg Gly Pro Ala Asn Gly Phe Arg Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
                660                 665                 670

Asn Phe Lys Arg Gly Ser Gly Gln Ser Gly Pro Arg Gly Ala Pro Arg
            675                 680                 685

Gly Asn Ile Leu Trp Trp
    690

<210> SEQ ID NO 5
<211> LENGTH: 1605
<212> TYPE: DNA
<213> ORGANISM: Canis familiaris
<220> FEATURE:
<221> NAME/KEY: CDS
<222> LOCATION: (46)..(1392)
<223> OTHER INFORMATION:

<400> SEQUENCE: 5
gtcacaaata acttggagtt tgcaaaagaa ttacagagga gtttc atg gca tta agt      57
                                                Met Ala Leu Ser
                                                  1 caa gat att cag aaa aca ata aag aag act gca cgt cgg gag cag ctt      105
Gln Asp Ile Gln Lys Thr Ile Lys Lys Thr Ala Arg Arg Glu Gln Leu
  5                  10                  15                  20 atg aga gag gaa gcg gaa caa aaa cgt tta aaa act gta ctt gag ctc      153
Met Arg Glu Glu Ala Glu Gln Lys Arg Leu Lys Thr Val Leu Glu Leu
                 25                  30                  35 cag tat gtt ttg gac aaa ttg gga gat gat gaa gtg aga act gac ctg      201
Gln Tyr Val Leu Asp Lys Leu Gly Asp Asp Glu Val Arg Thr Asp Leu
             40                  45                  50 aag caa ggt ttg aat gga gtg cca ata ttg tct gaa gaa gaa ttg tcg      249
Lys Gln Gly Leu Asn Gly Val Pro Ile Leu Ser Glu Glu Glu Leu Ser
         55                  60                  65 ttg ttg gat gaa ttc tac aaa tta gca gac cct gaa cgg gac atg agc      297
Leu Leu Asp Glu Phe Tyr Lys Leu Ala Asp Pro Glu Arg Asp Met Ser
 70                  75                  80 ttg agg ttg aat gag cag tat gaa cat gct tcc att cac ctg tgg gac      345
Leu Arg Leu Asn Glu Gln Tyr Glu His Ala Ser Ile His Leu Trp Asp
 85                  90                  95                 100 ttg ctg gaa gga aag gaa aag tct gta tgt gga aca acc tat aaa gca      393
Leu Leu Glu Gly Lys Glu Lys Ser Val Cys Gly Thr Thr Tyr Lys Ala
                105                 110                 115 cta aag gaa att gtt gag cgt gtt ttc cag tca aat tac ttt gac agc      441
Leu Lys Glu Ile Val Glu Arg Val Phe Gln Ser Asn Tyr Phe Asp Ser
            120                 125                 130 act cac aac cac cag aat ggg cta tgt gag gaa gaa gag gca gcc tca      489
Thr His Asn His Gln Asn Gly Leu Cys Glu Glu Glu Glu Ala Ala Ser
        135                 140                 145 gca cct aca gtt gaa gac cag gta gct gaa gct gag cct gag cca gca      537
Ala Pro Thr Val Glu Asp Gln Val Ala Glu Ala Glu Pro Glu Pro Ala
    150                 155                 160 gaa gaa tac act gaa caa agt gaa gtt gaa tca aca gag tat gta aat      585
Glu Glu Tyr Thr Glu Gln Ser Glu Val Glu Ser Thr Glu Tyr Val Asn
165                 170                 175                 180
```

```
aga caa ttt atg gca gaa aca cag ttc agc agt ggt gaa aag gag cag       633
Arg Gln Phe Met Ala Glu Thr Gln Phe Ser Ser Gly Glu Lys Glu Gln
            185                 190                 195 gta gat gag tgg acg gtc gaa aca gtg gag gtg gtg aat tca ctc cag       681
Val Asp Glu Trp Thr Val Glu Thr Val Glu Val Val Asn Ser Leu Gln
        200                 205                 210 cag caa cct cag gct gcg tct cct tca gta cca gag ccc cac tct ttg       729
Gln Gln Pro Gln Ala Ala Ser Pro Ser Val Pro Glu Pro His Ser Leu
    215                 220                 225 act ccg gtg gct cag gca gat ccc ctt gtg aga aga cag cga gtc cag       777
Thr Pro Val Ala Gln Ala Asp Pro Leu Val Arg Arg Gln Arg Val Gln
230                 235                 240 gac ctt atg gcg cag atg cag ggg ccc tat aat ttc ata cag gat tca       825
Asp Leu Met Ala Gln Met Gln Gly Pro Tyr Asn Phe Ile Gln Asp Ser
245                 250                 255                 260 atg ctg gat ttt gaa aac cag aca ctc gat cct gcc att gta tct gca       873
Met Leu Asp Phe Glu Asn Gln Thr Leu Asp Pro Ala Ile Val Ser Ala
                265                 270                 275 cag cct atg aat ccg aca caa aac atg gac atg ccc cag ctg gtt tgc       921
Gln Pro Met Asn Pro Thr Gln Asn Met Asp Met Pro Gln Leu Val Cys
            280                 285                 290 cct cca gtt cat tct gaa tct aga ctt gct caa cct aat caa gtt cct       969
Pro Pro Val His Ser Glu Ser Arg Leu Ala Gln Pro Asn Gln Val Pro
        295                 300                 305 gta caa cca gaa gct aca cag gtt cct ttg gtt tca tcc aca agt gag      1017
Val Gln Pro Glu Ala Thr Gln Val Pro Leu Val Ser Ser Thr Ser Glu
    310                 315                 320 ggg tat aca gca tct caa ccc ttg tac cag cct tct cat gct aca gag      1065
Gly Tyr Thr Ala Ser Gln Pro Leu Tyr Gln Pro Ser His Ala Thr Glu
325                 330                 335                 340 caa cga cca caa aag gaa cca att gac cag att cag gca aca atc tct      1113
Gln Arg Pro Gln Lys Glu Pro Ile Asp Gln Ile Gln Ala Thr Ile Ser
                345                 350                 355 tta aat aca gac cag act aca gcg tca tca tcc ctt ccg gct gct tct      1161
Leu Asn Thr Asp Gln Thr Thr Ala Ser Ser Ser Leu Pro Ala Ala Ser
            360                 365                 370 cag cct cag gta ttc cag gct ggg aca agc aaa cca tta cat agc agt      1209
Gln Pro Gln Val Phe Gln Ala Gly Thr Ser Lys Pro Leu His Ser Ser
        375                 380                 385 gga atc aat gta aat gca gct cca ttc caa tcc atg caa acg gtg ttc      1257
Gly Ile Asn Val Asn Ala Ala Pro Phe Gln Ser Met Gln Thr Val Phe
    390                 395                 400 aat atg aat gcc cca gtt cct cct gtt aat gaa cca gaa act ttg aaa      1305
Asn Met Asn Ala Pro Val Pro Pro Val Asn Glu Pro Glu Thr Leu Lys
405                 410                 415                 420 caa caa aat cag tac cag gcc agt tat aac cag agc ttt tct agt cag      1353
Gln Gln Asn Gln Tyr Gln Ala Ser Tyr Asn Gln Ser Phe Ser Ser Gln
                425                 430                 435 cct cac caa gta gaa caa aca gag gga tgc cgc aaa tga acactcagca       1402
Pro His Gln Val Glu Gln Thr Glu Gly Cys Arg Lys
            440                 445 agtgaattaa tctgattcac aggattatgt ttaaacgcca aaaacacact ggccagtgta    1462
ccataatatg ttaccagaag agttattatc tatttgttct ccctttcagg aaacttattg    1522
taaagggact gttttcatcc cataaagaca ggactacaat tgtcagcttt atattacctg    1582
gaaaaaaaaa aaaaaaaaaa aaa                                            1605

<210> SEQ ID NO 6
<211> LENGTH: 448
```

```
<212> TYPE: PRT
<213> ORGANISM: Canis familiaris

<400> SEQUENCE: 6

Met Ala Leu Ser Gln Asp Ile Gln Lys Thr Ile Lys Lys Thr Ala Arg
1               5                   10                  15

Arg Glu Gln Leu Met Arg Glu Ala Glu Gln Lys Arg Leu Lys Thr
            20                  25                  30

Val Leu Glu Leu Gln Tyr Val Leu Asp Lys Leu Gly Asp Asp Glu Val
            35                  40                  45

Arg Thr Asp Leu Lys Gln Gly Leu Asn Gly Val Pro Ile Leu Ser Glu
50                  55                  60

Glu Glu Leu Ser Leu Leu Asp Glu Phe Tyr Lys Leu Ala Asp Pro Glu
65                  70                  75                  80

Arg Asp Met Ser Leu Arg Leu Asn Glu Gln Tyr Glu His Ala Ser Ile
                85                  90                  95

His Leu Trp Asp Leu Leu Glu Gly Lys Glu Lys Ser Val Cys Gly Thr
            100                 105                 110

Thr Tyr Lys Ala Leu Lys Glu Ile Val Glu Arg Val Phe Gln Ser Asn
            115                 120                 125

Tyr Phe Asp Ser Thr His Asn His Gln Asn Gly Leu Cys Glu Glu Glu
130                 135                 140

Glu Ala Ala Ser Ala Pro Thr Val Glu Asp Gln Val Ala Glu Ala Glu
145                 150                 155                 160

Pro Glu Pro Ala Glu Glu Tyr Thr Glu Gln Ser Glu Val Glu Ser Thr
                165                 170                 175

Glu Tyr Val Asn Arg Gln Phe Met Ala Glu Thr Gln Phe Ser Ser Gly
            180                 185                 190

Glu Lys Glu Gln Val Asp Glu Trp Thr Val Glu Thr Val Glu Val Val
            195                 200                 205

Asn Ser Leu Gln Gln Pro Gln Ala Ala Ser Pro Ser Val Pro Glu
210                 215                 220

Pro His Ser Leu Thr Pro Val Ala Gln Ala Asp Pro Leu Val Arg Arg
225                 230                 235                 240

Gln Arg Val Gln Asp Leu Met Ala Gln Met Gln Gly Pro Tyr Asn Phe
                245                 250                 255

Ile Gln Asp Ser Met Leu Asp Phe Glu Asn Gln Thr Leu Asp Pro Ala
            260                 265                 270

Ile Val Ser Ala Gln Pro Met Asn Pro Thr Gln Asn Met Asp Met Pro
            275                 280                 285

Gln Leu Val Cys Pro Pro Val His Ser Glu Ser Arg Leu Ala Gln Pro
290                 295                 300

Asn Gln Val Pro Val Gln Pro Glu Ala Thr Gln Val Pro Leu Val Ser
305                 310                 315                 320

Ser Thr Ser Glu Gly Tyr Thr Ala Ser Gln Pro Leu Tyr Gln Pro Ser
                325                 330                 335

His Ala Thr Glu Gln Arg Pro Gln Lys Glu Pro Ile Asp Gln Ile Gln
            340                 345                 350

Ala Thr Ile Ser Leu Asn Thr Asp Gln Thr Thr Ala Ser Ser Ser Leu
            355                 360                 365

Pro Ala Ala Ser Gln Pro Gln Val Phe Gln Ala Gly Thr Ser Lys Pro
370                 375                 380

Leu His Ser Ser Gly Ile Asn Val Asn Ala Ala Pro Phe Gln Ser Met
385                 390                 395                 400
```

```
Gln Thr Val Phe Asn Met Asn Ala Pro Val Pro Val Asn Glu Pro
            405                 410                 415

Glu Thr Leu Lys Gln Gln Asn Gln Tyr Gln Ala Ser Tyr Asn Gln Ser
        420                 425                 430

Phe Ser Ser Gln Pro His Gln Val Glu Gln Thr Glu Gly Cys Arg Lys
        435                 440                 445

<210> SEQ ID NO 7
<211> LENGTH: 4154
<212> TYPE: DNA
<213> ORGANISM: Canis familiaris
<220> FEATURE:
<221> NAME/KEY: CDS
<222> LOCATION: (1)..(2154)
<223> OTHER INFORMATION:

<400> SEQUENCE: 7 atg ccg tcg gcc acc agc ctc agc gga agc ggc agc aag tcg tcg ggc      48
Met Pro Ser Ala Thr Ser Leu Ser Gly Ser Gly Ser Lys Ser Ser Gly
1               5                  10                  15 ccg ccg ccc ccg tcg ggt tcc tcc ggg agc gag gcg gcg gcg gcg gcg      96
Pro Pro Pro Pro Ser Gly Ser Ser Gly Ser Glu Ala Ala Ala Ala Ala
            20                  25                  30 ggg gcg gcg ggg gcg gcg ggg gcc ggg gcg gct gcg ccc gcc tcc cag     144
Gly Ala Ala Gly Ala Ala Gly Ala Gly Ala Ala Ala Pro Ala Ser Gln
        35                  40                  45 cac ccc gcg acc ggc acc ggc gct gtc cag acc gag gcc atg aag cag     192
His Pro Ala Thr Gly Thr Gly Ala Val Gln Thr Glu Ala Met Lys Gln
    50                  55                  60 atc ctc ggg gtg atc gac aag aaa ctc cgg aac ctg gag aag aaa aag     240
Ile Leu Gly Val Ile Asp Lys Lys Leu Arg Asn Leu Glu Lys Lys Lys
65                  70                  75                  80 ggc aag ctt gat gat tac cag gaa cga atg aac aaa ggg gaa agg ctt     288
Gly Lys Leu Asp Asp Tyr Gln Glu Arg Met Asn Lys Gly Glu Arg Leu
                85                  90                  95 aat caa gat cag ctg gat gcc gta tct aag tac cag gaa gtc aca aat     336
Asn Gln Asp Gln Leu Asp Ala Val Ser Lys Tyr Gln Glu Val Thr Asn
            100                 105                 110 aac ttg gag ttt gca aaa gaa tta cag agg agt ttc atg gca tta agt     384
Asn Leu Glu Phe Ala Lys Glu Leu Gln Arg Ser Phe Met Ala Leu Ser
        115                 120                 125 caa gat att cag aaa aca ata aag aag act gca cgt cgg gag cag ctt     432
Gln Asp Ile Gln Lys Thr Ile Lys Lys Thr Ala Arg Arg Glu Gln Leu
    130                 135                 140 atg aga gag gaa gcg gaa caa aaa cgt tta aaa act gta ctt gag ctc     480
Met Arg Glu Glu Ala Glu Gln Lys Arg Leu Lys Thr Val Leu Glu Leu
145                 150                 155                 160 cag tat gtt ttg gac aaa ttg gga gat gat gaa gtg aga act gac ctg     528
Gln Tyr Val Leu Asp Lys Leu Gly Asp Asp Glu Val Arg Thr Asp Leu
                165                 170                 175 aag caa ggt ttg aat gga gtg cca ata ttg tct gaa gaa gaa ttg tcg     576
Lys Gln Gly Leu Asn Gly Val Pro Ile Leu Ser Glu Glu Glu Leu Ser
            180                 185                 190 ttg ttg gat gaa ttc tac aaa tta gca gac cct gaa cgg gac atg agc     624
Leu Leu Asp Glu Phe Tyr Lys Leu Ala Asp Pro Glu Arg Asp Met Ser
        195                 200                 205 ttg agg ttg aat gag cag tat gaa cat gct tcc att cac ctg tgg gac     672
Leu Arg Leu Asn Glu Gln Tyr Glu His Ala Ser Ile His Leu Trp Asp
    210                 215                 220 ttg ctg gaa gga aag gaa aag tct gta tgt gga aca acc tat aaa gca     720
Leu Leu Glu Gly Lys Glu Lys Ser Val Cys Gly Thr Thr Tyr Lys Ala
225                 230                 235                 240
```

| | | |
|---|---|---|
| cta aag gaa att gtt gag cgt gtt ttc cag tca aat tac ttt gac agc<br>Leu Lys Glu Ile Val Glu Arg Val Phe Gln Ser Asn Tyr Phe Asp Ser<br>                245                    250                    255 | | 768 |
| act cac aac cac cag aat ggg cta tgt gag gaa gaa gag gca gcc tca<br>Thr His Asn His Gln Asn Gly Leu Cys Glu Glu Glu Glu Ala Ala Ser<br>260                    265                    270 | | 816 |
| gca cct aca gtt gaa gac cag gta gct gaa gct gag cct gag cca gca<br>Ala Pro Thr Val Glu Asp Gln Val Ala Glu Ala Glu Pro Glu Pro Ala<br>        275                    280                    285 | | 864 |
| gaa gaa tac act gaa caa agt gaa gtt gaa tca aca gag tat gta aat<br>Glu Glu Tyr Thr Glu Gln Ser Glu Val Glu Ser Thr Glu Tyr Val Asn<br>290                    295                    300 | | 912 |
| aga caa ttt atg gca gaa aca cag ttc agc agt ggt gaa aag gag cag<br>Arg Gln Phe Met Ala Glu Thr Gln Phe Ser Ser Gly Glu Lys Glu Gln<br>305                    310                    315                    320 | | 960 |
| gta gat gag tgg acg gtc gaa aca gtg gag gtg gtg aat tca ctc cag<br>Val Asp Glu Trp Thr Val Glu Thr Val Glu Val Val Asn Ser Leu Gln<br>                        325                    330                    335 | | 1008 |
| cag caa cct cag gct gcg tct cct tca gta cca gag ccc cac tct ttg<br>Gln Gln Pro Gln Ala Ala Ser Pro Ser Val Pro Glu Pro His Ser Leu<br>        340                    345                    350 | | 1056 |
| act ccg gtg gct cag gca gat ccc ctt gtg aga aga cag cga gtc cag<br>Thr Pro Val Ala Gln Ala Asp Pro Leu Val Arg Arg Gln Arg Val Gln<br>                355                    360                    365 | | 1104 |
| gac ctt atg gcg cag atg cag ggg ccc tat aat ttc ata cag gat tca<br>Asp Leu Met Ala Gln Met Gln Gly Pro Tyr Asn Phe Ile Gln Asp Ser<br>370                    375                    380 | | 1152 |
| atg ctg gat ttt gaa aac cag aca ctc gat cct gcc att gta tct gca<br>Met Leu Asp Phe Glu Asn Gln Thr Leu Asp Pro Ala Ile Val Ser Ala<br>385                    390                    395                    400 | | 1200 |
| cag cct atg aat ccg aca caa aac atg gac atg ccc cag ctg gtt tgc<br>Gln Pro Met Asn Pro Thr Gln Asn Met Asp Met Pro Gln Leu Val Cys<br>                        405                    410                    415 | | 1248 |
| cct cca gtt cat tct gaa tct aga ctt gct caa cct aat caa gtt cct<br>Pro Pro Val His Ser Glu Ser Arg Leu Ala Gln Pro Asn Gln Val Pro<br>        420                    425                    430 | | 1296 |
| gta caa cca gaa gct aca cag gtt cct ttg gtt tca tcc aca agt gag<br>Val Gln Pro Glu Ala Thr Gln Val Pro Leu Val Ser Ser Thr Ser Glu<br>                435                    440                    445 | | 1344 |
| ggg tat aca gca tct caa ccc ttg tac cag cct tct cat gct aca gag<br>Gly Tyr Thr Ala Ser Gln Pro Leu Tyr Gln Pro Ser His Ala Thr Glu<br>450                    455                    460 | | 1392 |
| caa cga cca caa aag gaa cca att gac cag att cag gca aca atc tct<br>Gln Arg Pro Gln Lys Glu Pro Ile Asp Gln Ile Gln Ala Thr Ile Ser<br>465                    470                    475                    480 | | 1440 |
| tta aat aca gac cag act aca gcg tca tca tcc ctt ccg gct gct tct<br>Leu Asn Thr Asp Gln Thr Thr Ala Ser Ser Ser Leu Pro Ala Ala Ser<br>                        485                    490                    495 | | 1488 |
| cag cct cag gta ttc cag gct ggg aca agc aaa cca tta cat agc agt<br>Gln Pro Gln Val Phe Gln Ala Gly Thr Ser Lys Pro Leu His Ser Ser<br>        500                    505                    510 | | 1536 |
| gga atc aat gta aat gca gct cca ttc caa tcc atg caa acg gtg ttc<br>Gly Ile Asn Val Asn Ala Ala Pro Phe Gln Ser Met Gln Thr Val Phe<br>                515                    520                    525 | | 1584 |
| aat atg aat gcc cca gtt cct cct gtt aat gaa cca gaa act ttg aaa<br>Asn Met Asn Ala Pro Val Pro Pro Val Asn Glu Pro Glu Thr Leu Lys<br>530                    535                    540 | | 1632 |
| caa caa aat cag tac cag gcc agt tat aac cag agc ttt tct agt cag<br>Gln Gln Asn Gln Tyr Gln Ala Ser Tyr Asn Gln Ser Phe Ser Ser Gln<br>545                    550                    555                    560 | | 1680 |

```
cct cac caa gta gaa caa aca gac ctt cag caa gaa cag ctt caa aca    1728
Pro His Gln Val Glu Gln Thr Asp Leu Gln Gln Glu Gln Leu Gln Thr
            565                 570                 575 gtg gtt ggc act tac cat ggt tcc cag gac cag ccc cac caa gtg act    1776
Val Val Gly Thr Tyr His Gly Ser Gln Asp Gln Pro His Gln Val Thr
        580                 585                 590 ggt aac cat cag cag cct ccc cag cag aac act gga ttt cca cgt agc    1824
Gly Asn His Gln Gln Pro Pro Gln Gln Asn Thr Gly Phe Pro Arg Ser
    595                 600                 605 agt cag ccc tat tac aat agt cgt ggt gtg tct cgt ggt ggt tcc cgt    1872
Ser Gln Pro Tyr Tyr Asn Ser Arg Gly Val Ser Arg Gly Gly Ser Arg
610                 615                 620 ggt gct aga ggc tta atg aat gga tac agg ggc cct gcc aat gga ttc    1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac    1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc    2016
Ser Gly Tyr Thr Gln Ser Gln Phe Ser Ala Pro Arg Asp Tyr Ser Gly
            660                 665                 670 tat cag cgg gat gga tat cag cag aat ttc aag cga ggc tct ggg cag    2064
Tyr Gln Arg Asp Gly Tyr Gln Gln Asn Phe Lys Arg Gly Ser Gly Gln
        675                 680                 685 agt gga cca cgg gga gcc cca cga ggt cgt gga ggg ccc cca aga ccc    2112
Ser Gly Pro Arg Gly Ala Pro Arg Gly Arg Gly Gly Pro Pro Arg Pro
    690                 695                 700 aac aga ggg atg ccg caa atg aac act cag caa gtg aat taa            2154
Asn Arg Gly Met Pro Gln Met Asn Thr Gln Gln Val Asn
705                 710                 715 tctgattcac aggattatgt ttaaacgcca aaaacacact ggccagtgta ccataatatg   2214
ttaccgaaag agttattatc tatttgttct ccctttcagg aaacttattg taaagggact   2274
gttttcatcc cataaagaca ggactacaat tgtcagcttt atattacctg gatatggaag   2334
gaaactattt ttattctgca tgttcttcct aagcgtcatc ttgagccttg cacatgatac   2394
tcagattcct caccottgct taggagtaaa acataataca ctttacaggg tgatatctcc   2454
atagttattt gaagtggctt ggaaaaagca agattaactt ctgacattgg ataaaaatca   2514
acaaatcagc cctagagtta ttcaaatggt aattgacaaa aactaaaata tttcccttcg   2574
agaaggagtg aatgtggtt tggcagaaca actgcatttc acagcttttc cggttaaatt    2634
ggagcactaa acgtttagat gcataccaaa ttatgcatgg gcccttaata taaaaggctg   2694
gctaccagct ttgacacagc actattcatc ctctggccaa acaactgtgg ttaaacaaca   2754
catgtaaatt gcttttttaac agctgatact ataataagac aaagccaaaa tgcaaaaatt  2814
gggctttgat tggcactttt tgaaaaatat gcaacaaata tgggatgtaa tctggatggc   2874
cgcttctgta cttaatgtga agtatttaga taccttttg aacacttaac agtttcttct    2934
gacaatgact tttgtaagga ttggtactat ctatcattcc ttataatgta cattgtctgt   2994
cactaatcct cagatcttgc tgtattgtca cctaaattgg tacaggtact gatgaaaata   3054
tctaatggat aatcataaca ctcttggtca catgttttc ctgcagcctg aaggttttta    3114
aaagaaaaag atatcaaatg cctgctgcta ccacccttt aaattgctat cttttgaaaa    3174
gcaccagtat gtgttttaga ttgatttccc tattttaggg aaatgacaga cagtagtttc   3234
agttctgatg gtataagcaa aacaaataaa acatgtttat aaaagttgta tcttgaaaca   3294
ctggtgttca acagctagca gcttatgtgg ttcaccccat gcattgttag tgtttcagat   3354
```

```
tttatggtta tctccagcag ctgtttctgt agtacttgca tttatctttt gtctaaccct   3414
aatattctca cggaggcatt tatattcaaa gtggtgatcc cttcacttag acgcataggg   3474
agagtcacaa gtttgatgaa gaggacagtg tagtaattta tatgctgttg gaatttgtgc   3534
tagcagtttg agcactagtt ctgtgtgcct atgaacttaa tgctgcttgt catattccac   3594
tttgacttca tggagaatta atcccatcta ctcagcaaag gctatactaa tactaagtta   3654
atggtatttt ctgtgcagaa attgaatttt gtttttattag catttagcta aggaattttt   3714
ccagtaggtg ctcagctact aaagaaaaac aaaaacaaga cacaaaacta ttctcaaaca   3774
ttcattgtta gacaactgga gttttgctg gttttgtaac ctactaaaat ggataggctg    3834
ttgaacattc cacattcaaa gttttttgt agggtggtgg ggaagggggg gtgtcttcaa    3894
tgtttatttt aaaataaaat aagttcttga cttttctcat gtgtggttgt ggtacatcat   3954
attggaaggg ttatctgttt acttttgcaa atgagtattt ctcttgctag cacctcccgt   4014
tgtgcgcttt aaatgacatc tgcctgggat gtaccacaac catatgttag ctgtatttta   4074
tggggaatag ataaaatatt cgtggtttat tgggtaatcc ctagatgtgt atgcttacaa   4134
tcctatatat aaaactaaat                                                4154

<210> SEQ ID NO 8
<211> LENGTH: 717
<212> TYPE: PRT
<213> ORGANISM: Canis familiaris

<400> SEQUENCE: 8

Met Pro Ser Ala Thr Ser Leu Ser Gly Ser Gly Ser Lys Ser Gly
1               5                   10                  15

Pro Pro Pro Ser Gly Ser Ser Gly Ser Glu Ala Ala Ala Ala
            20                  25                  30

Gly Ala Ala Gly Ala Ala Gly Ala Gly Ala Ala Pro Ala Ser Gln
                35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
```

-continued

```
              225                 230                 235                 240
Leu Lys Glu Ile Val Glu Arg Val Phe Gln Ser Asn Tyr Phe Asp Ser
                245                 250                 255
Thr His Asn His Gln Asn Gly Leu Cys Glu Glu Glu Ala Ala Ser
            260                 265                 270
Ala Pro Thr Val Glu Asp Gln Val Ala Glu Ala Glu Pro Glu Pro Ala
                275                 280                 285
Glu Glu Tyr Thr Glu Gln Ser Glu Val Glu Ser Thr Glu Tyr Val Asn
            290                 295                 300
Arg Gln Phe Met Ala Glu Thr Gln Phe Ser Ser Gly Glu Lys Glu Gln
305                 310                 315                 320
Val Asp Glu Trp Thr Val Glu Thr Val Glu Val Asn Ser Leu Gln
                325                 330                 335
Gln Gln Pro Gln Ala Ala Ser Pro Ser Val Pro Glu Pro His Ser Leu
            340                 345                 350
Thr Pro Val Ala Gln Ala Asp Pro Leu Val Arg Arg Gln Arg Val Gln
                355                 360                 365
Asp Leu Met Ala Gln Met Gln Gly Pro Tyr Asn Phe Ile Gln Asp Ser
        370                 375                 380
Met Leu Asp Phe Glu Asn Gln Thr Leu Asp Pro Ala Ile Val Ser Ala
385                 390                 395                 400
Gln Pro Met Asn Pro Thr Gln Asn Met Asp Met Pro Gln Leu Val Cys
                405                 410                 415
Pro Pro Val His Ser Glu Ser Arg Leu Ala Gln Pro Asn Gln Val Pro
            420                 425                 430
Val Gln Pro Glu Ala Thr Gln Val Pro Leu Val Ser Ser Thr Ser Glu
            435                 440                 445
Gly Tyr Thr Ala Ser Gln Pro Leu Tyr Gln Pro Ser His Ala Thr Glu
        450                 455                 460
Gln Arg Pro Gln Lys Glu Pro Ile Asp Gln Ile Gln Ala Thr Ile Ser
465                 470                 475                 480
Leu Asn Thr Asp Gln Thr Thr Ala Ser Ser Leu Pro Ala Ala Ser
                485                 490                 495
Gln Pro Gln Val Phe Gln Ala Gly Thr Ser Lys Pro Leu His Ser Ser
            500                 505                 510
Gly Ile Asn Val Asn Ala Ala Pro Phe Gln Ser Met Gln Thr Val Phe
        515                 520                 525
Asn Met Asn Ala Pro Val Pro Pro Val Asn Glu Pro Glu Thr Leu Lys
        530                 535                 540
Gln Gln Asn Gln Tyr Gln Ala Ser Tyr Asn Gln Ser Phe Ser Ser Gln
545                 550                 555                 560
Pro His Gln Val Glu Gln Thr Asp Leu Gln Gln Glu Gln Leu Gln Thr
                565                 570                 575
Val Val Gly Thr Tyr His Gly Ser Gln Asp Gln Pro His Gln Val Thr
            580                 585                 590
Gly Asn His Gln Gln Pro Pro Gln Gln Asn Thr Gly Phe Pro Arg Ser
        595                 600                 605
Ser Gln Pro Tyr Tyr Asn Ser Arg Gly Val Ser Arg Gly Gly Ser Arg
        610                 615                 620
Gly Ala Arg Gly Leu Met Asn Gly Tyr Arg Gly Pro Ala Asn Gly Phe
625                 630                 635                 640
Arg Gly Gly Tyr Asp Gly Tyr Arg Pro Ser Phe Ser Asn Thr Pro Asn
                645                 650                 655
```

```
                Ser Gly Tyr Thr Gln Ser Gln Phe Ser Ala Pro Arg Asp Tyr Ser Gly
                                660                 665                 670

Tyr Gln Arg Asp Gly Tyr Gln Asn Phe Lys Arg Gly Ser Gly Gln
                        675                 680                 685

Ser Gly Pro Arg Gly Ala Pro Arg Gly Arg Gly Pro Pro Arg Pro
                        690                 695                 700

Asn Arg Gly Met Pro Gln Met Asn Thr Gln Gln Val Asn
                705                 710                 715

<210> SEQ ID NO 9
<211> LENGTH: 4939
<212> TYPE: DNA
<213> ORGANISM: Canis familiaris
<220> FEATURE:
<221> NAME/KEY: CDS
<222> LOCATION: (1)..(2109)
<223> OTHER INFORMATION:

<400> SEQUENCE: 9
```

| | | |
|---|---|---|
| atg ccg tcg gcc acc agc ctc agc gga agc ggc agc aag tcg tcg ggc | | 48 |
| Met Pro Ser Ala Thr Ser Leu Ser Gly Ser Gly Ser Lys Ser Ser Gly | | |
| 1               5                   10                  15 | | |
| | | |
| ccg ccg ccc ccg tcg ggt tcc tcc ggg agc gag gcg gcg gcg gcg gcg | | 96 |
| Pro Pro Pro Pro Ser Gly Ser Ser Gly Ser Glu Ala Ala Ala Ala Ala | | |
|             20                  25                  30 | | |
| | | |
| ggg gcg gcg ggg gcg gcg ggg gcc ggg gcg gct gcg ccc gcc tcc cag | | 144 |
| Gly Ala Ala Gly Ala Ala Gly Ala Gly Ala Ala Ala Pro Ala Ser Gln | | |
|         35                  40                  45 | | |
| | | |
| cac ccc gcg acc ggc acc ggc gct gtc cag acc gag gcc atg aag cag | | 192 |
| His Pro Ala Thr Gly Thr Gly Ala Val Gln Thr Glu Ala Met Lys Gln | | |
| 50                  55                  60 | | |
| | | |
| atc ctc ggg gtg atc gac aag aaa ctc cgg aac ctg gag aag aaa aag | | 240 |
| Ile Leu Gly Val Ile Asp Lys Lys Leu Arg Asn Leu Glu Lys Lys Lys | | |
| 65                  70                  75                  80 | | |
| | | |
| ggc aag ctt gat gat tac cag gaa cga atg aac aaa ggg gaa agg ctt | | 288 |
| Gly Lys Leu Asp Asp Tyr Gln Glu Arg Met Asn Lys Gly Glu Arg Leu | | |
|                 85                  90                  95 | | |
| | | |
| aat caa gat cag ctg gat gcc gta tct aag tac cag gaa gtc aca aat | | 336 |
| Asn Gln Asp Gln Leu Asp Ala Val Ser Lys Tyr Gln Glu Val Thr Asn | | |
|             100                 105                 110 | | |
| | | |
| aac ttg gag ttt gca aaa gaa tta cag agg agt ttc atg gca tta agt | | 384 |
| Asn Leu Glu Phe Ala Lys Glu Leu Gln Arg Ser Phe Met Ala Leu Ser | | |
|         115                 120                 125 | | |
| | | |
| caa gat att cag aaa aca ata aag aag act gca cgt cgg gag cag ctt | | 432 |
| Gln Asp Ile Gln Lys Thr Ile Lys Lys Thr Ala Arg Arg Glu Gln Leu | | |
|     130                 135                 140 | | |
| | | |
| atg aga gag gaa gcg gaa caa aaa cgt tta aaa act gta ctt gag ctc | | 480 |
| Met Arg Glu Glu Ala Glu Gln Lys Arg Leu Lys Thr Val Leu Glu Leu | | |
| 145                 150                 155                 160 | | |
| | | |
| cag tat gtt ttg gac aaa ttg gga gat gat gaa gtg aga act gac ctg | | 528 |
| Gln Tyr Val Leu Asp Lys Leu Gly Asp Asp Glu Val Arg Thr Asp Leu | | |
|                 165                 170                 175 | | |
| | | |
| aag caa ggt ttg aat gga gtg cca ata ttg tct gaa gaa gaa ttg tcg | | 576 |
| Lys Gln Gly Leu Asn Gly Val Pro Ile Leu Ser Glu Glu Glu Leu Ser | | |
|             180                 185                 190 | | |
| | | |
| ttg ttg gat gaa ttc tac aaa tta gca gac cct gaa cgg gac atg agc | | 624 |
| Leu Leu Asp Glu Phe Tyr Lys Leu Ala Asp Pro Glu Arg Asp Met Ser | | |
|         195                 200                 205 | | |
| | | |
| ttg agg ttg aat gag cag tat gaa cat gct tcc att cac ctg tgg gac | | 672 |
| Leu Arg Leu Asn Glu Gln Tyr Glu His Ala Ser Ile His Leu Trp Asp | | |
|     210                 215                 220 | | |

```
ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240 cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255 act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270 gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285 gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300 aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320 gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335 cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350 act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365 gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380 atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400 cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415 cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430 gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445 ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460 caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480 tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495 cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510 gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525 aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540
```

```
caa caa aat cag tac cag gcc agt tat aac cag agc ttt tct agt cag      1680
Gln Gln Asn Gln Tyr Gln Ala Ser Tyr Asn Gln Ser Phe Ser Ser Gln
545                 550                 555                 560 cct cac caa gta gaa caa aca gac ctt cag caa gaa cag ctt caa aca      1728
Pro His Gln Val Glu Gln Thr Asp Leu Gln Gln Glu Gln Leu Gln Thr
                565                 570                 575 gtg gtt ggc act tac cat ggt tcc cag gac cag ccc cac caa gtg act      1776
Val Val Gly Thr Tyr His Gly Ser Gln Asp Gln Pro His Gln Val Thr
            580                 585                 590 ggt aac cat cag cag cct ccc cag cag aac act gga ttt cca cgt agc      1824
Gly Asn His Gln Gln Pro Pro Gln Gln Asn Thr Gly Phe Pro Arg Ser
        595                 600                 605 agt cag ccc tat tac aat agt cgt ggt gtg tct cgt ggt ggt tcc cgt      1872
Ser Gln Pro Tyr Tyr Asn Ser Arg Gly Val Ser Arg Gly Gly Ser Arg
    610                 615                 620 ggt gct aga ggc tta atg aat gga tac agg ggc cct gcc aat gga ttc      1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac      1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc      2016
Ser Gly Tyr Thr Gln Ser Gln Phe Ser Ala Pro Arg Asp Tyr Ser Gly
            660                 665                 670 tat cag cgg gat gga tat cag cag aat ttc aag cga ggc tct ggg cag      2064
Tyr Gln Arg Asp Gly Tyr Gln Gln Asn Phe Lys Arg Gly Ser Gly Gln
        675                 680                 685 agt gga cca cgg gga gcc cca cga ggt aat att ttg tgg tgg tga          2109
Ser Gly Pro Arg Gly Ala Pro Arg Gly Asn Ile Leu Trp Trp
    690                 695                 700 tcctagctcc taagtggagc ttctgttctg gccttggaag agctgttcca tagtctgcat    2169
gtaggttaca tgttaggaat acatttatca ttaccagact tgttgctagg gattaaatga    2229
aatgctctgt ttctaaaact tctcttgaac ccaaatttaa ttttttgaat gacttttccct   2289 gttactatat aaattgtctt gaaaactaga acatttctcc tcctcagaaa aagtgttttt    2349
ccaactgcaa attattttc aggtcctaaa acctgctaaa tgttttagg aagtacttac     2409 tgaaacattt ttgtaagaca ttttttggaat gagattgaac atttatataa atttattatt   2469
attcctcttt cattttgaa catgcatatt atatttagg gtcagaaatc ctttaatggc     2529
caaataagcc atagttacat ttagagaacc atttagaagt gatagaacta actgaaattt    2589
caatgccttt ggatcattaa tagcgatata aatttcaaat tgtttctgac ttttaaataa    2649
aacatccaaa atcctaacta acttcctgaa ctatatttaa aaattacagg tttaaggagt    2709
ttctggtttt ttttctctta ccataggaaa actgttcct gtttggccag gaagtcaacc    2769
tgtgtaataa ttagaagtag catttcatat gatctgaagt tctaaatggt tctctgattt    2829
aagggaagtt aaattgaata ggtttcctct agttattggc cataacatgt ataaaatgta    2889
tattaaggag gaatacaaag tactttgatt tcaatgctag tagaaactgg ccagcaaaaa    2949
ggtgcatttt atttttaaat taatggatca cttgggaatt actgacttga agtatcaaag    3009
gatatttgca tgtgaatgtg ggttatgttc tttctcacct tgtagcatat tctatgaaag    3069
ttgagttgac tggtagctaa aaatctgttt taacagcatg taaaaagtta ttttatctgt    3129
tacaagtcat tatacaattt tgaatgttat gtagtttctt tttaacagtt taggtaacaa    3189
ggtctgtttt tcattctggt gcttttatta attttgatag tatgatgtta cttactactg    3249
aaatgtaagc tagagtgtac actagaatgt aagctccatg agagcaggta ccttgtctgt    3309
```

```
cttcactgct gtatctattt ccaacgcctg atgacagtgc ctgacacata gtaggcactc    3369
aataaatact tgttgaatga atgaatgaat gagtactggt ggaatactcc attagctcta    3429
ctcttctttt agctagagaa catgagcaaa tttgcgcatg acaacttcca ggacaggtga    3489
acactgaaga attgacctct taaacctaat aatgtggtga caagctgccc acatgcttct    3549
tgacttcaga tgaaaatctg cttgaaggca aagcaaataa tatttgaaag aaaaaccaaa    3609
tgccattttt gtcttctagg tcgtggaggg cccccaagac ccaacagagg gatgccgcaa    3669
atgaacactc agcaagtgaa ttaatctgat tcacaggatt atgtttaaac gccaaaaaca    3729
cactggccag tgtaccataa tatgttacca gaagagttat tatctatttg ttctcccttt    3789
caggaaactt attgtaaagg gactgttttc atcccataaa gacaggacta caattgtcag    3849
ctttatatta cctggatatg gaaggaaact attttttattc tgcatgttct tcctaagcgt    3909
catcttgagc cttgcacatg atactcagat tcctcacccct tgcttaggag taaaacataa    3969
tacactttac agggtgatat ctccatagtt atttgaagtg gcttggaaaa agcaagatta    4029
acttctgaca ttggataaaa atcaacaaat cagccctaga gttattcaaa tggtaattga    4089
caaaaactaa atatttccc ttcgagaagg agtggaatgt ggtttggcag aacaactgca    4149
tttcacagct tttccggtta aattggagca ctaaacgttt agatgcatac caaattatgc    4209
atgggccctt aatataaaag gctggctacc agctttgaca cagcactatt catcctctgg    4269
ccaaacaact gtggttaaac aacacatgta aattgctttt taacagctga tactataata    4329
agacaaagcc aaaatgcaaa aattgggctt tgattggcac tttttgaaaa atatgcaaca    4389
aatatgggat gtaatctgga tggccgcttc tgtacttaat gtgaagtatt tagataccct    4449
tttgaacact taacagtttc ttctgacaat gactttttgta aggattggta ctatctatca    4509
ttccttataa tgtacattgt ctgtcactaa tcctcagatc ttgctgtatt gtcacctaaa    4569
ttggtacagg tactgatgaa aatatctaat ggataatcat aacactcttg gtcacatgtt    4629
tttcctgcag cctgaaggtt tttaaaagaa aaagatatca aatgcctgct gctaccaccc    4689
ttttaaattg ctatcttttg aaaagcacca gtatgtgttt tagattgatt tccctatttt    4749
agggaaatga cagacagtag tttcagttct gatggtataa gcaaaacaaa taaaacatgt    4809
ttataaaagt tgtatcttga aacactggtg ttcaacagct agcagcttat gtggttcacc    4869
ccatgcattg ttagtgtttc agattttatg gttatctcca gcagctgttt ctgtagtact    4929
tgcatttatc                                                          4939
```

<210> SEQ ID NO 10
<211> LENGTH: 702
<212> TYPE: PRT
<213> ORGANISM: Canis familiaris

<400> SEQUENCE: 10

```
Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys
65                  70                  75                  80

Gly Lys Leu Asp Asp Tyr Gln Glu Arg Met Asn Lys Gly Glu Arg Leu
```

```
            85                  90                  95
Asn Gln Asp Gln Leu Asp Ala Val Ser Lys Tyr Gln Glu Val Thr Asn
            100                 105                 110
Asn Leu Glu Phe Ala Lys Glu Leu Gln Arg Ser Phe Met Ala Leu Ser
            115                 120                 125
Gln Asp Ile Gln Lys Thr Ile Lys Lys Thr Ala Arg Arg Glu Gln Leu
            130                 135                 140
Met Arg Glu Glu Ala Glu Gln Lys Arg Leu Lys Thr Val Leu Glu Leu
145                 150                 155                 160
Gln Tyr Val Leu Asp Lys Leu Gly Asp Asp Glu Val Arg Thr Asp Leu
            165                 170                 175
Lys Gln Gly Leu Asn Gly Val Pro Ile Leu Ser Glu Glu Leu Ser
            180                 185                 190
Leu Leu Asp Glu Phe Tyr Lys Leu Ala Asp Pro Glu Arg Asp Met Ser
            195                 200                 205
Leu Arg Leu Asn Glu Gln Tyr Glu His Ala Ser Ile His Leu Trp Asp
            210                 215                 220
Leu Leu Glu Gly Lys Glu Lys Ser Val Cys Gly Thr Thr Tyr Lys Ala
225                 230                 235                 240
Leu Lys Glu Ile Val Glu Arg Val Phe Gln Ser Asn Tyr Phe Asp Ser
            245                 250                 255
Thr His Asn His Gln Asn Gly Leu Cys Glu Glu Glu Ala Ala Ser
            260                 265                 270
Ala Pro Thr Val Glu Asp Gln Val Ala Glu Ala Glu Pro Glu Pro Ala
            275                 280                 285
Glu Glu Tyr Thr Glu Gln Ser Glu Val Glu Ser Thr Glu Tyr Val Asn
            290                 295                 300
Arg Gln Phe Met Ala Glu Thr Gln Phe Ser Ser Gly Glu Lys Glu Gln
305                 310                 315                 320
Val Asp Glu Trp Thr Val Glu Thr Val Glu Val Val Asn Ser Leu Gln
            325                 330                 335
Gln Gln Pro Gln Ala Ala Ser Pro Ser Val Pro Glu Pro His Ser Leu
            340                 345                 350
Thr Pro Val Ala Gln Ala Asp Pro Leu Val Arg Arg Gln Arg Val Gln
            355                 360                 365
Asp Leu Met Ala Gln Met Gln Gly Pro Tyr Asn Phe Ile Gln Asp Ser
            370                 375                 380
Met Leu Asp Phe Glu Asn Gln Thr Leu Asp Pro Ala Ile Val Ser Ala
385                 390                 395                 400
Gln Pro Met Asn Pro Thr Gln Asn Met Asp Met Pro Gln Leu Val Cys
            405                 410                 415
Pro Pro Val His Ser Glu Ser Arg Leu Ala Gln Pro Asn Gln Val Pro
            420                 425                 430
Val Gln Pro Glu Ala Thr Gln Val Pro Leu Val Ser Ser Thr Ser Glu
            435                 440                 445
Gly Tyr Thr Ala Ser Gln Pro Leu Tyr Gln Pro Ser His Ala Thr Glu
            450                 455                 460
Gln Arg Pro Gln Lys Glu Pro Ile Asp Gln Ile Gln Ala Thr Ile Ser
465                 470                 475                 480
Leu Asn Thr Asp Gln Thr Thr Ala Ser Ser Leu Pro Ala Ala Ser
            485                 490                 495
Gln Pro Gln Val Phe Gln Ala Gly Thr Ser Lys Pro Leu His Ser Ser
            500                 505                 510
```

```
Gly Ile Asn Val Asn Ala Ala Pro Phe Gln Ser Met Gln Thr Val Phe
            515                 520                 525

Asn Met Asn Ala Pro Val Pro Pro Val Asn Glu Pro Glu Thr Leu Lys
        530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
610                 615                 620

Gly Ala Arg Gly Leu Met Asn Gly Tyr Arg Gly Pro Ala Asn Gly Phe
                630                 635                 640
625

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
        660                 665                 670

Tyr Gln Arg Asp Gly Tyr Gln Gln Asn Phe Lys Arg Gly Ser Gly Gln
675                 680                 685

Ser Gly Pro Arg Gly Ala Pro Arg Gly Asn Ile Leu Trp Trp
        690                 695                 700

<210> SEQ ID NO 11
<211> LENGTH: 3306
<212> TYPE: DNA
<213> ORGANISM: Canis familiaris
<220> FEATURE:
<221> NAME/KEY: CDS
<222> LOCATION: (1)..(2040)
<223> OTHER INFORMATION:

<400> SEQUENCE: 11 atg ccg tcg gcc acc agc ctc agc gga agc ggc agc aag tcg tcg ggc      48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg      96
Pro Pro Pro Pro Ser Gly Ser Ser Gly Ser Glu Ala Ala Ala Ala Ala
                20                  25                  30 ggg gcg gcg ggg gcg gcg ggg gcc ggg gcg gct gcg ccc gcc tcc cag     144
Gly Ala Ala Gly Ala Ala Gly Ala Gly Ala Ala Ala Pro Ala Ser Gln
            35                  40                  45 cac ccc gcg acc ggc acc ggc gct gtc cag acc gag gcc atg aag cag     192
His Pro Ala Thr Gly Thr Gly Ala Val Gln Thr Glu Ala Met Lys Gln
        50                  55                  60 atc ctc ggg gtg atc gac aag aaa ctc cgg aac ctg gag aag aaa aag     240
Ile Leu Gly Val Ile Asp Lys Lys Leu Arg Asn Leu Glu Lys Lys Lys
65                  70                  75                  80 ggc aag ctt gat gat tac cag gaa cga atg aac aaa ggg gaa agg ctt     288
Gly Lys Leu Asp Asp Tyr Gln Glu Arg Met Asn Lys Gly Glu Arg Leu
                85                  90                  95 aat caa gat cag ctg gat gcc gta tct aag tac cag gaa gtc aca aat     336
Asn Gln Asp Gln Leu Asp Ala Val Ser Lys Tyr Gln Glu Val Thr Asn
                100                 105                 110 aac ttg gag ttt gca aaa gaa tta cag agg agt ttc atg gca tta agt     384
Asn Leu Glu Phe Ala Lys Glu Leu Gln Arg Ser Phe Met Ala Leu Ser
            115                 120                 125
```

-continued

```
caa gat att cag aaa aca ata aag aag act gca cgt cgg gag cag ctt      432
Gln Asp Ile Gln Lys Thr Ile Lys Lys Thr Ala Arg Arg Glu Gln Leu
    130             135                 140 atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160 cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175 aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190 ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205 ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220 ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240 cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255 act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270 gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285 gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300 aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320 gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335 cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350 act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365 gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380 atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400 cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415 cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430 gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445
```

```
ggg tat aca gca tct caa ccc ttg tac cag cct tct cat gct aca gag   1392
Gly Tyr Thr Ala Ser Gln Pro Leu Tyr Gln Pro Ser His Ala Thr Glu
    450                 455                 460 caa cga cca caa aag gaa cca att gac cag att cag gca aca atc tct   1440
Gln Arg Pro Gln Lys Glu Pro Ile Asp Gln Ile Gln Ala Thr Ile Ser
465                 470                 475                 480 tta aat aca gac cag act aca gcg tca tca tcc ctt ccg gct gct tct   1488
Leu Asn Thr Asp Gln Thr Thr Ala Ser Ser Ser Leu Pro Ala Ala Ser
                    485                 490                 495 cag cct cag gta ttc cag gct ggg aca agc aaa cca tta cat agc agt   1536
Gln Pro Gln Val Phe Gln Ala Gly Thr Ser Lys Pro Leu His Ser Ser
                500                 505                 510 gga atc aat gta aat gca gct cca ttc caa tcc atg caa acg gtg ttc   1584
Gly Ile Asn Val Asn Ala Ala Pro Phe Gln Ser Met Gln Thr Val Phe
            515                 520                 525 aat atg aat gcc cca gtt cct cct gtt aat gaa cca gaa act ttg aaa   1632
Asn Met Asn Ala Pro Val Pro Pro Val Asn Glu Pro Glu Thr Leu Lys
        530                 535                 540 caa caa aat cag tac cag gcc agt tat aac cag agc ttt tct agt cag   1680
Gln Gln Asn Gln Tyr Gln Ala Ser Tyr Asn Gln Ser Phe Ser Ser Gln
545                 550                 555                 560 cct cac caa gta gaa caa aca gac ctt cag caa gaa cag ctt caa aca   1728
Pro His Gln Val Glu Gln Thr Asp Leu Gln Gln Glu Gln Leu Gln Thr
                    565                 570                 575 gtg gtt ggc act tac cat ggt tcc cag gac cag ccc cac caa gtg act   1776
Val Val Gly Thr Tyr His Gly Ser Gln Asp Gln Pro His Gln Val Thr
                580                 585                 590 ggt aac cat cag cag cct ccc cag cag aac act gga ttt cca cgt agc   1824
Gly Asn His Gln Gln Pro Pro Gln Gln Asn Thr Gly Phe Pro Arg Ser
            595                 600                 605 agt cag ccc tat tac aat agt cgt ggt gtg tct cgt ggt ggt tcc cgt   1872
Ser Gln Pro Tyr Tyr Asn Ser Arg Gly Val Ser Arg Gly Gly Ser Arg
        610                 615                 620 ggt gct aga ggc tta atg aat gga tac agg ggc cct gcc aat gga ttc   1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac   1968
Arg Gly Gly Tyr Asp Gly Tyr Arg Pro Ser Phe Ser Asn Thr Pro Asn
                    645                 650                 655 agt ggt tat aca cag tct cag ttc agt gct ccc cgg gac tac tct ggc   2016
Ser Gly Tyr Thr Gln Ser Gln Phe Ser Ala Pro Arg Asp Tyr Ser Gly
                660                 665                 670 tat cag cgg gga tgc cgc aaa tga acactcagca agtgaattaa tctgattcac   2070
Tyr Gln Arg Gly Cys Arg Lys
            675 aggattatgt ttaaacgcca aaaacacact ggccagtgta ccataatatg ttaccagaag   2130 agttattatc tatttgttct ccctttcagg aaacttattg taaagggact gttttcatcc   2190 cataaagaca ggactacaat tgtcagcttt atattacctg gatatggaag gaaactattt   2250 ttattctgca tgttcttcct aagcgtcatc ttgagccttg cacatgatac tcagattcct   2310 caccccttgct taggagtaaa acataataca ctttacaggg tgatatctcc atagttattt   2370 gaagtggctt ggaaaaagca agattaactt ctgacattgg ataaaaatca acaaatcagc   2430 cctagagtta ttcaaatggt aattgacaaa aactaaaata tttcccttcg agaaggagtg   2490 gaatgtggtt tggcagaaca actgcatttc acagctttta cggttaaatt ggagcactaa   2550 acgtttagat gcataccaaa ttatgcatgg gcccttaata taaaaggctg gctaccagct   2610 ttgacacagc actattcatc ctctggccaa acaactgtgg ttaaacaaca catgtaaatt   2670
```

-continued

```
gcttttaac agctgatact ataataagac aaagccaaaa tgcaaaaatt gggctttgat    2730
tggcactttt tgaaaaatat gcaacaaata tgggatgtaa tctggatggc cgcttctgta    2790
cttaatgtga agtatttaga taccttttg aacacttaac agtttcttct gacaatgact    2850
tttgtaagga ttggtactat ctatcattcc ttataatgta cattgtctgt cactaatcct    2910
cagatcttgc tgtattgtca cctaaattgg tacaggtact gatgaaaata tctaatggat    2970
aatcataaca ctcttggtca catgtttttc ctgcagcctg aaggttttta aaagaaaaag    3030
atatcaaatg cctgctgcta ccacccttt aaattgctat cttttgaaaa gcaccagtat    3090
gtgttttaga ttgatttccc tattttaggg aaatgacaga cagtagtttc agttctgatg    3150
gtataagcaa aacaaataaa acatgtttat aaaagttgta tcttgaaaca ctggtgttca    3210
acagctagca gctatgtgg ttcaccccat gcattgttag tgtttcagat tttatggtta    3270
tctccagcag ctgtttctgt agtacttgca tttatc    3306
```

<210> SEQ ID NO 12
<211> LENGTH: 679
<212> TYPE: PRT
<213> ORGANISM: Canis familiaris

<400> SEQUENCE: 12

```
Met Pro Ser Ala Thr Ser Leu Ser Gly Ser Gly Ser Lys Ser Gly
1               5                   10                  15

Pro Pro Pro Pro Ser Gly Ser Gly Ser Glu Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Ala Ala Ser
            260                 265                 270
```

```
Ala Pro Thr Val Glu Asp Gln Val Ala Glu Ala Glu Pro Glu Pro Ala
        275                 280                 285
Glu Glu Tyr Thr Glu Gln Ser Glu Val Glu Ser Thr Glu Tyr Val Asn
        290                 295                 300
Arg Gln Phe Met Ala Glu Thr Gln Phe Ser Ser Gly Glu Lys Glu Gln
305                 310                 315                 320
Val Asp Glu Trp Thr Val Glu Thr Val Glu Val Val Asn Ser Leu Gln
                    325                 330                 335
Gln Gln Pro Gln Ala Ala Ser Pro Ser Val Pro Glu Pro His Ser Leu
            340                 345                 350
Thr Pro Val Ala Gln Ala Asp Pro Leu Val Arg Arg Gln Arg Val Gln
        355                 360                 365
Asp Leu Met Ala Gln Met Gln Gly Pro Tyr Asn Phe Ile Gln Asp Ser
    370                 375                 380
Met Leu Asp Phe Glu Asn Gln Thr Leu Asp Pro Ala Ile Val Ser Ala
385                 390                 395                 400
Gln Pro Met Asn Pro Thr Gln Asn Met Asp Met Pro Gln Leu Val Cys
                    405                 410                 415
Pro Pro Val His Ser Glu Ser Arg Leu Ala Gln Pro Asn Gln Val Pro
            420                 425                 430
Val Gln Pro Glu Ala Thr Gln Val Pro Leu Val Ser Ser Thr Ser Glu
        435                 440                 445
Gly Tyr Thr Ala Ser Gln Pro Leu Tyr Gln Pro Ser His Ala Thr Glu
    450                 455                 460
Gln Arg Pro Gln Lys Glu Pro Ile Asp Gln Ile Gln Ala Thr Ile Ser
465                 470                 475                 480
Leu Asn Thr Asp Gln Thr Thr Ala Ser Ser Leu Pro Ala Ala Ser
                    485                 490                 495
Gln Pro Gln Val Phe Gln Ala Gly Thr Ser Lys Pro Leu His Ser Ser
            500                 505                 510
Gly Ile Asn Val Asn Ala Ala Pro Phe Gln Ser Met Gln Thr Val Phe
        515                 520                 525
Asn Met Asn Ala Pro Val Pro Pro Val Asn Glu Pro Glu Thr Leu Lys
    530                 535                 540
Gln Gln Asn Gln Tyr Gln Ala Ser Tyr Asn Gln Ser Phe Ser Ser Gln
545                 550                 555                 560
Pro His Gln Val Glu Gln Thr Asp Leu Gln Gln Glu Gln Leu Gln Thr
                    565                 570                 575
Val Val Gly Thr Tyr His Gly Ser Gln Asp Gln Pro His Gln Val Thr
            580                 585                 590
Gly Asn His Gln Gln Pro Pro Gln Gln Asn Thr Gly Phe Pro Arg Ser
        595                 600                 605
Ser Gln Pro Tyr Tyr Asn Ser Arg Gly Val Ser Arg Gly Gly Ser Arg
    610                 615                 620
Gly Ala Arg Gly Leu Met Asn Gly Tyr Arg Gly Pro Ala Asn Gly Phe
625                 630                 635                 640
Arg Gly Gly Tyr Asp Gly Tyr Arg Pro Ser Phe Ser Asn Thr Pro Asn
                    645                 650                 655
Ser Gly Tyr Thr Gln Ser Gln Phe Ser Ala Pro Arg Asp Tyr Ser Gly
            660                 665                 670
Tyr Gln Arg Gly Cys Arg Lys
        675
```

<210> SEQ ID NO 13
<211> LENGTH: 2281
<212> TYPE: DNA
<213> ORGANISM: Canis familiaris
<220> FEATURE:
<221> NAME/KEY: CDS
<222> LOCATION: (1)..(2154)
<223> OTHER INFORMATION:

<400> SEQUENCE: 13

| | | | | | | | | | | | | | | | | |
|---|---|---|---|---|---|---|---|---|---|---|---|---|---|---|---|---|
| atg | ccg | tcg | gcc | acc | agc | ctc | agc | gga | agc | ggc | agc | aag | tcg | tcg | ggc | 48 |
| Met | Pro | Ser | Ala | Thr | Ser | Leu | Ser | Gly | Ser | Gly | Ser | Lys | Ser | Ser | Gly | |
| 1 | | | | 5 | | | | | 10 | | | | | 15 | | |

| ccg | ccg | ccc | ccg | tcg | ggt | tcc | tcc | ggg | agc | gag | gcg | gcg | gcg | gcg | gcg | 96 |
|---|---|---|---|---|---|---|---|---|---|---|---|---|---|---|---|---|
| Pro | Pro | Pro | Pro | Ser | Gly | Ser | Ser | Gly | Ser | Glu | Ala | Ala | Ala | Ala | Ala | |
| | | | 20 | | | | | 25 | | | | | 30 | | | |

| ggg | gcg | gcg | ggg | gcg | gcg | ggg | gcc | ggg | gcg | gct | gcg | ccc | gcc | tcc | cag | 144 |
|---|---|---|---|---|---|---|---|---|---|---|---|---|---|---|---|---|
| Gly | Ala | Ala | Gly | Ala | Ala | Gly | Ala | Gly | Ala | Ala | Ala | Pro | Ala | Ser | Gln | |
| | | 35 | | | | | 40 | | | | | 45 | | | | |

| cac | ccc | gcg | acc | ggc | acc | ggc | gct | gtc | cag | acc | gag | gcc | atg | aag | cag | 192 |
|---|---|---|---|---|---|---|---|---|---|---|---|---|---|---|---|---|
| His | Pro | Ala | Thr | Gly | Thr | Gly | Ala | Val | Gln | Thr | Glu | Ala | Met | Lys | Gln | |
| 50 | | | | | 55 | | | | | 60 | | | | | | |

| atc | ctc | ggg | gtg | atc | gac | aag | aaa | ctc | cgg | aac | ctg | gag | aag | aaa | aag | 240 |
|---|---|---|---|---|---|---|---|---|---|---|---|---|---|---|---|---|
| Ile | Leu | Gly | Val | Ile | Asp | Lys | Lys | Leu | Arg | Asn | Leu | Glu | Lys | Lys | Lys | |
| 65 | | | | 70 | | | | | 75 | | | | | 80 | | |

| ggc | aag | ctt | gat | gat | tac | cag | gaa | cga | atg | aac | aaa | ggg | gaa | agg | ctt | 288 |
|---|---|---|---|---|---|---|---|---|---|---|---|---|---|---|---|---|
| Gly | Lys | Leu | Asp | Asp | Tyr | Gln | Glu | Arg | Met | Asn | Lys | Gly | Glu | Arg | Leu | |
| | | | | 85 | | | | | 90 | | | | | 95 | | |

| aat | caa | gat | cag | ctg | gat | gcc | gta | tct | aag | tac | cag | gaa | gtc | aca | aat | 336 |
|---|---|---|---|---|---|---|---|---|---|---|---|---|---|---|---|---|
| Asn | Gln | Asp | Gln | Leu | Asp | Ala | Val | Ser | Lys | Tyr | Gln | Glu | Val | Thr | Asn | |
| | | | 100 | | | | | 105 | | | | | 110 | | | |

| aac | ttg | gag | ttt | gca | aaa | gaa | tta | cag | agg | agt | ttc | atg | gca | tta | agt | 384 |
|---|---|---|---|---|---|---|---|---|---|---|---|---|---|---|---|---|
| Asn | Leu | Glu | Phe | Ala | Lys | Glu | Leu | Gln | Arg | Ser | Phe | Met | Ala | Leu | Ser | |
| | | 115 | | | | | 120 | | | | | 125 | | | | |

| caa | gat | att | cag | aaa | aca | ata | aag | aag | act | gca | cgt | cgg | gag | cag | ctt | 432 |
|---|---|---|---|---|---|---|---|---|---|---|---|---|---|---|---|---|
| Gln | Asp | Ile | Gln | Lys | Thr | Ile | Lys | Lys | Thr | Ala | Arg | Arg | Glu | Gln | Leu | |
| | | 130 | | | | | 135 | | | | | 140 | | | | |

| atg | aga | gag | gaa | gcg | gaa | caa | aaa | cgt | tta | aaa | act | gta | ctt | gag | ctc | 480 |
|---|---|---|---|---|---|---|---|---|---|---|---|---|---|---|---|---|
| Met | Arg | Glu | Glu | Ala | Glu | Gln | Lys | Arg | Leu | Lys | Thr | Val | Leu | Glu | Leu | |
| 145 | | | | 150 | | | | | 155 | | | | | 160 | | |

| cag | tat | gtt | ttg | gac | aaa | ttg | gga | gat | gat | gaa | gtg | aga | act | gac | ctg | 528 |
|---|---|---|---|---|---|---|---|---|---|---|---|---|---|---|---|---|
| Gln | Tyr | Val | Leu | Asp | Lys | Leu | Gly | Asp | Asp | Glu | Val | Arg | Thr | Asp | Leu | |
| | | | 165 | | | | | 170 | | | | | 175 | | | |

| aag | caa | ggt | ttg | aat | gga | gtg | cca | ata | ttg | tct | gaa | gaa | gaa | ttg | tcg | 576 |
|---|---|---|---|---|---|---|---|---|---|---|---|---|---|---|---|---|
| Lys | Gln | Gly | Leu | Asn | Gly | Val | Pro | Ile | Leu | Ser | Glu | Glu | Glu | Leu | Ser | |
| | | | 180 | | | | | 185 | | | | | 190 | | | |

| ttg | ttg | gat | gaa | ttc | tac | aaa | tta | gca | gac | cct | gaa | cgg | gac | atg | agc | 624 |
|---|---|---|---|---|---|---|---|---|---|---|---|---|---|---|---|---|
| Leu | Leu | Asp | Glu | Phe | Tyr | Lys | Leu | Ala | Asp | Pro | Glu | Arg | Asp | Met | Ser | |
| | | 195 | | | | | 200 | | | | | 205 | | | | |

| ttg | agg | ttg | aat | gag | cag | tat | gaa | cat | gct | tcc | att | cac | ctg | tgg | gac | 672 |
|---|---|---|---|---|---|---|---|---|---|---|---|---|---|---|---|---|
| Leu | Arg | Leu | Asn | Glu | Gln | Tyr | Glu | His | Ala | Ser | Ile | His | Leu | Trp | Asp | |
| | | 210 | | | | | 215 | | | | | 220 | | | | |

| ttg | ctg | gaa | gga | aag | gaa | aag | tct | gta | tgt | gga | aca | acc | tat | aaa | gca | 720 |
|---|---|---|---|---|---|---|---|---|---|---|---|---|---|---|---|---|
| Leu | Leu | Glu | Gly | Lys | Glu | Lys | Ser | Val | Cys | Gly | Thr | Thr | Tyr | Lys | Ala | |
| 225 | | | | 230 | | | | | 235 | | | | | 240 | | |

| cta | aag | gaa | att | gtt | gag | cgt | gtt | ttc | cag | tca | aat | tac | ttt | gac | agc | 768 |
|---|---|---|---|---|---|---|---|---|---|---|---|---|---|---|---|---|
| Leu | Lys | Glu | Ile | Val | Glu | Arg | Val | Phe | Gln | Ser | Asn | Tyr | Phe | Asp | Ser | |
| | | | | 245 | | | | | 250 | | | | | 255 | | |

| act | cac | aac | cac | cag | aat | ggg | cta | tgt | gag | gaa | gaa | gag | gca | gcc | tca | 816 |
|---|---|---|---|---|---|---|---|---|---|---|---|---|---|---|---|---|
| Thr | His | Asn | His | Gln | Asn | Gly | Leu | Cys | Glu | Glu | Glu | Glu | Ala | Ala | Ser | |
| | | | 260 | | | | | 265 | | | | | 270 | | | |

| gca | cct | aca | gtt | gaa | gac | cag | gta | gct | gaa | gct | gag | cct | gag | cca | gca | 864 |

```
                Ala Pro Thr Val Glu Asp Gln Val Ala Glu Ala Glu Pro Glu Pro Ala
                                275                 280                 285 gaa gaa tac act gaa caa agt gaa gtt gaa tca aca gag tat gta aat              912
Glu Glu Tyr Thr Glu Gln Ser Glu Val Glu Ser Thr Glu Tyr Val Asn
290                 295                 300 aga caa ttt atg gca gaa aca cag ttc agc agt ggt gaa aag gag cag              960
Arg Gln Phe Met Ala Glu Thr Gln Phe Ser Ser Gly Glu Lys Glu Gln
305                 310                 315                 320 gta gat gag tgg acg gtc gaa aca gtg gag gtg gtg aat tca ctc cag             1008
Val Asp Glu Trp Thr Val Glu Thr Val Glu Val Val Asn Ser Leu Gln
                325                 330                 335 cag caa cct cag gct gcg tct cct tca gta cca gag ccc cac tct ttg             1056
Gln Gln Pro Gln Ala Ala Ser Pro Ser Val Pro Glu Pro His Ser Leu
            340                 345                 350 act ccg gtg gct cag gca gat ccc ctt gtg aga aga cag cga gtc cag             1104
Thr Pro Val Ala Gln Ala Asp Pro Leu Val Arg Arg Gln Arg Val Gln
        355                 360                 365 gac ctt atg gcg cag atg cag ggg ccc tat aat ttc ata cag gat tca             1152
Asp Leu Met Ala Gln Met Gln Gly Pro Tyr Asn Phe Ile Gln Asp Ser
370                 375                 380 atg ctg gat ttt gaa aac cag aca ctc gat cct gcc att gta tct gca             1200
Met Leu Asp Phe Glu Asn Gln Thr Leu Asp Pro Ala Ile Val Ser Ala
385                 390                 395                 400 cag cct atg aat ccg aca caa aac atg gac atg ccc cag ctg gtt tgc             1248
Gln Pro Met Asn Pro Thr Gln Asn Met Asp Met Pro Gln Leu Val Cys
                405                 410                 415 cct cca gtt cat tct gaa tct aga ctt gct caa cct aat caa gtt cct             1296
Pro Pro Val His Ser Glu Ser Arg Leu Ala Gln Pro Asn Gln Val Pro
            420                 425                 430 gta caa cca gaa gct aca cag gtt cct ttg gtt tca tcc aca agt gag             1344
Val Gln Pro Glu Ala Thr Gln Val Pro Leu Val Ser Ser Thr Ser Glu
        435                 440                 445 ggg tat aca gca tct caa ccc ttg tac cag cct tct cat gct aca gag             1392
Gly Tyr Thr Ala Ser Gln Pro Leu Tyr Gln Pro Ser His Ala Thr Glu
450                 455                 460 caa cga cca caa aag gaa cca att gac cag att cag gca aca atc tct             1440
Gln Arg Pro Gln Lys Glu Pro Ile Asp Gln Ile Gln Ala Thr Ile Ser
465                 470                 475                 480 tta aat aca gac cag act aca gcg tca tca tcc ctt ccg gct gct tct             1488
Leu Asn Thr Asp Gln Thr Thr Ala Ser Ser Ser Leu Pro Ala Ala Ser
                485                 490                 495 cag cct cag gta ttc cag gct ggg aca agc aaa cca tta cat agc agt             1536
Gln Pro Gln Val Phe Gln Ala Gly Thr Ser Lys Pro Leu His Ser Ser
            500                 505                 510 gga atc aat gta aat gca gct cca ttc caa tcc atg caa acg gtg ttc             1584
Gly Ile Asn Val Asn Ala Ala Pro Phe Gln Ser Met Gln Thr Val Phe
        515                 520                 525 aat atg aat gcc cca gtt cct cct gtt aat gaa cca gaa act ttg aaa             1632
Asn Met Asn Ala Pro Val Pro Pro Val Asn Glu Pro Glu Thr Leu Lys
530                 535                 540 caa caa aat cag tac cag gcc agt tat aac cag agc ttt tct agt cag             1680
Gln Gln Asn Gln Tyr Gln Ala Ser Tyr Asn Gln Ser Phe Ser Ser Gln
545                 550                 555                 560 cct cac caa gta gaa caa aca gac ctt cag caa gaa cag ctt caa aca             1728
Pro His Gln Val Glu Gln Thr Asp Leu Gln Gln Glu Gln Leu Gln Thr
                565                 570                 575 gtg gtt ggc act tac cat ggt tcc cag gac cag ccc cac caa gtg act             1776
Val Val Gly Thr Tyr His Gly Ser Gln Asp Gln Pro His Gln Val Thr
            580                 585                 590 ggt aac cat cag cag cct ccc cag cag aac act gga ttt cca cgt agc             1824
```

```
Gly Asn His Gln Gln Pro Pro Gln Gln Asn Thr Gly Phe Pro Arg Ser
            595                 600                 605 agt cag ccc tat tac aat agt cgt ggt gtg tct cgt ggt ggt tcc cgt       1872
Ser Gln Pro Tyr Tyr Asn Ser Arg Gly Val Ser Arg Gly Gly Ser Arg
    610                 615                 620 ggt gct aga ggc tta atg aat gga tac agg ggc cct gcc aat gga ttc       1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac       1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc       2016
Ser Gly Tyr Thr Gln Ser Gln Phe Ser Ala Pro Arg Asp Tyr Ser Gly
            660                 665                 670 tat cag cgg gat gga tat cag cag aat ttc aag cga ggc tct ggg cag       2064
Tyr Gln Arg Asp Gly Tyr Gln Gln Asn Phe Lys Arg Gly Ser Gly Gln
        675                 680                 685 agt gga cca cgg gga gcc cca cga ggt cgt gga ggg ccc cca aga ccc       2112
Ser Gly Pro Arg Gly Ala Pro Arg Gly Arg Gly Gly Pro Pro Arg Pro
690                 695                 700 aac aga ggg atg ccg caa atg aac act cag caa gtg aat taa               2154
Asn Arg Gly Met Pro Gln Met Asn Thr Gln Gln Val Asn
705                 710                 715 tctgattcac aggattatgt ttaaacgcca aaaacacact ggccagtgta ccataatatg     2214
ttaccagaag agttattatc tatttggact gttttcatcc cataaagaca ggactacaat    2274
tgtcagc                                                               2281

<210> SEQ ID NO 14
<211> LENGTH: 717
<212> TYPE: PRT
<213> ORGANISM: Canis familiaris

<400> SEQUENCE: 14

Met Pro Ser Ala Thr Ser Leu Ser Gly Ser Gly Ser Lys Ser Ser Gly
1               5                   10                  15

Pro Pro Pro Ser Gly Ser Ser Gly Ser Glu Ala Ala Ala Ala
            20                  25                  30

Gly Ala Ala Gly Ala Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190
```

-continued

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
        210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Ala Ala Ser
                260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
        290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
        340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
        370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
                420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
        450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
        500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
        530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Gln Leu Gln Thr
                565                 570                 575

Val Val Gly Thr Tyr His Gly Ser Gln Asp Gln Pro His Gln Val Thr
                580                 585                 590

Gly Asn His Gln Gln Pro Pro Gln Gln Asn Thr Gly Phe Pro Arg Ser
                595                 600                 605

Ser Gln Pro Tyr Tyr Asn Ser Arg Gly Val Ser Arg Gly Gly Ser Arg

```
                    610                  615                  620
Gly Ala Arg Gly Leu Met Asn Gly Tyr Arg Gly Pro Ala Asn Gly Phe
625                 630                  635                  640

Arg Gly Gly Tyr Asp Gly Tyr Arg Pro Ser Phe Ser Asn Thr Pro Asn
                645                  650                  655

Ser Gly Tyr Thr Gln Ser Gln Phe Ser Ala Pro Arg Asp Tyr Ser Gly
            660                  665                  670

Tyr Gln Arg Asp Gly Tyr Gln Gln Asn Phe Lys Arg Gly Ser Gly Gln
        675                  680                  685

Ser Gly Pro Arg Gly Ala Pro Arg Gly Arg Gly Pro Pro Arg Pro
    690                  695                  700

Asn Arg Gly Met Pro Gln Met Asn Thr Gln Gln Val Asn
705                 710                  715

<210> SEQ ID NO 15
<211> LENGTH: 3386
<212> TYPE: DNA
<213> ORGANISM: Bos taurus
<220> FEATURE:
<221> NAME/KEY: CDS
<222> LOCATION: (82)..(2208)
<223> OTHER INFORMATION:

<400> SEQUENCE: 15
```

| | | |
|---|---|---|
| cgcgtctcgc cccgtccacc gattgactcg ccgctcttgt ccttcctccc gctctttctt | | 60 |
| ctctccccctt acggtttcaa g atg cct tcg gcc acc agc cac agc gga agc<br>                                Met Pro Ser Ala Thr Ser His Ser Gly Ser<br>                                1             5                   10 | | 111 |

```
ggc agc aag tcg tcc gga ccg cca ccg ccg tcg ggt tcc tcc ggg aat          159
Gly Ser Lys Ser Ser Gly Pro Pro Pro Pro Ser Gly Ser Ser Gly Asn
        15                  20                  25 gag gcg ggg gcc ggg gcc gcc gcg ccg gct tcc caa cac ccc atg acc          207
Glu Ala Gly Ala Gly Ala Ala Ala Pro Ala Ser Gln His Pro Met Thr
            30                  35                  40 ggc acc ggg gct gtc cag acc gag gcc atg aag cag att ctc ggg gtg          255
Gly Thr Gly Ala Val Gln Thr Glu Ala Met Lys Gln Ile Leu Gly Val
        45                  50                  55 atc gac aag aaa ctt cgg aac ctg gag aag aaa aag ggc aag ctt gat          303
Ile Asp Lys Lys Leu Arg Asn Leu Glu Lys Lys Lys Gly Lys Leu Asp
    60                  65                  70 gat tat cag gaa cga atg aac aaa ggg gaa agg ctt aat caa gat cag          351
Asp Tyr Gln Glu Arg Met Asn Lys Gly Glu Arg Leu Asn Gln Asp Gln
75                  80                  85                  90 ctg gat gcc gtg tct aag tac cag gaa gtc aca aat aac ttg gag ttt          399
Leu Asp Ala Val Ser Lys Tyr Gln Glu Val Thr Asn Asn Leu Glu Phe
                95                  100                 105 gca aaa gaa tta cag agg agt ttc atg gca tta agc caa gat att cag          447
Ala Lys Glu Leu Gln Arg Ser Phe Met Ala Leu Ser Gln Asp Ile Gln
            110                 115                 120 aaa aca ata aag aag aca gca cgt cgg gag cag ctt atg aga gag gaa          495
Lys Thr Ile Lys Lys Thr Ala Arg Arg Glu Gln Leu Met Arg Glu Glu
        125                 130                 135 gct gaa cag aaa cgt tta aaa aca gta ctt gag ctg cag tat gtt ttg          543
Ala Glu Gln Lys Arg Leu Lys Thr Val Leu Glu Leu Gln Tyr Val Leu
    140                 145                 150 gac aaa cta gga gat gat gaa gtg aga act gac ctg aag caa ggt ttg          591
Asp Lys Leu Gly Asp Asp Glu Val Arg Thr Asp Leu Lys Gln Gly Leu
155                 160                 165                 170 aat gga gtg cca ata ttg tct gaa gag gag ttg tcg ttg tta gat gag          639
Asn Gly Val Pro Ile Leu Ser Glu Glu Glu Leu Ser Leu Leu Asp Glu
```

-continued

```
                        175                 180                      185
ttc tac aaa tta gca gac cct gaa cga gac atg agc ttg agg ttg aat         687
Phe Tyr Lys Leu Ala Asp Pro Glu Arg Asp Met Ser Leu Arg Leu Asn
            190                 195                 200 gag cag tat gaa cat gcc tcc att cac ctg tgg gac ttg ctg gaa gga         735
Glu Gln Tyr Glu His Ala Ser Ile His Leu Trp Asp Leu Leu Glu Gly
        205                 210                 215 aag gaa aaa cct gta tgt gga aca act tat aaa gct cta aag gaa att         783
Lys Glu Lys Pro Val Cys Gly Thr Thr Tyr Lys Ala Leu Lys Glu Ile
220                 225                 230 gtt gag cgt gtt ttc cag tca aac tac ttt gac agc acc cac aac cac         831
Val Glu Arg Val Phe Gln Ser Asn Tyr Phe Asp Ser Thr His Asn His
235                 240                 245                 250 cag aat ggt ctg tgt gag gaa gag gca gcc tca gca cct aca gtt             879
Gln Asn Gly Leu Cys Glu Glu Glu Ala Ala Ser Ala Pro Thr Val
                255                 260                 265 gaa gac cag gca gct gaa gct gaa cct gag cca gtg gaa gaa tat act         927
Glu Asp Gln Ala Ala Glu Ala Glu Pro Glu Pro Val Glu Glu Tyr Thr
            270                 275                 280 gaa caa aat gag gtt gaa tca aca gag tat gta aat aga caa ttt atg         975
Glu Gln Asn Glu Val Glu Ser Thr Glu Tyr Val Asn Arg Gln Phe Met
        285                 290                 295 gca gaa aca cag ttc agc agt ggt gaa aag gag cag gta gat gat tgg        1023
Ala Glu Thr Gln Phe Ser Ser Gly Glu Lys Glu Gln Val Asp Asp Trp
300                 305                 310 aca gtt gaa aca gtt gag gtg gta aat tca ctc cag cag caa cct cag        1071
Thr Val Glu Thr Val Glu Val Val Asn Ser Leu Gln Gln Gln Pro Gln
315                 320                 325                 330 gct gca tct cct tca gta cca gaa ccc cac tct ttg acc cca gtg gct        1119
Ala Ala Ser Pro Ser Val Pro Glu Pro His Ser Leu Thr Pro Val Ala
                335                 340                 345 caa gcc gat ccc ctc gtg aga aga cag cga gta cag gac ctt atg gca        1167
Gln Ala Asp Pro Leu Val Arg Arg Gln Arg Val Gln Asp Leu Met Ala
            350                 355                 360 caa atg cag ggg ccc tat aat ttc ata cag gat tca atg ttg gat ttt        1215
Gln Met Gln Gly Pro Tyr Asn Phe Ile Gln Asp Ser Met Leu Asp Phe
        365                 370                 375 gaa aac cag aca ctt gat cct gcc att gta tct gca cag ccg atg aat        1263
Glu Asn Gln Thr Leu Asp Pro Ala Ile Val Ser Ala Gln Pro Met Asn
380                 385                 390 cca gca cag aac atg gac ata ccc cag ctg gtt tgc cct cca gtt cat        1311
Pro Ala Gln Asn Met Asp Ile Pro Gln Leu Val Cys Pro Pro Val His
395                 400                 405                 410 tct gaa tct aga ctt gct caa cct aat caa gtt tct gta cag cca gaa        1359
Ser Glu Ser Arg Leu Ala Gln Pro Asn Gln Val Ser Val Gln Pro Glu
                415                 420                 425 gct aca cag gtt cct ttg gtt tca tcc aca agt gag gga tat aca gca        1407
Ala Thr Gln Val Pro Leu Val Ser Ser Thr Ser Glu Gly Tyr Thr Ala
            430                 435                 440 tct caa ccc ttg tac caa cct tct cat gct act gac caa cga cca caa        1455
Ser Gln Pro Leu Tyr Gln Pro Ser His Ala Thr Asp Gln Arg Pro Gln
        445                 450                 455 aag gaa ccg att gat cag att cag gcg acg atc tct tta aat aca gac        1503
Lys Glu Pro Ile Asp Gln Ile Gln Ala Thr Ile Ser Leu Asn Thr Asp
460                 465                 470 cag act aca gca tca tca tcc ctt cct gct gct tct cag cct caa gtg        1551
Gln Thr Thr Ala Ser Ser Ser Leu Pro Ala Ala Ser Gln Pro Gln Val
475                 480                 485                 490 ttc cag gct ggg aca agc aaa cct tta cat agc agt gga atc aat gta        1599
Phe Gln Ala Gly Thr Ser Lys Pro Leu His Ser Ser Gly Ile Asn Val
```

```
                495              500              505
aat gca gct cca ttc caa tcc atg caa acg gta ttc aat atg aat gcc    1647
Asn Ala Ala Pro Phe Gln Ser Met Gln Thr Val Phe Asn Met Asn Ala
            510              515              520 cca gtt cct cct gtt aat gaa cca gaa act tta aaa cag caa aat cag    1695
Pro Val Pro Pro Val Asn Glu Pro Glu Thr Leu Lys Gln Gln Asn Gln
        525              530              535 tac cag gcc agt tac aac cag agc ttt tcc agt cag cct cac caa gta    1743
Tyr Gln Ala Ser Tyr Asn Gln Ser Phe Ser Ser Gln Pro His Gln Val
        540              545              550 gaa caa aca gag ctt cag caa gaa cag ctt caa aca gtg gtt ggc act    1791
Glu Gln Thr Glu Leu Gln Gln Glu Gln Leu Gln Thr Val Val Gly Thr
555              560              565              570 tat cat ggt tct cag gac cag ccc cat caa gtg act ggt aac cac cag    1839
Tyr His Gly Ser Gln Asp Gln Pro His Gln Val Thr Gly Asn His Gln
            575              580              585 cag cct cct cag cag aac act gga ttt cca cgt agc aat cag ccc tat    1887
Gln Pro Pro Gln Gln Asn Thr Gly Phe Pro Arg Ser Asn Gln Pro Tyr
            590              595              600 tac aac agt cgt ggt gtg tct cgt gga ggt tcc cgt ggt gct aga ggc    1935
Tyr Asn Ser Arg Gly Val Ser Arg Gly Gly Ser Arg Gly Ala Arg Gly
            605              610              615 ttg atg aat gga tac aga gga cct gct aat gga ttc aga gga gga tat    1983
Leu Met Asn Gly Tyr Arg Gly Pro Ala Asn Gly Phe Arg Gly Gly Tyr
        620              625              630 gat ggt tac cgc cct tca ttc tct act aac act cca aac agt ggt tat    2031
Asp Gly Tyr Arg Pro Ser Phe Ser Thr Asn Thr Pro Asn Ser Gly Tyr
635              640              645              650 aca caa tct caa ttc agt gct ccc cgg gac tac tct ggc tat cag cgg    2079
Thr Gln Ser Gln Phe Ser Ala Pro Arg Asp Tyr Ser Gly Tyr Gln Arg
            655              660              665 gat gga tat cag cag aat ttc aag cga ggc tct ggg cag agt gga cca    2127
Asp Gly Tyr Gln Gln Asn Phe Lys Arg Gly Ser Gly Gln Ser Gly Pro
            670              675              680 cgg gga gcc cca cga ggt cgt gga ggg ccc cca aga ccc aac aga ggg    2175
Arg Gly Ala Pro Arg Gly Arg Gly Gly Pro Pro Arg Pro Asn Arg Gly
            685              690              695 atg ccg caa atg aac act cag caa gtg aat taa tctgattcac aggattatgt   2228
Met Pro Gln Met Asn Thr Gln Gln Val Asn
    700              705 ttaatcgcca aaacacact ggccagtgta ccataatatg ttaccagaag agttattatc   2288
tatttgttct cccttccagg aaacttattg taaagggact gttttcatcc cataaagaca   2348
ggactacaat tgtcagcttt atattacctg gatatggaag gaaactatttt ttactctgca  2408 tgttctgtcc taagcgtcat cttgagcctt gcacatgata ctcagattcc tcacccttgc   2468
ttaggagtaa aacataatat actttaatgg ggtgatatct ccatagttat ttgaagtggc   2528
ttggataaag caagactgac ttctgacatt ggataaaatc tacaaatcag ccctagagtc   2588
attcagtggt aactgacaaa actaaaatat ttcccttgaa aggaagatgg aaggagtgga   2648
gtgtggtttg gcagaacaac tgcatttcac agcttttcca cttaaattgg agcactgaac   2708
atttagatgc ataccgaatt atgcatgggc cctaatcaca cagacaaggc tggtgccagc   2768
cttaggcttg acacggcagt gttcacccctc tggccagacg actgtggttc aagacacatg   2828
taaattgctt tttaacagct gatactgtat aagacaaagc caaaatgcaa aattaggctt   2888
tgattggcac ttttcgaaaa atatgcaaca attaagggat ataatctgga tggccgcttc   2948
tgtacttaat gtgaaatatt tagataccctt tcaaacactt aacagtttct ttgacaatga   3008
```

```
gttttgtaag gattggtagt aaatatcatt ccttatgacg tacattgtct gtcactaatc    3068
cttggatctt gctgtattgt cacctaaatt ggtacaggta ctgatgaaaa tctaatggat    3128
aatcataaca ctcttggtta catgttttc ctgcagcctg aaagttttta taagaaaaag    3188
acatcaaatg cctgctgctg ccaccctttt aaattgctat cttttgaaaa gcaccagtat    3248
gtgttttaga ttgatttccc tattttaggg aaatgacagt cagtagtttc acttctgatg    3308
gtataagcaa acaaataaaa catgtttata aaaaaaaaaa aaaaaaaaaa aaaaaaaaaa    3368
aaaaaaaaaa aaaaaaaa                                                  3386

<210> SEQ ID NO 16
<211> LENGTH: 708
<212> TYPE: PRT
<213> ORGANISM: Bos taurus

<400> SEQUENCE: 16

Met Pro Ser Ala Thr Ser His Ser Gly Ser Gly Ser Lys Ser Ser Gly
 1               5                  10                  15

Pro Pro Pro Pro Ser Gly Ser Ser Gly Asn Glu Ala Gly Ala Gly Ala
            20                  25                  30

Ala Ala Pro Ala Ser Gln His Pro Met Thr Gly Thr Gly Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Glu Val Arg Thr Asp Leu Lys Gln Gly Leu Asn Gly Val Pro Ile Leu
                165                 170                 175

Ser Glu Glu Glu Leu Ser Leu Leu Asp Glu Phe Tyr Lys Leu Ala Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Ala Ala Glu
            260                 265                 270

Ala Glu Pro Glu Pro Val Glu Glu Tyr Thr Gln Asn Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Asp Trp Thr Val Glu Thr Val Glu
```

```
            305                 310                 315                 320
Val Val Asn Ser Leu Gln Gln Pro Gln Ala Ala Ser Pro Ser Val
                325                 330                 335

Pro Glu Pro His Ser Leu Thr Pro Val Ala Gln Ala Asp Pro Leu Val
                340                 345                 350

Arg Arg Gln Arg Val Gln Asp Leu Met Ala Gln Met Gln Gly Pro Tyr
                355                 360                 365

Asn Phe Ile Gln Asp Ser Met Leu Asp Phe Glu Asn Gln Thr Leu Asp
370                 375                 380

Pro Ala Ile Val Ser Ala Gln Pro Met Asn Pro Ala Gln Asn Met Asp
385                 390                 395                 400

Ile Pro Gln Leu Val Cys Pro Pro Val His Ser Glu Ser Arg Leu Ala
                405                 410                 415

Gln Pro Asn Gln Val Ser Val Gln Pro Glu Ala Thr Gln Val Pro Leu
                420                 425                 430

Val Ser Ser Thr Ser Glu Gly Tyr Thr Ala Ser Gln Pro Leu Tyr Gln
                435                 440                 445

Pro Ser His Ala Thr Asp Gln Arg Pro Gln Lys Glu Pro Ile Asp Gln
                450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
                500                 505                 510

Ser Met Gln Thr Val Phe Asn Met Asn Ala Pro Val Pro Pro Val Asn
                515                 520                 525

Glu Pro Glu Thr Leu Lys Gln Gln Asn Gln Tyr Gln Ala Ser Tyr Asn
                530                 535                 540

Gln Ser Phe Ser Ser Gln Pro His Gln Val Glu Gln Thr Glu Leu Gln
545                 550                 555                 560

Gln Glu Gln Leu Gln Thr Val Val Gly Thr Tyr His Gly Ser Gln Asp
                565                 570                 575

Gln Pro His Gln Val Thr Gly Asn His Gln Gln Pro Pro Gln Gln Asn
                580                 585                 590

Thr Gly Phe Pro Arg Ser Asn Gln Pro Tyr Tyr Asn Ser Arg Gly Val
                595                 600                 605

Ser Arg Gly Gly Ser Arg Gly Ala Arg Gly Leu Met Asn Gly Tyr Arg
                610                 615                 620

Gly Pro Ala Asn Gly Phe Arg Gly Gly Tyr Asp Gly Tyr Arg Pro Ser
625                 630                 635                 640

Phe Ser Thr Asn Thr Pro Asn Ser Gly Tyr Thr Gln Ser Gln Phe Ser
                645                 650                 655

Ala Pro Arg Asp Tyr Ser Gly Tyr Gln Arg Asp Gly Tyr Gln Gln Asn
                660                 665                 670

Phe Lys Arg Gly Ser Gly Gln Ser Gly Pro Arg Gly Ala Pro Arg Gly
                675                 680                 685

Arg Gly Gly Pro Pro Arg Pro Asn Arg Gly Met Pro Gln Met Asn Thr
                690                 695                 700

Gln Gln Val Asn
705

<210> SEQ ID NO 17
<211> LENGTH: 3150
```

```
<212> TYPE: DNA
<213> ORGANISM: Equus caballus
<220> FEATURE:
<221> NAME/KEY: CDS
<222> LOCATION: (1)..(1917)
<223> OTHER INFORMATION:

<400> SEQUENCE: 17
```

| | | | | | | | | | | | | | | | | |
|---|---|---|---|---|---|---|---|---|---|---|---|---|---|---|---|---|
| atg | gag | ggc | aag | ctc | gat | gat | tac | caa | gag | cga | atg | aac | aaa | gga | gaa | 48 |
| Met | Glu | Gly | Lys | Leu | Asp | Asp | Tyr | Gln | Glu | Arg | Met | Asn | Lys | Gly | Glu | |
| 1 | | | | 5 | | | | | 10 | | | | | 15 | | |
| agg | ctt | aat | cag | gat | cag | ctg | gat | gct | gtg | tct | aag | tac | cag | gaa | gtc | 96 |
| Arg | Leu | Asn | Gln | Asp | Gln | Leu | Asp | Ala | Val | Ser | Lys | Tyr | Gln | Glu | Val | |
| | | | 20 | | | | | 25 | | | | | 30 | | | |
| aca | aat | aac | ttg | gag | ttt | gcg | aaa | gaa | ttg | cag | agg | agt | ttc | atg | gcg | 144 |
| Thr | Asn | Asn | Leu | Glu | Phe | Ala | Lys | Glu | Leu | Gln | Arg | Ser | Phe | Met | Ala | |
| | | 35 | | | | | 40 | | | | | 45 | | | | |
| ttg | agt | cag | gat | att | cag | aaa | aca | ata | aag | aag | acg | gca | cgt | cgg | gag | 192 |
| Leu | Ser | Gln | Asp | Ile | Gln | Lys | Thr | Ile | Lys | Lys | Thr | Ala | Arg | Arg | Glu | |
| 50 | | | | | 55 | | | | | 60 | | | | | | |
| cag | ctt | atg | aga | gaa | gaa | gct | gaa | cag | aaa | cgt | tta | aaa | act | gta | ctt | 240 |
| Gln | Leu | Met | Arg | Glu | Glu | Ala | Glu | Gln | Lys | Arg | Leu | Lys | Thr | Val | Leu | |
| 65 | | | | | 70 | | | | | 75 | | | | | 80 | |
| gag | ctg | cag | tat | gtt | ttg | gac | aaa | ttg | gga | gat | gaa | gaa | gtg | cga | act | 288 |
| Glu | Leu | Gln | Tyr | Val | Leu | Asp | Lys | Leu | Gly | Asp | Glu | Glu | Val | Arg | Thr | |
| | | | | 85 | | | | | 90 | | | | | 95 | | |
| gac | ctg | aaa | caa | ggt | ttg | aat | gga | gtg | cca | ata | ctc | tct | gaa | gaa | gag | 336 |
| Asp | Leu | Lys | Gln | Gly | Leu | Asn | Gly | Val | Pro | Ile | Leu | Ser | Glu | Glu | Glu | |
| | | | | 100 | | | | | 105 | | | | | 110 | | |
| ttg | tcg | ctg | ttg | gat | gag | ttc | tac | aag | tta | gca | gac | cct | gta | cgg | gac | 384 |
| Leu | Ser | Leu | Leu | Asp | Glu | Phe | Tyr | Lys | Leu | Ala | Asp | Pro | Val | Arg | Asp | |
| | | | 115 | | | | | 120 | | | | | 125 | | | |
| atg | agc | ttg | agg | ttg | aat | gag | cag | tat | gag | cat | gcc | tcc | att | cac | ctg | 432 |
| Met | Ser | Leu | Arg | Leu | Asn | Glu | Gln | Tyr | Glu | His | Ala | Ser | Ile | His | Leu | |
| | | 130 | | | | | 135 | | | | | 140 | | | | |
| tgg | gac | ttg | ctg | gaa | ggg | aag | gaa | aaa | tct | gtc | tgt | gga | aca | acc | tat | 480 |
| Trp | Asp | Leu | Leu | Glu | Gly | Lys | Glu | Lys | Ser | Val | Cys | Gly | Thr | Thr | Tyr | |
| 145 | | | | | 150 | | | | | 155 | | | | | 160 | |
| aaa | gct | ctg | agg | gaa | att | gtt | gag | cgt | gtt | ttc | cag | tcc | aac | tac | ttt | 528 |
| Lys | Ala | Leu | Arg | Glu | Ile | Val | Glu | Arg | Val | Phe | Gln | Ser | Asn | Tyr | Phe | |
| | | | | 165 | | | | | 170 | | | | | 175 | | |
| gac | agc | acc | cac | aac | cac | cag | aat | ggg | ctc | tgt | gag | gag | gaa | gag | gct | 576 |
| Asp | Ser | Thr | His | Asn | His | Gln | Asn | Gly | Leu | Cys | Glu | Glu | Glu | Glu | Ala | |
| | | | | 180 | | | | | 185 | | | | | 190 | | |
| acc | tca | gct | cca | aca | gct | gaa | gac | cag | gga | gct | gaa | gct | gaa | cct | gag | 624 |
| Thr | Ser | Ala | Pro | Thr | Ala | Glu | Asp | Gln | Gly | Ala | Glu | Ala | Glu | Pro | Glu | |
| | | | 195 | | | | | 200 | | | | | 205 | | | |
| cca | gca | gaa | gaa | tac | act | gaa | caa | agt | gaa | gtt | gaa | tca | aca | gag | tat | 672 |
| Pro | Ala | Glu | Glu | Tyr | Thr | Glu | Gln | Ser | Glu | Val | Glu | Ser | Thr | Glu | Tyr | |
| | | 210 | | | | | 215 | | | | | 220 | | | | |
| gta | aat | aga | cag | ttt | atg | gca | gaa | gcg | cag | ttc | agt | ggt | gag | aag | gag | 720 |
| Val | Asn | Arg | Gln | Phe | Met | Ala | Glu | Ala | Gln | Phe | Ser | Gly | Glu | Lys | Glu | |
| 225 | | | | | 230 | | | | | 235 | | | | | 240 | |
| cag | gtg | gat | gag | tgg | aca | gtc | gag | acg | gtc | gag | gtg | gta | aat | tca | ctc | 768 |
| Gln | Val | Asp | Glu | Trp | Thr | Val | Glu | Thr | Val | Glu | Val | Val | Asn | Ser | Leu | |
| | | | | 245 | | | | | 250 | | | | | 255 | | |
| cag | cag | caa | cct | cag | gct | gca | tct | cct | tca | gta | ccg | gag | ccc | cac | tct | 816 |
| Gln | Gln | Gln | Pro | Gln | Ala | Ala | Ser | Pro | Ser | Val | Pro | Glu | Pro | His | Ser | |
| | | | | 260 | | | | | 265 | | | | | 270 | | |
| ttg | act | cca | gtg | gct | cag | gca | gat | ccc | ctt | gtg | aga | aga | cag | cga | gta | 864 |
| Leu | Thr | Pro | Val | Ala | Gln | Ala | Asp | Pro | Leu | Val | Arg | Arg | Gln | Arg | Val | |
| | | | 275 | | | | | 280 | | | | | 285 | | | |

```
cag gac ctt atg gcg caa atg cag ggg ccc tat aat ttc ata cag gat      912
Gln Asp Leu Met Ala Gln Met Gln Gly Pro Tyr Asn Phe Ile Gln Asp
    290                 295                 300 tca atg ctg gat ttt gaa aac cag aca ctt gat cct gcc att gta tct      960
Ser Met Leu Asp Phe Glu Asn Gln Thr Leu Asp Pro Ala Ile Val Ser
305                 310                 315                 320 gca cag cct atg aat cca gca cag aat atg gac atg ccc cag ctg gtt     1008
Ala Gln Pro Met Asn Pro Ala Gln Asn Met Asp Met Pro Gln Leu Val
                325                 330                 335 tgc cct cca gtt cat gct gaa tct aga ctt gct caa cct aat caa gtt     1056
Cys Pro Pro Val His Ala Glu Ser Arg Leu Ala Gln Pro Asn Gln Val
            340                 345                 350 cct gta caa cca gaa gct aca cag gtt cct ttg gtt tca tcc aca agt     1104
Pro Val Gln Pro Glu Ala Thr Gln Val Pro Leu Val Ser Ser Thr Ser
        355                 360                 365 gag ggg tat aca gca tct cag ccc ttg tac cag cct tct cat gct aca     1152
Glu Gly Tyr Thr Ala Ser Gln Pro Leu Tyr Gln Pro Ser His Ala Thr
370                 375                 380 gag caa cga ccg caa aag gaa ccg act gac cag atc cag gca aca atc     1200
Glu Gln Arg Pro Gln Lys Glu Pro Thr Asp Gln Ile Gln Ala Thr Ile
385                 390                 395                 400 tct tta aat aca gac cag act aca gca tca tca tcc ctt cct gct gct     1248
Ser Leu Asn Thr Asp Gln Thr Thr Ala Ser Ser Ser Leu Pro Ala Ala
                405                 410                 415 tct cag cct cag gtg ttc cag gct ggg aca agc aaa cct tta cac agc     1296
Ser Gln Pro Gln Val Phe Gln Ala Gly Thr Ser Lys Pro Leu His Ser
            420                 425                 430 agt ggg atc aat gta aat gca gcg cca ttc cag tcc atg caa acg gtg     1344
Ser Gly Ile Asn Val Asn Ala Ala Pro Phe Gln Ser Met Gln Thr Val
        435                 440                 445 ttc aac atg aat gcc ccg gtt cct cct gtt aat gaa cca gaa act tta     1392
Phe Asn Met Asn Ala Pro Val Pro Pro Val Asn Glu Pro Glu Thr Leu
450                 455                 460 aaa cag caa aat cag tac cag gcc agc tat aac cag agc ttt tcc agt     1440
Lys Gln Gln Asn Gln Tyr Gln Ala Ser Tyr Asn Gln Ser Phe Ser Ser
465                 470                 475                 480 ccg cct cac caa gta gag cag aca gag ctt ccg caa gag cag ctt cag     1488
Pro Pro His Gln Val Glu Gln Thr Glu Leu Pro Gln Glu Gln Leu Gln
                485                 490                 495 acg gtg gtt ggt act tac cat gct tcc caa gac cag ccc cat caa gtg     1536
Thr Val Val Gly Thr Tyr His Ala Ser Gln Asp Gln Pro His Gln Val
            500                 505                 510 acc ggt aac cac cag cag cct ccc cag cag aac act ggg ttt cca cgt     1584
Thr Gly Asn His Gln Gln Pro Pro Gln Gln Asn Thr Gly Phe Pro Arg
        515                 520                 525 agc agt cag ccc tat tac aac agt cgt ggt gtg tct cgt gga ggc tcc     1632
Ser Ser Gln Pro Tyr Tyr Asn Ser Arg Gly Val Ser Arg Gly Gly Ser
530                 535                 540 cgt ggt gct aga ggc ttg atg aat gga tac agg ggc cct gcc aat gga     1680
Arg Gly Ala Arg Gly Leu Met Asn Gly Tyr Arg Gly Pro Ala Asn Gly
545                 550                 555                 560 ttc aga gga gga tat gat ggt tac cgc cct tcg ttc tct aac act cca     1728
Phe Arg Gly Gly Tyr Asp Gly Tyr Arg Pro Ser Phe Ser Asn Thr Pro
                565                 570                 575 aac agc ggt tac aca cag tct cag ttc agt gct ccc cgg gac tac tct     1776
Asn Ser Gly Tyr Thr Gln Ser Gln Phe Ser Ala Pro Arg Asp Tyr Ser
            580                 585                 590 ggc tat cag cgg gat gga tat cag cag aat ttc aag cga ggc tct ggg     1824
Gly Tyr Gln Arg Asp Gly Tyr Gln Gln Asn Phe Lys Arg Gly Ser Gly
        595                 600                 605
```

-continued

```
cag agt gga ccc cgg gga gcc cca cga ggt cgt gga ggg ccc cca aga    1872
Gln Ser Gly Pro Arg Gly Ala Pro Arg Gly Arg Gly Gly Pro Pro Arg
    610             615                 620 ccc aac aga ggg atg ccg caa atg aac act cag caa gtg aat taa        1917
Pro Asn Arg Gly Met Pro Gln Met Asn Thr Gln Gln Val Asn
625                 630                 635 tctgattcac aggattatct ttaatcgcca aaacacactg gccagtgtac cataatatgt  1977
taccagaaga gttattatct atttgttctc cctttcagga aacttattgt aaagggactg  2037
ttttcatccc ataaagacag gactacagtt gtcagcttta tattacctgg atatggaagg  2097
aaactatttt tactctgcat gttctgtcct aagcgtcatc ttgagccttg cacatgatac  2157
tcagattcct ttcccttgct taggagtaaa acataatata ctttatgggg tgataatatc  2217
tccatagtta tttgaagtgg cttggaaaaa gcaagattga cttttgacat tggataaaat  2277
ctacaaatca gccctagagt ttcatggtca ttcacaaaac taaatatttt cccttgaaag  2337
gaagatggaa ggactggagt gtggtttggc agaacaactg catttcacag cttttcctat  2397
taaattggag cactgaatgt taaatgcata ccaaattatg catgggccct aatcacaca   2457
tacatggcta ccagctttga cacagcacta ttcatcctct ggccaaacga ctgtggttaa  2517
aaacacgtgt aaattgcttt ttaacagctg atactgtaaa agacaaagct aaaatgcaaa  2577
attaggcttt cattggcact tttcgaaaaa tatgcaacaa atttgggatg taatctggat  2637
ggccacttct gtacttaatg tgaagtattt agatacccttt ttgaacactt aacagtttct  2697
tcgacaatga cttttgtaag gattggtagt atatatcatt ccttatgaca tacattgtct  2757
gttgctaatc cttggatctt gctgtattgt cacctaaatt ggtacaggta ctgatgaaaa  2817
tctctcatgg ataaacctaa cactcttcgt cacatgtttt tcctgcagcc tgaaggtttt  2877
taaaaggaaa agatatcaaa tgcctgctgc taccacccctt ttaaattgct atcttttgaa  2937
aagcaccagt atgtgttttt agattgattt ccctattta gggaaatgac agtcagtagt   2997
ttcagttctg atggtataag caaagcaaat aaaacgtgtt tataaaagtt gtatcttgaa  3057
acactggtgt tcaacagcta gcagcttctg tggttcaccc cctgccttgt tagtgttacc  3117
catttatggt tatctccagc agcaatttct cta                               3150
```

<210> SEQ ID NO 18
<211> LENGTH: 638
<212> TYPE: PRT
<213> ORGANISM: Equus caballus

<400> SEQUENCE: 18

```
Met Glu Gly Lys Leu Asp Asp Tyr Gln Glu Arg Met Asn Lys Gly Glu
1               5                   10                  15

Arg Leu Asn Gln Asp Gln Leu Asp Ala Val Ser Lys Tyr Gln Glu Val
                20                  25                  30

Thr Asn Asn Leu Glu Phe Ala Lys Glu Leu Gln Arg Ser Phe Met Ala
            35                  40                  45

Leu Ser Gln Asp Ile Gln Lys Thr Ile Lys Lys Thr Ala Arg Arg Glu
        50                  55                  60

Gln Leu Met Arg Glu Glu Ala Glu Gln Lys Arg Leu Lys Thr Val Leu
65                  70                  75                  80

Glu Leu Gln Tyr Val Leu Asp Lys Leu Gly Asp Glu Val Arg Thr
                85                  90                  95

Asp Leu Lys Gln Gly Leu Asn Gly Val Pro Ile Leu Ser Glu Glu Glu
            100                 105                 110
```

-continued

```
Leu Ser Leu Leu Asp Glu Phe Tyr Lys Leu Ala Asp Pro Val Arg Asp
        115                 120                 125

Met Ser Leu Arg Leu Asn Glu Gln Tyr Glu His Ala Ser Ile His Leu
    130                 135                 140

Trp Asp Leu Leu Glu Gly Lys Glu Lys Ser Val Cys Gly Thr Thr Tyr
145                 150                 155                 160

Lys Ala Leu Arg Glu Ile Val Glu Arg Val Phe Gln Ser Asn Tyr Phe
                165                 170                 175

Asp Ser Thr His Asn His Gln Asn Gly Leu Cys Glu Glu Glu Glu Ala
            180                 185                 190

Thr Ser Ala Pro Thr Ala Glu Asp Gln Gly Ala Glu Ala Glu Pro Glu
                195                 200                 205

Pro Ala Glu Glu Tyr Thr Glu Gln Ser Glu Val Glu Ser Thr Glu Tyr
210                 215                 220

Val Asn Arg Gln Phe Met Ala Glu Ala Gln Phe Ser Gly Glu Lys Glu
225                 230                 235                 240

Gln Val Asp Glu Trp Thr Val Glu Thr Val Glu Val Asn Ser Leu
                245                 250                 255

Gln Gln Gln Pro Gln Ala Ala Ser Pro Ser Val Pro Glu Pro His Ser
            260                 265                 270

Leu Thr Pro Val Ala Gln Ala Asp Pro Leu Val Arg Arg Gln Arg Val
            275                 280                 285

Gln Asp Leu Met Ala Gln Met Gln Gly Pro Tyr Asn Phe Ile Gln Asp
    290                 295                 300

Ser Met Leu Asp Phe Glu Asn Gln Thr Leu Asp Pro Ala Ile Val Ser
305                 310                 315                 320

Ala Gln Pro Met Asn Pro Ala Gln Asn Met Asp Met Pro Gln Leu Val
                325                 330                 335

Cys Pro Pro Val His Ala Glu Ser Arg Leu Ala Gln Pro Asn Gln Val
            340                 345                 350

Pro Val Gln Pro Glu Ala Thr Gln Val Pro Leu Val Ser Ser Thr Ser
        355                 360                 365

Glu Gly Tyr Thr Ala Ser Gln Pro Leu Tyr Gln Pro Ser His Ala Thr
    370                 375                 380

Glu Gln Arg Pro Gln Lys Glu Pro Thr Asp Gln Ile Gln Ala Thr Ile
385                 390                 395                 400

Ser Leu Asn Thr Asp Gln Thr Thr Ala Ser Ser Leu Pro Ala Ala
                405                 410                 415

Ser Gln Pro Gln Val Phe Gln Ala Gly Thr Ser Lys Pro Leu His Ser
            420                 425                 430

Ser Gly Ile Asn Val Asn Ala Ala Pro Phe Gln Ser Met Gln Thr Val
        435                 440                 445

Phe Asn Met Asn Ala Pro Val Pro Val Asn Glu Pro Glu Thr Leu
450                 455                 460

Lys Gln Gln Asn Gln Tyr Gln Ala Ser Tyr Asn Gln Ser Phe Ser Ser
465                 470                 475                 480

Pro Pro His Gln Val Glu Gln Thr Glu Leu Pro Gln Glu Gln Leu Gln
                485                 490                 495

Thr Val Val Gly Thr Tyr His Ala Ser Gln Asp Gln Pro His Gln Val
            500                 505                 510

Thr Gly Asn His Gln Gln Pro Gln Gln Asn Thr Gly Phe Pro Arg
        515                 520                 525

Ser Ser Gln Pro Tyr Tyr Asn Ser Arg Gly Val Ser Arg Gly Gly Ser
    530                 535                 540
```

```
Arg Gly Ala Arg Gly Leu Met Asn Gly Tyr Arg Gly Pro Ala Asn Gly
545                 550                 555                 560

Phe Arg Gly Gly Tyr Asp Gly Tyr Arg Pro Ser Phe Ser Asn Thr Pro
                565                 570                 575

Asn Ser Gly Tyr Thr Gln Ser Gln Phe Ser Ala Pro Arg Asp Tyr Ser
            580                 585                 590

Gly Tyr Gln Arg Asp Gly Tyr Gln Gln Asn Phe Lys Arg Gly Ser Gly
        595                 600                 605

Gln Ser Gly Pro Arg Gly Ala Pro Arg Gly Arg Gly Pro Pro Arg
    610                 615                 620

Pro Asn Arg Gly Met Pro Gln Met Asn Thr Gln Gln Val Asn
625                 630                 635

<210> SEQ ID NO 19
<211> LENGTH: 6181
<212> TYPE: DNA
<213> ORGANISM: Mus musculus
<220> FEATURE:
<221> NAME/KEY: CDS
<222> LOCATION: (179)..(2302)
<223> OTHER INFORMATION:

<400> SEQUENCE: 19
gctggctggc taagtccctc ccgcgccggc tcttgtccca ctaggagcag ctcagagccg    60
cggggacagg gcgaagcggc ctgcgcccac ggagcgcacg tctctgttct caacgcagca   120
ccacccttgc cccctcggc tgcccactcc agacgtccag cggctccgcg cgcgcacg      178 atg ccc tcg gcc acc agc cac agc gga agc ggc agc aaa tcg tcg gga    226
Met Pro Ser Ala Thr Ser His Ser Gly Ser Gly Ser Lys Ser Ser Gly
1               5                   10                  15 ccg ccg ccg ccg tcc ggt tcc tcc ggg agt gag gcg gcg gcc ggg gca    274
Pro Pro Pro Pro Ser Gly Ser Ser Gly Ser Glu Ala Ala Ala Gly Ala
            20                  25                  30 gct gcg ccg gct tct cag cat ccg gca acc ggc acc ggc gcc gtc cag    322
Ala Ala Pro Ala Ser Gln His Pro Ala Thr Gly Thr Gly Ala Val Gln
        35                  40                  45 acc gag gcc atg aag cag att ctc ggc gta atc gac aag aaa ctt cgg    370
Thr Glu Ala Met Lys Gln Ile Leu Gly Val Ile Asp Lys Lys Leu Arg
50                  55                  60 aac ctg gag aag aaa aag ggt aaa ctt gat gat tac cag gaa cga atg    418
Asn Leu Glu Lys Lys Lys Gly Lys Leu Asp Asp Tyr Gln Glu Arg Met
65                  70                  75                  80 aat aaa ggg gaa agg ctc aat caa gac cag ctg gat gcc gta tct aag    466
Asn Lys Gly Glu Arg Leu Asn Gln Asp Gln Leu Asp Ala Val Ser Lys
                85                  90                  95 tac cag gaa gtc aca aat aat ttg gag ttt gca aag gaa tta cag agg    514
Tyr Gln Glu Val Thr Asn Asn Leu Glu Phe Ala Lys Glu Leu Gln Arg
            100                 105                 110 agt ttc atg gca tta agt caa gat att cag aaa aca ata aag aag aca    562
Ser Phe Met Ala Leu Ser Gln Asp Ile Gln Lys Thr Ile Lys Lys Thr
        115                 120                 125 gca cgt cgg gaa cag ctt atg aga gaa gaa gca gaa cag aag cgc tta    610
Ala Arg Arg Glu Gln Leu Met Arg Glu Glu Ala Glu Gln Lys Arg Leu
        130                 135                 140 aaa act gta ctt gag tta cag tat gta ttg gat aag ctg gga gat gat    658
Lys Thr Val Leu Glu Leu Gln Tyr Val Leu Asp Lys Leu Gly Asp Asp
145                 150                 155                 160 gat gtg aga aca gat ctg aaa caa ggt ttg agt gga gtg cca ata ttg    706
Asp Val Arg Thr Asp Leu Lys Gln Gly Leu Ser Gly Val Pro Ile Leu
                165                 170                 175
```

| | | |
|---|---|---|
| tct gag gag gag ttg tca ttg ctg gat gag ttc tac aag ctc gta gat<br>Ser Glu Glu Glu Leu Ser Leu Leu Asp Glu Phe Tyr Lys Leu Val Asp<br>          180                 185                 190 | 754 | |
| cct gag cgt gac atg agt tta agg tta aat gag cag tat gaa cat gcc<br>Pro Glu Arg Asp Met Ser Leu Arg Leu Asn Glu Gln Tyr Glu His Ala<br>    195                 200                 205 | 802 | |
| tca att cac ttg tgg gat ttg ctg gaa ggg aaa gaa aag cct gtg tgt<br>Ser Ile His Leu Trp Asp Leu Leu Glu Gly Lys Glu Lys Pro Val Cys<br>210                 215                 220 | 850 | |
| gga aca acc tat aaa gct cta aag gaa att gtt gag cgt gtt ttc cag<br>Gly Thr Thr Tyr Lys Ala Leu Lys Glu Ile Val Glu Arg Val Phe Gln<br>225                 230                 235                 240 | 898 | |
| tca aac tac ttt gat agc act cac aat cat caa aat ggg ttg tgt gag<br>Ser Asn Tyr Phe Asp Ser Thr His Asn His Gln Asn Gly Leu Cys Glu<br>            245                 250                 255 | 946 | |
| gag gaa gag gcg gct tca gcg ccc aca gtg gag gac cag gta gct gaa<br>Glu Glu Glu Ala Ala Ser Ala Pro Thr Val Glu Asp Gln Val Ala Glu<br>        260                 265                 270 | 994 | |
| gct gaa cct gag cca gcg gaa gaa tac aca gag caa agt gag gtt gaa<br>Ala Glu Pro Glu Pro Ala Glu Glu Tyr Thr Glu Gln Ser Glu Val Glu<br>    275                 280                 285 | 1042 | |
| tca aca gag tat gtc aat agg cag ttc atg gca gaa aca cag ttc agc<br>Ser Thr Glu Tyr Val Asn Arg Gln Phe Met Ala Glu Thr Gln Phe Ser<br>290                 295                 300 | 1090 | |
| agt ggt gag aag gag caa gtg gat gag tgg aca gtt gaa aca gtt gag<br>Ser Gly Glu Lys Glu Gln Val Asp Glu Trp Thr Val Glu Thr Val Glu<br>305                 310                 315                 320 | 1138 | |
| gtt gta aac tca ctc cag cag caa cct cag gct gcg tcc cct tca gtc<br>Val Val Asn Ser Leu Gln Gln Gln Pro Gln Ala Ala Ser Pro Ser Val<br>            325                 330                 335 | 1186 | |
| cca gag ccc cac tct ttg act cca gtg gct cag tca gat cca ctt gtg<br>Pro Glu Pro His Ser Leu Thr Pro Val Ala Gln Ser Asp Pro Leu Val<br>        340                 345                 350 | 1234 | |
| aga agg cag cgt gta caa gat ctt atg gca caa atg caa ggg ccc tat<br>Arg Arg Gln Arg Val Gln Asp Leu Met Ala Gln Met Gln Gly Pro Tyr<br>    355                 360                 365 | 1282 | |
| aat ttc ata cag gat tca atg ttg gat ttt gaa aat cag acg ctt gat<br>Asn Phe Ile Gln Asp Ser Met Leu Asp Phe Glu Asn Gln Thr Leu Asp<br>370                 375                 380 | 1330 | |
| cct gcc att gta tcc gca cag cct atg aac cct acc cag aac atg gat<br>Pro Ala Ile Val Ser Ala Gln Pro Met Asn Pro Thr Gln Asn Met Asp<br>385                 390                 395                 400 | 1378 | |
| atg cct cag ctg gtt tgc cct cag gtt cat tct gaa tct aga ctt gcc<br>Met Pro Gln Leu Val Cys Pro Gln Val His Ser Glu Ser Arg Leu Ala<br>            405                 410                 415 | 1426 | |
| caa tct aat caa gtt cct gta caa cca gaa gcc aca cag gtt cct ttg<br>Gln Ser Asn Gln Val Pro Val Gln Pro Glu Ala Thr Gln Val Pro Leu<br>        420                 425                 430 | 1474 | |
| gtt tca tcc aca agt gag ggg tat aca gca tct cag ccc ttg tac cag<br>Val Ser Ser Thr Ser Glu Gly Tyr Thr Ala Ser Gln Pro Leu Tyr Gln<br>    435                 440                 445 | 1522 | |
| cca tct cat gct acg gag cag cgg ccg cag aaa gag cca atg gat cag<br>Pro Ser His Ala Thr Glu Gln Arg Pro Gln Lys Glu Pro Met Asp Gln<br>450                 455                 460 | 1570 | |
| att cag gca aca ata tct ttg aat aca gac cag act aca gca tcc tca<br>Ile Gln Ala Thr Ile Ser Leu Asn Thr Asp Gln Thr Thr Ala Ser Ser<br>465                 470                 475                 480 | 1618 | |
| tcc ctt cct gct gct tct cag cct caa gtg ttc cag gct ggg aca agt<br>Ser Leu Pro Ala Ala Ser Gln Pro Gln Val Phe Gln Ala Gly Thr Ser<br>            485                 490                 495 | 1666 | |

```
aaa cct ttg cac agc agt gga atc aat gta aat gca gct cca ttc cag     1714
Lys Pro Leu His Ser Ser Gly Ile Asn Val Asn Ala Ala Pro Phe Gln
        500                 505                 510 tcc atg caa acg gtg ttc aat atg aat gct cca gtc cct cct gct aat     1762
Ser Met Gln Thr Val Phe Asn Met Asn Ala Pro Val Pro Pro Ala Asn
        515                 520                 525 gaa cca gaa acg tta aaa caa cag agt cag tac cag gcc act tat aac     1810
Glu Pro Glu Thr Leu Lys Gln Gln Ser Gln Tyr Gln Ala Thr Tyr Asn
        530                 535                 540 cag agt ttt tcc agt cag cct cac caa gtg gaa caa aca gag ctt caa     1858
Gln Ser Phe Ser Ser Gln Pro His Gln Val Glu Gln Thr Glu Leu Gln
545                 550                 555                 560 caa gac caa ctg caa acg gtg gtt ggc act tac cat gga tcc cag gac     1906
Gln Asp Gln Leu Gln Thr Val Val Gly Thr Tyr His Gly Ser Gln Asp
                565                 570                 575 cag cct cat caa gtg cct ggt aac cac cag caa ccc cca cag cag aac     1954
Gln Pro His Gln Val Pro Gly Asn His Gln Gln Pro Pro Gln Gln Asn
            580                 585                 590 act ggc ttt cca cgt agc agt cag cct tat tac aac agt cgt ggg gta     2002
Thr Gly Phe Pro Arg Ser Ser Gln Pro Tyr Tyr Asn Ser Arg Gly Val
            595                 600                 605 tct cga gga ggg tct cgt ggt gcc aga ggc ttg atg aat gga tac agg     2050
Ser Arg Gly Gly Ser Arg Gly Ala Arg Gly Leu Met Asn Gly Tyr Arg
        610                 615                 620 ggc cct gcc aat gga ttt aga gga gga tat gat ggt tac cgc cct tca     2098
Gly Pro Ala Asn Gly Phe Arg Gly Gly Tyr Asp Gly Tyr Arg Pro Ser
625                 630                 635                 640 ttc tcg aac act cca aac agt ggt tat tca cag tct cag ttc act gct     2146
Phe Ser Asn Thr Pro Asn Ser Gly Tyr Ser Gln Ser Gln Phe Thr Ala
                645                 650                 655 ccc cgg gac tac tct ggt tac cag cgg gat gga tat cag cag aat ttc     2194
Pro Arg Asp Tyr Ser Gly Tyr Gln Arg Asp Gly Tyr Gln Gln Asn Phe
            660                 665                 670 aag cga ggc tct ggg cag agt gga cca cgg gga gcc cca cga ggt cgt     2242
Lys Arg Gly Ser Gly Gln Ser Gly Pro Arg Gly Ala Pro Arg Gly Arg
            675                 680                 685 gga ggg ccc cca aga ccc aac aga ggg atg ccg caa atg aac act cag     2290
Gly Gly Pro Pro Arg Pro Asn Arg Gly Met Pro Gln Met Asn Thr Gln
        690                 695                 700 caa gtg aat taa tgtgatacac aggattatgt ttaatcgcca aaaacacact         2342
Gln Val Asn
705 ggccagtgta ccataatatg ttaccagaag agtattatc tatttgttct ccctttcagg    2402 aaacttattg taagggact gttttcatcc cataaagaca ggactgcaat tgtcagcttt    2462 acattacctg gatatggaag gaaactattt ttattctgca tgttctgtcc taagcgtcat   2522 cttgagcctt gcacacaata caatactcag attcctcacc cttgcttagg agtaaaacat   2582 tatatactta tggggtgata atatctccat agttagttga agtggcttgg aaaaaaaatg   2642 caagattgaa tttttgacct tggataaaat ctacaatcag ccctagaact attcagtggt   2702 aattgacaaa gttaaagcat tttctttgaa aggaagatgg aaggagtgga gtgtggttta   2762 gcaaaactgc atttcatagc tttcccatta aattggagca ccgacagatt aaaagcatac   2822 caaattatgc atgggtcctt actcacacaa gtgaggctgg ctaccagcct tgacatagca   2882 ctcactagtc ttctggccaa acgactgtga ttaaaacaca gtaaattgc tctttagtag    2942 tggatactgt gtaagacaaa gccaaattgc aaatcaggct ttgattggct cttctggaaa   3002 atatgcatca aatatggggg ataatctgga tgggctgctg ctgtgctcaa tgtgaactat   3062
```

```
ttagataccct ttggaacact taacagtttc tctgaacaat gacttacatg gggattggtc    3122
ctgtttgtca ttcctcacca taattgcatt gtcatcacta atccttggat cttgctgtat    3182
tgttactcaa attggtaata ggtactgatg gaaatcgcta atggatggat aatcataaca    3242
cttttggtca catgttttct cctgcagcct gaaagttctt aaagaaaaag atatcaaatg    3302
cctgctgcta ccacccttt aaattgctat ctttagaaaa gcaccggtat gtgttttaga    3362
ttcatttccc tgttttaggg aaatgacagg cagtagtttc agttctgatg gcaaaacaaa    3422
taaaaacatg tttctaaaag ttgtatcttg aaacactggt gttcaacagc tagcagctaa    3482
agtaattcaa cccatgcatt gctagtgtca cagcctttgg ttatgtctag tagctgtttc    3542
tgaagtattt tcatttatct tttgtcaaat ttaaccctgt ttgaattctc tcctttcctc    3602
aaggagacac ttatgttcaa agtgttgatt ctttgcctta ggtgcataga gagtagacag    3662
tttggagatg gaaaggttag cagtgactta gccatatgtt ctgtgttgga atttgtgcta    3722
gcagtttgag cactagctct gcgtgcctat gaactgaatg ctgcttgtcc cattccattt    3782
tatgtcatgg agaaataatt ccacttggta acacaaaggc taagttaatg ttattttctg    3842
tacagaaatt aaatttttact tttagccttt tgtaaacttt ttttttttt ttccaagccg    3902 gtatcagcta ctcaaaacaa ttctcagata ttcatcatta gacaactgga gttttgctg    3962 gttttgtagc ctactaaaac tgctgaggct gttgaacatt ccacattcaa aagttttgta    4022
gggtggtgga taatggggaa gcttcaatgt ttattttaaa ataaataaaa taagttcttg    4082
acttttctca tgtgtggtta tggtacatca tattggaagg gttatctgtt tacttttgcc    4142
aagactattt tgccagcacc tacacttgtg tgctttaaaa gacaactacc tgggatgtac    4202
cacaaccata tgttaattgt attttattgg gatggataaa atgtttgtgg tttattggat    4262
aatccctaga tggtgtgtta cgtgtgtaga atataatttt atgatagtaa gaaagcaaaa    4322
ttgaagaaaa taagtttagt attgaatttg agttctgaag tgaattcagg gaatgtctca    4382
cgtttcgggc ttctacccaa agtgtagggc agaaggtgta aaagttgttt gtagtttgac    4442 ttgtttatt tttaagttgc ttattccttt caacagcaac atatcattag ctgtcattct    4502
accattgcag ttcagtgag ttttaacgtc tgcattcaag actgttttaa aagcaacctc    4562
actggacaga gaactgctaa agtcttttcc ttaagatctg agtctttgtt actcagtatc    4622
ttctataata tgcaaatgct tgtctagagg cagaagacct tttgtttggt caagtgtgta    4682
ttttaccaga gtacagggaa ctgatggtcc tacatgtctc ttagtgtagt aagactataa    4742
aatcttttgt acatgcacaa ttcacagtat gtttagatac cacgtgtata atgccccccc    4802
ctcccccagg tagcatgcca ttgatgactt tttgcttagg gccatttat taccagggcc    4862 ttaatattcc taaaagatg attttttttc atcctttctc ctcttttgat cattgtatct    4922
tgatattaaa aacatgacct tccaatgatt gtagtaaatt aacttctata gttcttttgt    4982
ctctatatgt attcatatat atgctattgt atagagactt caaggagaca tggagatgca    5042
tgcttattct caggttcatt cactaaggtg cttggcagac aaccagttc taagtgcaga    5102 atgtagttaa gcagcttcat atatgtgcca ggcaatttgt tttgttaaat tttcatctac    5162
ttaaggaaat agggtattgt agcttaggct gatcataccc ttcatttcaa ccttaagctc    5222
tcaacctgca tccatccgac ttgagctatt aagtacttta gttttatcga gtataagtta    5282
acagaaaaag taaattaagc tttgccttta ctattttgaa tttatataca ttctggaaaa    5342
acttagaaac tgttgtatat ttcattagat taaattatat gaaaatgtga ttgtttatag    5402
caaagcctgt gagttgcata caccctaagg aaaactcctt aagtgctcct tgaagagaga    5462
```

```
agaaacaatt ctgggtctgg tcttttaag aacaaagcta gactactgta tgttagcact    5522
gtacattaat agtctgttgt gaagcttgag cagtttcctg catagccttg atccttcacc    5582
gttggcattg aaaatagcag tatccctgat gtacttaaaa cttaaagtca ggttttggta    5642
tatttatttg taagtcttaa tttcctctaa atactatatc tctttagcga gacaacctga    5702
aatttattag cacatttggg tatctcttgc ttggcattat ggccagtgtt aactattcag    5762
tggtgaaaaa attacccctc aagacactgg agtgacccca gatgtgtgta gtaagtggca    5822
tggttcaact gtgtggttaa tgataaatat atgacttagt cggtatgatc tggaaagact    5882
tgattgaaag ataattcagc tgacataagg atgagtgagg agtggcaaac tggataaaag    5942
agtcaagaga cctgtattcc agtgactcct gttttgttta agcattagca agatctgtct    6002
ggggaaactg gatagggcag ttttcttcca tgtttagttt ttgtctcaac atttggaagc    6062
tattgaaggt tttaaaatgg tgtgtattgt ttttttttgg ggggggggtg gccagaatag    6122
tgggtcatct aataaaactg ccatttaaaa gatcaaaaaa aaaaaaaaa aaaaaaaa      6181
```

<210> SEQ ID NO 20
<211> LENGTH: 707
<212> TYPE: PRT
<213> ORGANISM: Mus musculus

<400> SEQUENCE: 20

```
Met Pro Ser Ala Thr Ser His Ser Gly Ser Gly Ser Lys Ser Gly
1               5                   10                  15

Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
            35                  40                  45

Thr Glu Ala Met Lys Gln Ile Leu Gly Val Ile Asp Lys Lys Leu Arg
50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
            85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Gln Lys Arg Leu
        130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His His Gln Asn Gly Leu Cys Glu
            245                 250                 255
```

-continued

```
Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
```

```
                    675                 680                 685
Gly Gly Pro Pro Arg Pro Asn Arg Gly Met Pro Gln Met Asn Thr Gln
    690                 695                 700

Gln Val Asn
705

<210> SEQ ID NO 21
<211> LENGTH: 6141
<212> TYPE: DNA
<213> ORGANISM: Mus musculus
<220> FEATURE:
<221> NAME/KEY: CDS
<222> LOCATION: (139)..(2262)
<223> OTHER INFORMATION:

<400> SEQUENCE: 21
cccaccgcgc gcgcgcgtag ccgcctgccc gcccgcccgc tgcgcgtttt gtcccgcgtc      60 tctcccgtc cgtctcctga cttgctggtc ttgtccttcc ctcccgcttt tttcctctcc      120
tctcttctcg gtctaaag atg ccc tcg gcc acc agc cac agc gga agc ggc      171
                    Met Pro Ser Ala Thr Ser His Ser Gly Ser Gly
                     1               5                  10 agc aaa tcg tcg gga ccg ccg ccg ccg tcc ggt tcc tcc ggg agt gag      219
Ser Lys Ser Ser Gly Pro Pro Pro Pro Ser Gly Ser Ser Gly Ser Glu
            15                  20                  25 gcg gcg gcc ggg gca gct gcg ccg gct tct cag cat ccg gca acc ggc      267
Ala Ala Ala Gly Ala Ala Ala Pro Ala Ser Gln His Pro Ala Thr Gly
        30                  35                  40 acc ggc gcc gtc cag acc gag gcc atg aag cag att ctc ggc gta atc      315
Thr Gly Ala Val Gln Thr Glu Ala Met Lys Gln Ile Leu Gly Val Ile
    45                  50                  55 gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60                  65                  70                  75 tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90 gat gcc gta tct aag tac cag gaa gtc aca aat aat ttg gag ttt gca      459
Asp Ala Val Ser Lys Tyr Gln Glu Val Thr Asn Asn Leu Glu Phe Ala
            95                  100                 105 aag gaa tta cag agg agt ttc atg gca tta agt caa gat att cag aaa      507
Lys Glu Leu Gln Arg Ser Phe Met Ala Leu Ser Gln Asp Ile Gln Lys
        110                 115                 120 aca ata aag aag aca gca cgt cgg gaa cag ctt atg aga gaa gaa gca      555
Thr Ile Lys Lys Thr Ala Arg Arg Glu Gln Leu Met Arg Glu Glu Ala
    125                 130                 135 gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155 aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170 gga gtg cca ata ttg tct gag gag gag ttg tca ttg ctg gat gag ttc      699
Gly Val Pro Ile Leu Ser Glu Glu Glu Leu Ser Leu Leu Asp Glu Phe
            175                 180                 185 tac aag ctc gta gat cct gag cgt gac atg agt tta agg tta aat gag      747
Tyr Lys Leu Val Asp Pro Glu Arg Asp Met Ser Leu Arg Leu Asn Glu
        190                 195                 200 cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215
```

```
gaa aag cct gtg tgt gga aca acc tat aaa gct cta aag gaa att gtt    843
Glu Lys Pro Val Cys Gly Thr Thr Tyr Lys Ala Leu Lys Glu Ile Val
220             225                 230                 235 gag cgt gtt ttc cag tca aac tac ttt gat agc act cac aat cat caa    891
Glu Arg Val Phe Gln Ser Asn Tyr Phe Asp Ser Thr His Asn His Gln
                240                 245                 250 aat ggg ttg tgt gag gag gaa gag gcg gct tca gcg ccc aca gtg gag    939
Asn Gly Leu Cys Glu Glu Glu Glu Ala Ala Ser Ala Pro Thr Val Glu
                    255                 260                 265 gac cag gta gct gaa gct gaa cct gag cca gcg gaa gaa tac aca gag    987
Asp Gln Val Ala Glu Ala Glu Pro Glu Pro Ala Glu Glu Tyr Thr Glu
                270                 275                 280 caa agt gag gtt gaa tca aca gag tat gtc aat agg cag ttc atg gca   1035
Gln Ser Glu Val Glu Ser Thr Glu Tyr Val Asn Arg Gln Phe Met Ala
285                 290                 295 gaa aca cag ttc agc agt ggt gag aag gag caa gtg gat gag tgg aca   1083
Glu Thr Gln Phe Ser Ser Gly Glu Lys Glu Gln Val Asp Glu Trp Thr
300                 305                 310                 315 gtt gaa aca gtt gag gtt gta aac tca ctc cag cag caa cct cag gct   1131
Val Glu Thr Val Glu Val Val Asn Ser Leu Gln Gln Gln Pro Gln Ala
                320                 325                 330 gcg tcc cct tca gtc cca gag ccc cac tct ttg act cca gtg gct cag   1179
Ala Ser Pro Ser Val Pro Glu Pro His Ser Leu Thr Pro Val Ala Gln
                335                 340                 345 tca gat cca ctt gtg aga agg cag cgt gta caa gat ctt atg gca caa   1227
Ser Asp Pro Leu Val Arg Arg Gln Arg Val Gln Asp Leu Met Ala Gln
                350                 355                 360 atg caa ggg ccc tat aat ttc ata cag gat tca atg ttg gat ttt gaa   1275
Met Gln Gly Pro Tyr Asn Phe Ile Gln Asp Ser Met Leu Asp Phe Glu
365                 370                 375 aat cag acg ctt gat cct gcc att gta tcc gca cag cct atg aac cct   1323
Asn Gln Thr Leu Asp Pro Ala Ile Val Ser Ala Gln Pro Met Asn Pro
380                 385                 390                 395 acc cag aac atg gat atg cct cag ctg gtt tgc cct cag gtt cat tct   1371
Thr Gln Asn Met Asp Met Pro Gln Leu Val Cys Pro Gln Val His Ser
                400                 405                 410 gaa tct aga ctt gcc caa tct aat caa gtt cct gta caa cca gaa gcc   1419
Glu Ser Arg Leu Ala Gln Ser Asn Gln Val Pro Val Gln Pro Glu Ala
                415                 420                 425 aca cag gtt cct ttg gtt tca tcc aca agt gag ggg tat aca gca tct   1467
Thr Gln Val Pro Leu Val Ser Ser Thr Ser Glu Gly Tyr Thr Ala Ser
                430                 435                 440 cag ccc ttg tac cag cca tct cat gct acg gag cag cgg ccg cag aaa   1515
Gln Pro Leu Tyr Gln Pro Ser His Ala Thr Glu Gln Arg Pro Gln Lys
445                 450                 455 gag cca atg gat cag att cag gca aca ata tct ttg aat aca gac cag   1563
Glu Pro Met Asp Gln Ile Gln Ala Thr Ile Ser Leu Asn Thr Asp Gln
460                 465                 470                 475 act aca gca tcc tca tcc ctt cct gct gct tct cag cct caa gtg ttc   1611
Thr Thr Ala Ser Ser Ser Leu Pro Ala Ala Ser Gln Pro Gln Val Phe
                480                 485                 490 cag gct ggg aca agt aaa cct ttg cac agc agt gga atc aat gta aat   1659
Gln Ala Gly Thr Ser Lys Pro Leu His Ser Ser Gly Ile Asn Val Asn
                495                 500                 505 gca gct cca ttc cag tcc atg caa acg gtg ttc aat atg aat gct cca   1707
Ala Ala Pro Phe Gln Ser Met Gln Thr Val Phe Asn Met Asn Ala Pro
                510                 515                 520 gtc cct cct gct aat gaa cca gaa acg tta aaa caa cag agt cag tac   1755
Val Pro Pro Ala Asn Glu Pro Glu Thr Leu Lys Gln Gln Ser Gln Tyr
525                 530                 535
```

| | | | | | | | | | | | | | | | |
|---|---|---|---|---|---|---|---|---|---|---|---|---|---|---|---|
| cag | gcc | act | tat | aac | cag | agt | ttt | tcc | agt | cag | cct | cac | caa | gtg | gaa | 1803 |
| Gln | Ala | Thr | Tyr | Asn | Gln | Ser | Phe | Ser | Ser | Gln | Pro | His | Gln | Val | Glu | |
| 540 | | | | 545 | | | | | 550 | | | | | 555 | | |

| | | | | | | | | | | | | | | | |
|---|---|---|---|---|---|---|---|---|---|---|---|---|---|---|---|
| caa | aca | gag | ctt | caa | caa | gac | caa | ctg | caa | acg | gtg | gtt | ggc | act | tac | 1851 |
| Gln | Thr | Glu | Leu | Gln | Gln | Asp | Gln | Leu | Gln | Thr | Val | Val | Gly | Thr | Tyr | |
| | | | | 560 | | | | | 565 | | | | | 570 | | |

| | | | | | | | | | | | | | | | |
|---|---|---|---|---|---|---|---|---|---|---|---|---|---|---|---|
| cat | gga | tcc | cag | gac | cag | cct | cat | caa | gtg | cct | ggt | aac | cac | cag | caa | 1899 |
| His | Gly | Ser | Gln | Asp | Gln | Pro | His | Gln | Val | Pro | Gly | Asn | His | Gln | Gln | |
| | | | 575 | | | | | 580 | | | | | 585 | | | |

| | | | | | | | | | | | | | | | |
|---|---|---|---|---|---|---|---|---|---|---|---|---|---|---|---|
| ccc | cca | cag | cag | aac | act | ggc | ttt | cca | cgt | agc | agt | cag | cct | tat | tac | 1947 |
| Pro | Pro | Gln | Gln | Asn | Thr | Gly | Phe | Pro | Arg | Ser | Ser | Gln | Pro | Tyr | Tyr | |
| | | 590 | | | | | 595 | | | | | 600 | | | | |

| | | | | | | | | | | | | | | | |
|---|---|---|---|---|---|---|---|---|---|---|---|---|---|---|---|
| aac | agt | cgt | ggg | gta | tct | cga | gga | ggg | tct | cgt | ggt | gcc | aga | ggc | ttg | 1995 |
| Asn | Ser | Arg | Gly | Val | Ser | Arg | Gly | Gly | Ser | Arg | Gly | Ala | Arg | Gly | Leu | |
| | 605 | | | | | 610 | | | | | 615 | | | | | |

| | | | | | | | | | | | | | | | |
|---|---|---|---|---|---|---|---|---|---|---|---|---|---|---|---|
| atg | aat | gga | tac | agg | ggc | cct | gcc | aat | gga | ttt | aga | gga | gga | tat | gat | 2043 |
| Met | Asn | Gly | Tyr | Arg | Gly | Pro | Ala | Asn | Gly | Phe | Arg | Gly | Gly | Tyr | Asp | |
| 620 | | | | | 625 | | | | | 630 | | | | | 635 | |

| | | | | | | | | | | | | | | | |
|---|---|---|---|---|---|---|---|---|---|---|---|---|---|---|---|
| ggt | tac | cgc | cct | tca | ttc | tcg | aac | act | cca | aac | agt | ggt | tat | tca | cag | 2091 |
| Gly | Tyr | Arg | Pro | Ser | Phe | Ser | Asn | Thr | Pro | Asn | Ser | Gly | Tyr | Ser | Gln | |
| | | | | 640 | | | | | 645 | | | | | 650 | | |

| | | | | | | | | | | | | | | | |
|---|---|---|---|---|---|---|---|---|---|---|---|---|---|---|---|
| tct | cag | ttc | act | gct | ccc | cgg | gac | tac | tct | ggt | tac | cag | cgg | gat | gga | 2139 |
| Ser | Gln | Phe | Thr | Ala | Pro | Arg | Asp | Tyr | Ser | Gly | Tyr | Gln | Arg | Asp | Gly | |
| | | | 655 | | | | | 660 | | | | | 665 | | | |

| | | | | | | | | | | | | | | | |
|---|---|---|---|---|---|---|---|---|---|---|---|---|---|---|---|
| tat | cag | cag | aat | ttc | aag | cga | ggc | tct | ggg | cag | agt | gga | cca | cgg | gga | 2187 |
| Tyr | Gln | Gln | Asn | Phe | Lys | Arg | Gly | Ser | Gly | Gln | Ser | Gly | Pro | Arg | Gly | |
| | | 670 | | | | | 675 | | | | | 680 | | | | |

| | | | | | | | | | | | | | | | |
|---|---|---|---|---|---|---|---|---|---|---|---|---|---|---|---|
| gcc | cca | cga | ggt | cgt | gga | ggg | ccc | cca | aga | ccc | aac | aga | ggg | atg | ccg | 2235 |
| Ala | Pro | Arg | Gly | Arg | Gly | Gly | Pro | Pro | Arg | Pro | Asn | Arg | Gly | Met | Pro | |
| | 685 | | | | | 690 | | | | | 695 | | | | | |

| | | | | | | | |
|---|---|---|---|---|---|---|---|
| caa | atg | aac | act | cag | caa | gtg | aat | taa tgtgatacac aggattatgt | 2282 |
| Gln | Met | Asn | Thr | Gln | Gln | Val | Asn | |
| 700 | | | | 705 | | | | | ttaatcgcca aaacacact ggccagtgta ccataatatg ttaccagaag agttattatc 2342 tatttgttct ccctttcagg aaacttattg taaagggact gttttcatcc cataaagaca 2402 ggactgcaat tgtcagcttt acattacctg gatatgaag gaaactattt ttattctgca 2462 tgttctgtcc taagcgtcat cttgagcctt gcacacaata caatactcag attcctcacc 2522 cttgcttagg agtaaaacat tatatactta tggggtgata atatctccat agttagttga 2582 agtggcttgg aaaaaaaatg caagattgaa ttttgacct tggataaaat ctacaatcag 2642 ccctagaact attcagtggt aattgacaaa gttaaagcat tttctttgaa aggaagatgg 2702 aaggagtgga gtgtggttta gcaaaactgc atttcatagc tttcccatta aattggagca 2762 ccgacagatt aaaagcatac caaattatgc atgggtcctt actcacacaa gtgaggctgg 2822 ctaccagcct tgacatagca ctcactagtc ttctggccaa acgactgtga ttaaaacaca 2882 tgtaaattgc tctttagtag tggatactgt gtaagacaaa gccaaattgc aaatcaggct 2942 ttgattggct cttctggaaa atatgcatca aatatggggg ataatctgga tgggctgctg 3002 ctgtgctcaa tgtgaactat ttagatacct tggaacact taacagtttc tctgaacaat 3062 gacttacatg gggattggtc ctgtttgtca ttcctcacca taattgcatt gtcatcacta 3122 atccttggat cttgctgtat tgttactcaa attggtaata ggtactgatg gaaatcgcta 3182 atggatggat aatcataaca cttttggtca catgttttct cctgcagcct gaaagttctt 3242 aaagaaaag atatcaaatg cctgctgcta ccacccttt aaattgctat ctttagaaaa 3302 gcaccggtat gtgtttaga ttcatttccc tgttttaggg aaatgacagg cagtagtttc 3362

```
agttctgatg gcaaaacaaa taaaaacatg tttctaaaag ttgtatcttg aaacactggt    3422
gttcaacagc tagcagctaa agtaattcaa cccatgcatt gctagtgtca cagcctttgg    3482
ttatgtctag tagctgtttc tgaagtattt tcatttatct tttgtcaaat ttaaccctgt    3542
ttgaattctc tcctttcctc aaggagacac ttatgttcaa agtgttgatt ctttgcctta    3602
ggtgcataga gagtagacag tttggagatg gaaaggttag cagtgactta gccatatgtt    3662
ctgtgttgga atttgtgcta gcagtttgag cactagctct gcgtgcctat gaactgaatg    3722
ctgcttgtcc cattccattt tatgtcatgg agaaataatt ccacttggta acacaaaggc    3782
taagttaatg ttattttctg tacagaaatt aaatttact tttagccttt tgtaaacttt    3842
tttttttttt ttccaagccg gtatcagcta ctcaaaacaa ttctcagata ttcatcatta    3902
gacaactgga gttttgctg gttttgtagc ctactaaaac tgctgaggct gttgaacatt    3962
ccacattcaa aagttttgta gggtggtgga taatgggaa gcttcaatgt ttatttaaa    4022 ataaataaaa taagttcttg acttttctca tgtgtggtta tggtacatca tattggaagg    4082
gttatctgtt tacttttgcc aagactattt tgccagcacc tacacttgtg tgctttaaaa    4142
gacaactacc tgggatgtac cacaaccata tgttaattgt attttattgg gatggataaa    4202
atgtttgtgg tttattggat aatccctaga tggtgtgtta cgtgtgtaga atataatttt    4262
atgatagtaa gaaagcaaaa ttgaagaaaa taagtttagt attgaatttg agttctgaag    4322
tgaattcagg gaatgtctca cgtttcgggc ttctacccaa agtgtagggc agaaggtgta    4382
aaagttgttt gtagtttgac ttgtttattt tttaagttgc ttattccttt caacagcaac    4442
atatcattag ctgtcattct accattgcag ttctagtgag ttttaacgtc tgcattcaag    4502
actgttttaa aagcaacctc actggacaga gaactgctaa agtcttttcc ttaagatctg    4562
agtctttgtt actcagtatc ttctataata tgcaaatgct tgtctagagg cagaagacct    4622
tttgtttggt caagtgtgta ttttaccaga gtacagggaa ctgatggtcc tacatgtctc    4682
ttagtgtagt aagactataa aatctttgt acatgcacaa ttcacagtat gtttagatac    4742
cacgtgtata atgcccccc ctcccccagg tagcatgcca ttgatgactt tttgcttagg    4802
gccattttat taccagggcc ttaatattcc taaaaagatg attttttttc atcctttctc    4862
ctcttttgat cattgtatct tgatattaaa aacatgacct tccaatgatt gtagtaaatt    4922
aacttctata gttcttttgt ctctatatgt attcatatat atgctattgt atagagactt    4982
caaggagaca tggagatgca tgcttattct caggttcatt cactaaggtg cttggcagac    5042
aaccagtttc taagtgcaga atgtagttaa gcagcttcat atatgtgcca ggcaatttgt    5102
tttgttaaat tttcatctac ttaaggaaat agggtattgt agcttaggct gatcataccc    5162
ttcatttcaa ccttaagctc tcaacctgca tccatccgac ttgagctatt aagtacttta    5222
gttttatcga gtataagtta acagaaaaag taaattaagc tttgcctta ctattttgaa    5282 tttatataca ttctgaaaaa acttagaaac tgttgtatat ttcattagat taaattatat    5342
gaaaatgtga ttgtttatag caaagcctgt gagttgcata cacctaagg aaaactcctt    5402 aagtgctcct tgaagagaga agaaacaatt ctgggtctgg tcttttaag aacaaagcta    5462 gactactgta tgttagcact gtacattaat agtctgttgt gaagcttgag cagtttcctg    5522
catagccttg atccttcacc gttggcattg aaaatagcag tatccctgat gtacttaaaa    5582
cttaaagtca ggttttggta tatttatttg taagtcttaa tttcctctaa atactatatc    5642 tcttagcga gacaacctga aatttattag cacatttggg tatctcttgc ttggcattat    5702
ggccagtgtt aactattcag tggtgaaaaa attaccctc aagacactgg agtgaccca    5762
```

-continued

```
gatgtgtgta gtaagtggca tggttcaact gtgtggttaa tgataaatat atgacttagt    5822
cggtatgatc tggaaagact tgattgaaag ataattcagc tgacataagg atgagtgagg    5882
agtggcaaac tggataaaag agtcaagaga cctgtattcc agtgactcct gttttgttta    5942
agcattagca agatctgtct ggggaaactg gatagggcag ttttcttcca tgtttagttt    6002
ttgtctcaac atttggaagc tattgaaggt tttaaaatgg tgtgtattgt ttttttttgg    6062
ggggggggtg gccagaatag tgggtcatct aataaaactg ccatttaaaa gatcaaaaaa    6122
aaaaaaaaaa aaaaaaaaa                                                 6141
```

<210> SEQ ID NO 22
<211> LENGTH: 707
<212> TYPE: PRT
<213> ORGANISM: Mus musculus

<400> SEQUENCE: 22

```
Met Pro Ser Ala Thr Ser His Ser Gly Ser Gly Ser Lys Ser Gly
1               5                   10                  15

Pro Pro Pro Pro Ser Gly Ser Gly Ser Glu Ala Ala Gly Ala
                20                  25                  30

Ala Ala Pro Ala Ser Gln His Pro Ala Thr Gly Thr Gly Ala Val Gln
            35                  40                  45

Thr Glu Ala Met Lys Gln Ile Leu Gly Val Ile Asp Lys Lys Leu Arg
        50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
```

```
                305                 310                 315                 320
Val Val Asn Ser Leu Gln Gln Pro Gln Ala Ala Ser Pro Ser Val
            325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
            355                 360                 365

Asn Phe Ile Gln Asp Ser Met Leu Asp Phe Glu Asn Gln Thr Leu Asp
370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
            405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
            435                 440                 445

Pro Ser His Ala Thr Glu Gln Arg Pro Gln Lys Glu Pro Met Asp Gln
            450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
            485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
            515                 520                 525

Glu Pro Glu Thr Leu Lys Gln Gln Ser Gln Tyr Gln Ala Thr Tyr Asn
            530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
            565                 570                 575

Gln Pro His Gln Val Pro Gly Asn His Gln Gln Pro Gln Gln Asn
            580                 585                 590

Thr Gly Phe Pro Arg Ser Ser Gln Pro Tyr Tyr Asn Ser Arg Gly Val
            595                 600                 605

Ser Arg Gly Gly Ser Arg Gly Ala Arg Gly Leu Met Asn Gly Tyr Arg
            610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
            645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
            675                 680                 685

Gly Gly Pro Pro Arg Pro Asn Arg Gly Met Pro Gln Met Asn Thr Gln
            690                 695                 700

Gln Val Asn
705

<210> SEQ ID NO 23
<211> LENGTH: 6114
```

```
<212> TYPE: DNA
<213> ORGANISM: Mus musculus
<220> FEATURE:
<221> NAME/KEY: CDS
<222> LOCATION: (139)..(2235)
<223> OTHER INFORMATION:

<400> SEQUENCE: 23
cccaccgcgc gcgcgcgtag ccgcctgccc gcccgcccgc tgcgcgtttt gtcccgcgtc      60
tctccccgtc cgtctcctga cttgctggtc ttgtccttcc ctcccgcttt tttcctctcc     120
tctcttctcg gtctaaag atg ccc tcg gcc acc agc cac agc gga agc ggc       171
                    Met Pro Ser Ala Thr Ser His Ser Gly Ser Gly
                    1               5                   10 agc aaa tcg tcg gga ccg ccg ccg ccg tcc ggt tcc tcc ggg agt gag       219
Ser Lys Ser Ser Gly Pro Pro Pro Pro Ser Gly Ser Ser Gly Ser Glu
            15                  20                  25 gcg gcg gcc ggg gca gct gcg ccg gct tct cag cat ccg gca acc ggc       267
Ala Ala Ala Gly Ala Ala Ala Pro Ala Ser Gln His Pro Ala Thr Gly
        30                  35                  40 acc ggc gcc gtc cag acc gag gcc atg aag cag att ctc ggc gta atc       315
Thr Gly Ala Val Gln Thr Glu Ala Met Lys Gln Ile Leu Gly Val Ile
45                  50                  55 gac aag aaa ctt cgg aac ctg gag aag aaa aag ggt aaa ctt gat gat       363
Asp Lys Lys Leu Arg Asn Leu Glu Lys Lys Lys Gly Lys Leu Asp Asp
60                  65                  70                  75 tac cag gaa cga atg aat aaa ggg gaa agg ctc aat caa gac cag ctg       411
Tyr Gln Glu Arg Met Asn Lys Gly Glu Arg Leu Asn Gln Asp Gln Leu
                80                  85                  90 gat gcc gta tct aag tac cag gaa gtc aca aat aat ttg gag ttt gca       459
Asp Ala Val Ser Lys Tyr Gln Glu Val Thr Asn Asn Leu Glu Phe Ala
            95                  100                 105 aag gaa tta cag agg agt ttc atg gca tta agt caa gat att cag aaa       507
Lys Glu Leu Gln Arg Ser Phe Met Ala Leu Ser Gln Asp Ile Gln Lys
        110                 115                 120 aca ata aag aag aca gca cgt cgg gaa cag ctt atg aga gaa gaa gca       555
Thr Ile Lys Lys Thr Ala Arg Arg Glu Gln Leu Met Arg Glu Glu Ala
125                 130                 135 gaa cag aag cgc tta aaa act gta ctt gag tta cag tat gta ttg gat       603
Glu Gln Lys Arg Leu Lys Thr Val Leu Glu Leu Gln Tyr Val Leu Asp
140                 145                 150                 155 aag ctg gga gat gat gat gtg aga aca gat ctg aaa caa ggt ttg agt       651
Lys Leu Gly Asp Asp Asp Val Arg Thr Asp Leu Lys Gln Gly Leu Ser
                160                 165                 170 gga gtg cca ata ttg tct gag gag gag ttg tca ttg ctg gat gag ttc       699
Gly Val Pro Ile Leu Ser Glu Glu Glu Leu Ser Leu Leu Asp Glu Phe
            175                 180                 185 tac aag ctc gta gat cct gag cgt gac atg agt tta agg tta aat gag       747
Tyr Lys Leu Val Asp Pro Glu Arg Asp Met Ser Leu Arg Leu Asn Glu
        190                 195                 200 cag tat gaa cat gcc tca att cac ttg tgg gat ttg ctg gaa ggg aaa       795
Gln Tyr Glu His Ala Ser Ile His Leu Trp Asp Leu Leu Glu Gly Lys
205                 210                 215 gaa aag cct gtg tgt gga aca acc tat aaa gct cta aag gaa att gtt       843
Glu Lys Pro Val Cys Gly Thr Thr Tyr Lys Ala Leu Lys Glu Ile Val
220                 225                 230                 235 gag cgt gtt ttc cag tca aac tac ttt gat agc act cac aat cat caa       891
Glu Arg Val Phe Gln Ser Asn Tyr Phe Asp Ser Thr His Asn His Gln
                240                 245                 250 aat ggg ttg tgt gag gag gaa gag gcg gct tca gcg ccc aca gtg gag       939
Asn Gly Leu Cys Glu Glu Glu Glu Ala Ala Ser Ala Pro Thr Val Glu
            255                 260                 265
```

```
gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280 caa agt gag gtt gaa tca aca gag tat gtc aat agg cag ttc atg gca     1035
Gln Ser Glu Val Glu Ser Thr Glu Tyr Val Asn Arg Gln Phe Met Ala
285                 290                 295 gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315 gtt gaa aca gtt gag gtt gta aac tca ctc cag cag caa cct cag gct     1131
Val Glu Thr Val Glu Val Val Asn Ser Leu Gln Gln Gln Pro Gln Ala
        320                 325                 330 gcg tcc cct tca gtc cca gag ccc cac tct ttg act cca gtg gct cag     1179
Ala Ser Pro Ser Val Pro Glu Pro His Ser Leu Thr Pro Val Ala Gln
        335                 340                 345 tca gat cca ctt gtg aga agg cag cgt gta caa gat ctt atg gca caa     1227
Ser Asp Pro Leu Val Arg Arg Gln Arg Val Gln Asp Leu Met Ala Gln
        350                 355                 360 atg caa ggg ccc tat aat ttc ata cag acg ctt gat cct gcc att gta     1275
Met Gln Gly Pro Tyr Asn Phe Ile Gln Thr Leu Asp Pro Ala Ile Val
365                 370                 375 tcc gca cag cct atg aac cct acc cag aac atg gat atg cct cag ctg     1323
Ser Ala Gln Pro Met Asn Pro Thr Gln Asn Met Asp Met Pro Gln Leu
380                 385                 390                 395 gtt tgc cct cag gtt cat tct gaa tct aga ctt gcc caa tct aat caa     1371
Val Cys Pro Gln Val His Ser Glu Ser Arg Leu Ala Gln Ser Asn Gln
        400                 405                 410 gtt cct gta caa cca gaa gcc aca cag gtt cct ttg gtt tca tcc aca     1419
Val Pro Val Gln Pro Glu Ala Thr Gln Val Pro Leu Val Ser Ser Thr
        415                 420                 425 agt gag ggg tat aca gca tct cag ccc ttg tac cag cca tct cat gct     1467
Ser Glu Gly Tyr Thr Ala Ser Gln Pro Leu Tyr Gln Pro Ser His Ala
        430                 435                 440 acg gag cag cgg ccg cag aaa gag cca atg gat cag att cag gca aca     1515
Thr Glu Gln Arg Pro Gln Lys Glu Pro Met Asp Gln Ile Gln Ala Thr
        445                 450                 455 ata tct ttg aat aca gac cag act aca gca tcc tca tcc ctt cct gct     1563
Ile Ser Leu Asn Thr Asp Gln Thr Thr Ala Ser Ser Ser Leu Pro Ala
460                 465                 470                 475 gct tct cag cct caa gtg ttc cag gct ggg aca agt aaa cct ttg cac     1611
Ala Ser Gln Pro Gln Val Phe Gln Ala Gly Thr Ser Lys Pro Leu His
                480                 485                 490 agc agt gga atc aat gta aat gca gct cca ttc cag tcc atg caa acg     1659
Ser Ser Gly Ile Asn Val Asn Ala Ala Pro Phe Gln Ser Met Gln Thr
        495                 500                 505 gtg ttc aat atg aat gct cca gtc cct cct gct aat gaa cca gaa acg     1707
Val Phe Asn Met Asn Ala Pro Val Pro Pro Ala Asn Glu Pro Glu Thr
        510                 515                 520 tta aaa caa cag agt cag tac cag gcc act tat aac cag agt ttt tcc     1755
Leu Lys Gln Gln Ser Gln Tyr Gln Ala Thr Tyr Asn Gln Ser Phe Ser
525                 530                 535 agt cag cct cac caa gtg gaa caa aca gag ctt caa caa gac caa ctg     1803
Ser Gln Pro His Gln Val Glu Gln Thr Glu Leu Gln Gln Asp Gln Leu
540                 545                 550                 555 caa acg gtg gtt ggc act tac cat gga tcc cag gac cag cct cat caa     1851
Gln Thr Val Val Gly Thr Tyr His Gly Ser Gln Asp Gln Pro His Gln
                560                 565                 570 gtg cct ggt aac cac cag caa ccc cca cag cag aac act ggc ttt cca     1899
Val Pro Gly Asn His Gln Gln Pro Pro Gln Gln Asn Thr Gly Phe Pro
        575                 580                 585
```

| | | |
|---|---|---|
| cgt agc agt cag cct tat tac aac agt cgt ggg gta tct cga gga ggg<br>Arg Ser Ser Gln Pro Tyr Tyr Asn Ser Arg Gly Val Ser Arg Gly Gly<br>590                   595                   600 | 1947 |
| tct cgt ggt gcc aga ggc ttg atg aat gga tac agg ggc cct gcc aat<br>Ser Arg Gly Ala Arg Gly Leu Met Asn Gly Tyr Arg Gly Pro Ala Asn<br>605                   610                   615 | 1995 |
| gga ttt aga gga gga tat gat ggt tac cgc cct tca ttc tcg aac act<br>Gly Phe Arg Gly Gly Tyr Asp Gly Tyr Arg Pro Ser Phe Ser Asn Thr<br>620                   625                   630                   635 | 2043 |
| cca aac agt ggt tat tca cag tct cag ttc act gct ccc cgg gac tac<br>Pro Asn Ser Gly Tyr Ser Gln Ser Gln Phe Thr Ala Pro Arg Asp Tyr<br>                   640                   645                   650 | 2091 |
| tct ggt tac cag cgg gat gga tat cag cag aat ttc aag cga ggc tct<br>Ser Gly Tyr Gln Arg Asp Gly Tyr Gln Gln Asn Phe Lys Arg Gly Ser<br>655                   660                   665 | 2139 |
| ggg cag agt gga cca cgg gga gcc cca cga ggt cgt gga ggg ccc cca<br>Gly Gln Ser Gly Pro Arg Gly Ala Pro Arg Gly Arg Gly Gly Pro Pro<br>670                   675                   680 | 2187 |
| aga ccc aac aga ggg atg ccg caa atg aac act cag caa gtg aat taa<br>Arg Pro Asn Arg Gly Met Pro Gln Met Asn Thr Gln Gln Val Asn<br>685                   690                   695 | 2235 |
| tgtgatacac aggattatgt ttaatcgcca aaaacacact ggccagtgta ccataatatg | 2295 |
| ttaccagaag agttattatc tatttgttct cccttcagg aaacttattg taaagggact | 2355 |
| gttttcatcc cataaagaca ggactgcaat tgtcagcttt acattacctg gatatggaag | 2415 |
| gaaactattt ttattctgca tgttctgtcc taagcgtcat cttgagcctt gcacacaata | 2475 |
| caatactcag attcctcacc cttgcttagg agtaaaacat tatatactta tggggtgata | 2535 |
| atatctccat agttagttga agtggcttgg aaaaaaaatg caagattgaa tttttgacct | 2595 |
| tggataaaat ctacaatcag ccctagaact attcagtggt aattgacaaa gttaaagcat | 2655 |
| tttctttgaa aggaagatgg aaggagtgga gtgtggttta gcaaaactgc atttcatagc | 2715 |
| tttcccatta aattggagca ccgacagatt aaaagcatac caaattatgc atgggtcctt | 2775 |
| actcacacaa gtgaggctgg ctaccagcct tgacatagca ctcactagtc ttctggccaa | 2835 |
| acgactgtga ttaaaacaca tgtaaattgc tctttagtag tggatactgt gtaagacaaa | 2895 |
| gccaaattgc aaatcaggct ttgattggct cttctggaaa atatgcatca aatatggggg | 2955 |
| ataatctgga tgggctgctg ctgtgctcaa tgtgaactat ttagatacct ttggaacact | 3015 |
| taacagtttc tctgaacaat gacttacatg gggattggtc ctgtttgtca ttcctcacca | 3075 |
| taattgcatt gtcatcacta atccttggat cttgctgtat tgttactcaa attggtaata | 3135 |
| ggtactgatg gaaatcgcta atggatggat aatcataaca cttttggtca catgtttttct | 3195 |
| cctgcagcct gaaagttctt aaagaaaaag atatcaaatg cctgctgcta ccacccttt | 3255 |
| aaattgctat ctttagaaaa gcaccggtat gtgttttaga ttcatttccc tgttttaggg | 3315 |
| aaatgacagg cagtagtttc agttctgatg gcaaaacaaa taaaaacatg tttctaaaag | 3375 |
| ttgtatcttg aaacactggt gttcaacagc tagcagctaa agtaattcaa cccatgcatt | 3435 |
| gctagtgtca cagcctttgg ttatgtctag tagctgtttc tgaagtattt tcatttatct | 3495 |
| tttgtcaaat ttaaccctgt ttgaattctc tcctttcctc aaggagacac ttatgttcaa | 3555 |
| agtgttgatt ctttgcctta ggtgcataga gagtagacag tttggagatg gaaaggttag | 3615 |
| cagtgactta gccatatgtt ctgtgttgga atttgtgcta gcagtttgag cactagctct | 3675 |
| gcgtgcctat gaactgaatg ctgcttgtcc cattccattt tatgtcatgg agaaataatt | 3735 |
| ccacttggta acacaaaggc taagttaatg ttatttttctg tacagaaatt aaatttact | 3795 |

```
tttagcctttt tgtaaacttt ttttttttttt ttccaagccg gtatcagcta ctcaaaacaa    3855
ttctcagata ttcatcatta gacaactgga gttttgctg gttttgtagc ctactaaaac     3915
tgctgaggct gttgaacatt ccacattcaa aagttttgta gggtggtgga taatgggaa      3975 gcttcaatgt ttatttaaa ataaataaaa taagttcttg acttttctca tgtgtggtta     4035
tggtacatca tattggaagg gttatctgtt tacttttgcc aagactattt tgccagcacc    4095
tacacttgtg tgcttttaaaa gacaactacc tgggatgtac cacaaccata tgttaattgt   4155
attttattgg gatggataaa atgtttgtgg tttattggat aatccctaga tggtgtgtta    4215
cgtgtgtaga atataatttt atgatagtaa gaaagcaaaa ttgaagaaaa taagtttagt    4275
attgaatttg agttctgaag tgaattcagg gaatgtctca cgtttcgggc ttctacccaa    4335
agtgtagggc agaaggtgta aaagttgttt gtagtttgac ttgtttatt tttaagttgc     4395 ttattccttt caacagcaac atatcattag ctgtcattct accattgcag ttctagtgag    4455
ttttaacgtc tgcattcaag actgttttaa aagcaacctc actggacaga gaactgctaa    4515
agtcttttcc ttaagatctg agtctttgtt actcagtatc ttctataata tgcaaatgct    4575
tgtctagagg cagaagacct tttgtttggt caagtgtgta ttttaccaga gtacagggaa    4635
ctgatggtcc tacatgtctc ttagtgtagt aagactataa aatcttttgt acatgcacaa    4695
ttcacagtat gtttagatac cacgtgtata atgcccccc ctcccccagg tagcatgcca     4755
ttgatgactt tttgcttagg gccatttat taccagggcc ttaatattcc taaaagatg      4815 attttttttc atcctttctc ctcttttgat cattgtatct tgatattaaa aacatgacct    4875
tccaatgatt gtagtaaatt aacttctata gttcttttgt ctctatatgt attcatatat    4935
atgctattgt atagagactt caaggagaca tggagatgca tgcttattct caggttcatt    4995
cactaaggtg cttggcagac aaccagtttc taagtgcaga atgtagttaa gcagcttcat   5055
atatgtgcca ggcaatttgt tttgttaaat tttcatctac ttaaggaaat agggtattgt   5115
agcttaggct gatcataccc ttcatttcaa ccttaagctc tcaacctgca tccatccgac    5175
ttgagctatt aagtacttta gttttatcga gtataagtta acagaaaaag taaattaagc    5235
tttgccttta ctattttgaa tttatataca ttctggaaaa acttagaaac tgttgtatat    5295
ttcattagat taaattatat gaaaatgtga ttgtttatag caaagcctgt gagttgcata    5355 cacccctaagg aaaactcctt aagtgctcct tgaagagaga agaaacaatt ctgggtctgg   5415 tcttttaag aacaaagcta gactactgta tgttagcact gtacattaat agtctgttgt     5475
gaagcttgag cagtttcctg catagccttg atccttcacc gttggcattg aaaatagcag    5535
tatccctgat gtacttaaaa cttaaagtca ggttttggta tatttatttg taagtcttaa    5595
tttcctctaa atactatatc tctttagcga gacaacctga aatttattag cacatttggg   5655
tatctcttgc ttggcattat ggccagtgtt aactattcag tggtgaaaaa attacccctc   5715
aagacactgg agtgaccca gatgtgtgta gtaagtggca tggttcaact gtgtggttaa     5775
tgataaatat atgacttagt cggtatgatc tggaaagact tgattgaaag ataattcagc   5835
tgacataagg atgagtgagg agtggcaaac tggataaaag agtcaagaga cctgtattcc    5895
agtgactcct gttttgttta agcattagca agatctgtct ggggaaactg gataggggcag   5955 ttttcttcca tgtttagttt ttgtctcaac atttggaagc tattgaaggt tttaaaatgg    6015
tgtgtattgt ttttttttgg ggggggggtg gccagaatag tgggtcatct aataaaactg    6075
ccatttaaaa gatcaaaaaa aaaaaaaaaa aaaaaaaa                            6114
```

-continued

```
<210> SEQ ID NO 24
<211> LENGTH: 698
<212> TYPE: PRT
<213> ORGANISM: Mus musculus

<400> SEQUENCE: 24
```

Met Pro Ser Ala Thr Ser His Ser Gly Ser Gly Ser Lys Ser Ser Gly
1               5                   10                  15

Pro Pro Pro Ser Gly Ser Ser Gly Ser Glu Ala Ala Gly Ala
            20                  25                  30

Ala Ala Pro Ala Ser Gln His Pro Ala Thr Gly Thr Gly Ala Val Gln
            35                  40                  45

Thr Glu Ala Met Lys Gln Ile Leu Gly Val Ile Asp Lys Lys Leu Arg
    50                  55                  60

Asn Leu Glu Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Thr Leu Asp Pro Ala Ile Val Ser Ala Gln Pro Met
    370                 375                 380

Asn Pro Thr Gln Asn Met Asp Met Pro Gln Leu Val Cys Pro Gln Val

```
                385                 390                 395                 400
His Ser Glu Ser Arg Leu Ala Gln Ser Asn Gln Val Pro Val Gln Pro
                    405                 410                 415

Glu Ala Thr Gln Val Pro Leu Val Ser Thr Ser Glu Gly Tyr Thr
            420                 425                 430

Ala Ser Gln Pro Leu Tyr Gln Pro Ser His Ala Thr Glu Gln Arg Pro
            435                 440                 445

Gln Lys Glu Pro Met Asp Gln Ile Gln Ala Thr Ile Ser Leu Asn Thr
    450                 455                 460

Asp Gln Thr Thr Ala Ser Ser Ser Leu Pro Ala Ala Ser Gln Pro Gln
465                 470                 475                 480

Val Phe Gln Ala Gly Thr Ser Lys Pro Leu His Ser Ser Gly Ile Asn
                485                 490                 495

Val Asn Ala Ala Pro Phe Gln Ser Met Gln Thr Val Phe Asn Met Asn
            500                 505                 510

Ala Pro Val Pro Pro Ala Asn Glu Pro Glu Thr Leu Lys Gln Gln Ser
        515                 520                 525

Gln Tyr Gln Ala Thr Tyr Asn Gln Ser Phe Ser Ser Gln Pro His Gln
    530                 535                 540

Val Glu Gln Thr Glu Leu Gln Gln Asp Gln Leu Gln Thr Val Val Gly
545                 550                 555                 560

Thr Tyr His Gly Ser Gln Asp Gln Pro His Gln Val Pro Gly Asn His
                565                 570                 575

Gln Gln Pro Pro Gln Gln Asn Thr Gly Phe Pro Arg Ser Ser Gln Pro
            580                 585                 590

Tyr Tyr Asn Ser Arg Gly Val Ser Arg Gly Gly Ser Arg Gly Ala Arg
        595                 600                 605

Gly Leu Met Asn Gly Tyr Arg Gly Pro Ala Asn Gly Phe Arg Gly Gly
    610                 615                 620

Tyr Asp Gly Tyr Arg Pro Ser Phe Ser Asn Thr Pro Asn Ser Gly Tyr
625                 630                 635                 640

Ser Gln Ser Gln Phe Thr Ala Pro Arg Asp Tyr Ser Gly Tyr Gln Arg
                645                 650                 655

Asp Gly Tyr Gln Gln Asn Phe Lys Arg Gly Ser Gly Gln Ser Gly Pro
            660                 665                 670

Arg Gly Ala Pro Arg Gly Arg Gly Gly Pro Pro Arg Pro Asn Arg Gly
        675                 680                 685

Met Pro Gln Met Asn Thr Gln Gln Val Asn
    690                 695

<210> SEQ ID NO 25
<211> LENGTH: 3548
<212> TYPE: DNA
<213> ORGANISM: Mus musculus
<220> FEATURE:
<221> NAME/KEY: CDS
<222> LOCATION: (179)..(2257)
<223> OTHER INFORMATION:

<400> SEQUENCE: 25
gctggctggc taagtccctc ccgcgccggc tcttgtccca ctaggagcag ctcagagccg      60
cggggacagg gcgaagcggc ctgcgcccac ggagcgcacg tctctgttct caacgcagca     120
ccacccttgc cccctcggc tgccactcc agacgtccag cggctccgcg cgcgcacg         178 atg ccc tcg gcc acc agc cac agc gga agc ggc agc aaa tcg tcg gga      226
Met Pro Ser Ala Thr Ser His Ser Gly Ser Gly Ser Lys Ser Ser Gly
1               5                   10                  15
```

|  |  |
|---|---|
| ccg ccg ccg ccg tcc ggt tcc tcc ggg agt gag gcg gcg gcc ggg gca<br>Pro Pro Pro Pro Ser Gly Ser Ser Gly Ser Glu Ala Ala Ala Gly Ala<br>            20                    25                     30 | 274 |
| gct gcc ccg gct tct cag cat ccg gca acc ggc acc ggc gcc gtc cag<br>Ala Ala Pro Ala Ser Gln His Pro Ala Thr Gly Thr Gly Ala Val Gln<br>            35                    40                     45 | 322 |
| acc gag gcc atg aag cag att ctc ggc gta atc gac aag aaa ctt cgg<br>Thr Glu Ala Met Lys Gln Ile Leu Gly Val Ile Asp Lys Lys Leu Arg<br>50                    55                    60 | 370 |
| aac ctg gag aag aaa aag ggt aaa ctt gat gat tac cag gaa cga atg<br>Asn Leu Glu Lys Lys Lys Gly Lys Leu Asp Asp Tyr Gln Glu Arg Met<br>65                    70                    75                    80 | 418 |
| aat aaa ggg gaa agg ctc aat caa gac cag ctg gat gcc gta tct aag<br>Asn Lys Gly Glu Arg Leu Asn Gln Asp Gln Leu Asp Ala Val Ser Lys<br>            85                    90                     95 | 466 |
| tac cag gaa gtc aca aat aat ttg gag ttt gca aag gaa tta cag agg<br>Tyr Gln Glu Val Thr Asn Asn Leu Glu Phe Ala Lys Glu Leu Gln Arg<br>           100                    105                 110 | 514 |
| agt ttc atg gca tta agt caa gat att cag aaa aca ata aag aag aca<br>Ser Phe Met Ala Leu Ser Gln Asp Ile Gln Lys Thr Ile Lys Lys Thr<br>          115                    120                 125 | 562 |
| gca cgt cgg gaa cag ctt atg aga gaa gaa gca gaa cag aag cgc tta<br>Ala Arg Arg Glu Gln Leu Met Arg Glu Glu Ala Glu Gln Lys Arg Leu<br>130                    135                    140 | 610 |
| aaa act gta ctt gag tta cag tat gta ttg gat aag ctg gga gat gat<br>Lys Thr Val Leu Glu Leu Gln Tyr Val Leu Asp Lys Leu Gly Asp Asp<br>145                    150                 155                 160 | 658 |
| gat gtg aga aca gat ctg aaa caa ggt ttg agt gga gtg cca ata ttg<br>Asp Val Arg Thr Asp Leu Lys Gln Gly Leu Ser Gly Val Pro Ile Leu<br>                165                    170                 175 | 706 |
| tct gag gag gag ttg tca ttg ctg gat gag ttc tac aag ctc gta gat<br>Ser Glu Glu Glu Leu Ser Leu Leu Asp Glu Phe Tyr Lys Leu Val Asp<br>          180                    185                 190 | 754 |
| cct gag cgt gac atg agt tta agg tta aat gag cag tat gaa cat gcc<br>Pro Glu Arg Asp Met Ser Leu Arg Leu Asn Glu Gln Tyr Glu His Ala<br>                195                    200                 205 | 802 |
| tca att cac ttg tgg gat ttg ctg gaa ggg aaa gaa aag cct gtg tgt<br>Ser Ile His Leu Trp Asp Leu Leu Glu Gly Lys Glu Lys Pro Val Cys<br>210                    215                    220 | 850 |
| gga aca acc tat aaa gct cta aag gaa att gtt gag cgt gtt ttc cag<br>Gly Thr Thr Tyr Lys Ala Leu Lys Glu Ile Val Glu Arg Val Phe Gln<br>225                    230                 235                 240 | 898 |
| tca aac tac ttt gat agc act cac aat cat caa aat ggg ttg tgt gag<br>Ser Asn Tyr Phe Asp Ser Thr His Asn His Gln Asn Gly Leu Cys Glu<br>          245                    250                 255 | 946 |
| gag gaa gag gcg gct tca gcg ccc aca gtg gag gac cag gta gct gaa<br>Glu Glu Glu Ala Ala Ser Ala Pro Thr Val Glu Asp Gln Val Ala Glu<br>                260                    265                 270 | 994 |
| gct gaa cct gag cca gcg gaa gaa tac aca gag caa agt gag gtt gaa<br>Ala Glu Pro Glu Pro Ala Glu Glu Tyr Thr Glu Gln Ser Glu Val Glu<br>          275                    280                 285 | 1042 |
| tca aca gag tat gtc aat agg cag ttc atg gca gaa aca cag ttc agc<br>Ser Thr Glu Tyr Val Asn Arg Gln Phe Met Ala Glu Thr Gln Phe Ser<br>290                    295                    300 | 1090 |
| agt ggt gag aag gag caa gtg gat gag tgg aca gtt gaa aca gtt gag<br>Ser Gly Glu Lys Glu Gln Val Asp Glu Trp Thr Val Glu Thr Val Glu<br>305                    310                 315                 320 | 1138 |
| gtt gta aac tca ctc cag cag caa cct cag gct gcg tcc cct tca gtc<br>Val Val Asn Ser Leu Gln Gln Gln Pro Gln Ala Ala Ser Pro Ser Val<br>                325                    330                 335 | 1186 |

| | | | | | | | | | | | | | | | | |
|---|---|---|---|---|---|---|---|---|---|---|---|---|---|---|---|---|
| cca | gag | ccc | cac | tct | ttg | act | cca | gtg | gct | cag | tca | gat | cca | ctt | gtg | 1234 |
| Pro | Glu | Pro | His | Ser | Leu | Thr | Pro | Val | Ala | Gln | Ser | Asp | Pro | Leu | Val | |
| | | | 340 | | | | 345 | | | | | 350 | | | | |
| aga | agg | cag | cgt | gta | caa | gat | ctt | atg | gca | caa | atg | caa | ggg | ccc | tat | 1282 |
| Arg | Arg | Gln | Arg | Val | Gln | Asp | Leu | Met | Ala | Gln | Met | Gln | Gly | Pro | Tyr | |
| | | | | 355 | | | | 360 | | | | | 365 | | | |
| aat | ttc | ata | cag | gat | tca | atg | ttg | gat | ttt | gaa | aat | cag | acg | ctt | gat | 1330 |
| Asn | Phe | Ile | Gln | Asp | Ser | Met | Leu | Asp | Phe | Glu | Asn | Gln | Thr | Leu | Asp | |
| | | | 370 | | | | 375 | | | | 380 | | | | | |
| cct | gcc | att | gta | tcc | gca | cag | cct | atg | aac | cct | acc | cag | aac | atg | gat | 1378 |
| Pro | Ala | Ile | Val | Ser | Ala | Gln | Pro | Met | Asn | Pro | Thr | Gln | Asn | Met | Asp | |
| 385 | | | | | 390 | | | | | 395 | | | | | 400 | |
| atg | cct | cag | ctg | gtt | tgc | cct | cag | gtt | cat | tct | gaa | tct | aga | ctt | gcc | 1426 |
| Met | Pro | Gln | Leu | Val | Cys | Pro | Gln | Val | His | Ser | Glu | Ser | Arg | Leu | Ala | |
| | | | | | 405 | | | | | 410 | | | | | 415 | |
| caa | tct | aat | caa | gtt | cct | gta | caa | cca | gaa | gcc | aca | cag | gtt | cct | ttg | 1474 |
| Gln | Ser | Asn | Gln | Val | Pro | Val | Gln | Pro | Glu | Ala | Thr | Gln | Val | Pro | Leu | |
| | | | 420 | | | | | 425 | | | | | 430 | | | |
| gtt | tca | tcc | aca | agt | gag | ggg | tat | aca | gca | tct | cag | ccc | ttg | tac | cag | 1522 |
| Val | Ser | Ser | Thr | Ser | Glu | Gly | Tyr | Thr | Ala | Ser | Gln | Pro | Leu | Tyr | Gln | |
| | | | 435 | | | | | 440 | | | | | 445 | | | |
| cca | tct | cat | gct | acg | gag | cag | cgg | ccg | cag | aaa | gag | cca | atg | gat | cag | 1570 |
| Pro | Ser | His | Ala | Thr | Glu | Gln | Arg | Pro | Gln | Lys | Glu | Pro | Met | Asp | Gln | |
| | 450 | | | | | 455 | | | | | 460 | | | | | |
| att | cag | gca | aca | ata | tct | ttg | aat | aca | gac | cag | act | aca | gca | tcc | tca | 1618 |
| Ile | Gln | Ala | Thr | Ile | Ser | Leu | Asn | Thr | Asp | Gln | Thr | Thr | Ala | Ser | Ser | |
| 465 | | | | | 470 | | | | | 475 | | | | | 480 | |
| tcc | ctt | cct | gct | gct | tct | cag | cct | caa | gtg | ttc | cag | gct | ggg | aca | agt | 1666 |
| Ser | Leu | Pro | Ala | Ala | Ser | Gln | Pro | Gln | Val | Phe | Gln | Ala | Gly | Thr | Ser | |
| | | | | 485 | | | | | 490 | | | | | 495 | | |
| aaa | cct | ttg | cac | agc | agt | gga | atc | aat | gta | aat | gca | gct | cca | ttc | cag | 1714 |
| Lys | Pro | Leu | His | Ser | Ser | Gly | Ile | Asn | Val | Asn | Ala | Ala | Pro | Phe | Gln | |
| | | | 500 | | | | | 505 | | | | | 510 | | | |
| tcc | atg | caa | acg | gtg | ttc | aat | atg | aat | gct | cca | gtc | cct | cct | gct | aat | 1762 |
| Ser | Met | Gln | Thr | Val | Phe | Asn | Met | Asn | Ala | Pro | Val | Pro | Pro | Ala | Asn | |
| | | | 515 | | | | | 520 | | | | | 525 | | | |
| gaa | cca | gaa | acg | tta | aaa | caa | cag | agt | cag | tac | cag | gcc | act | tat | aac | 1810 |
| Glu | Pro | Glu | Thr | Leu | Lys | Gln | Gln | Ser | Gln | Tyr | Gln | Ala | Thr | Tyr | Asn | |
| | 530 | | | | | 535 | | | | | 540 | | | | | |
| cag | agt | ttt | tcc | agt | cag | cct | cac | caa | gtg | gaa | caa | aca | gag | ctt | caa | 1858 |
| Gln | Ser | Phe | Ser | Ser | Gln | Pro | His | Gln | Val | Glu | Gln | Thr | Glu | Leu | Gln | |
| 545 | | | | | 550 | | | | | 555 | | | | | 560 | |
| caa | gac | caa | ctg | caa | acg | gtg | gtt | ggc | act | tac | cat | gga | tcc | cag | gac | 1906 |
| Gln | Asp | Gln | Leu | Gln | Thr | Val | Val | Gly | Thr | Tyr | His | Gly | Ser | Gln | Asp | |
| | | | | 565 | | | | | 570 | | | | | 575 | | |
| cag | cct | cat | caa | gtg | cct | ggt | aac | cac | cag | caa | ccc | cca | cag | cag | aac | 1954 |
| Gln | Pro | His | Gln | Val | Pro | Gly | Asn | His | Gln | Gln | Pro | Pro | Gln | Gln | Asn | |
| | | | 580 | | | | | 585 | | | | | 590 | | | |
| act | ggc | ttt | cca | cgt | agc | agt | cag | cct | tat | tac | aac | agt | cgt | ggg | gta | 2002 |
| Thr | Gly | Phe | Pro | Arg | Ser | Ser | Gln | Pro | Tyr | Tyr | Asn | Ser | Arg | Gly | Val | |
| | | | 595 | | | | | 600 | | | | | 605 | | | |
| tct | cga | gga | ggg | tct | cgt | ggt | gcc | aga | ggc | ttg | atg | aat | gga | tac | agg | 2050 |
| Ser | Arg | Gly | Gly | Ser | Arg | Gly | Ala | Arg | Gly | Leu | Met | Asn | Gly | Tyr | Arg | |
| | | 610 | | | | | 615 | | | | | 620 | | | | |
| ggc | cct | gcc | aat | gga | ttt | aga | gga | gga | tat | gat | ggt | tac | cgc | cct | tca | 2098 |
| Gly | Pro | Ala | Asn | Gly | Phe | Arg | Gly | Gly | Tyr | Asp | Gly | Tyr | Arg | Pro | Ser | |
| 625 | | | | | 630 | | | | | 635 | | | | | 640 | |
| ttc | tcg | aac | act | cca | aac | agt | ggt | tat | tca | cag | tct | cag | ttc | act | gct | 2146 |
| Phe | Ser | Asn | Thr | Pro | Asn | Ser | Gly | Tyr | Ser | Gln | Ser | Gln | Phe | Thr | Ala | |
| | | | | 645 | | | | | 650 | | | | | 655 | | |

```
ccc cgg gac tac tct ggt tac cag cgg gat gga tat cag cag aat ttc      2194
Pro Arg Asp Tyr Ser Gly Tyr Gln Arg Asp Gly Tyr Gln Gln Asn Phe
            660                 665                 670 aag cga ggc tct ggg cag agt gga cca cgg gga gcc cca cga ggt aat      2242
Lys Arg Gly Ser Gly Gln Ser Gly Pro Arg Gly Ala Pro Arg Gly Asn
675                 680                 685 ata ttg tgg tgg tga cctagctcc tatgtggagc ttctgttctg gccttggaag       2297
Ile Leu Trp Trp
    690 aactgttcat agtccgcatg taggttacat gttaggaata catttatctt ttccagactt    2357 gttgctaaag attaaatgaa atgctctgtt tctaaaattt catcttgaat ccaaatttta    2417 attttgaat gactttccct gctgttgtct tcaaaatcag acatttcct ctgcctcaga      2477 aaagcgtttt tccaactgga aatttatttt tcaggtctta aaacctgcta atgttttta    2537 ggaagtacct actgaaactt tttgtaagac attttggaa cgagcttgaa catttatata    2597 aatttattac cctctttgat ttttgaaaca tgcatattat atttaggctg agaagccctt    2657 caaatggcca gataagccac agttttagct agagaaccat ttagaattga cataactaat    2717 ctaaacttga acacttttag gaccaatgtt agtgttctaa ataccaacat atttctgatg    2777 tttaaacaga tctcccaaat tcttaggacc ttgatgtcat taaaatttag aatgacaagc    2837 ttaagaggct ttagtttcat ttgtttttca agtaatgaaa ataatttct tacatgggca     2897 gatagttaat ttgttgaaca attacaggta gcatttcatg taatctgatg ttctaaatgg    2957 ttctcttatt gaaggaggtt aaagaattag gtttcttaca gttttggct ggccatgaca     3017 tgtataaaat gtatattaag gaggaattat aaagtacttt aatttgaatg ctagtggcaa    3077 ttgatcatta agaaagtact ttaaagcaaa aggttaatgg gtcatctggg aaaaatactg    3137 aagtatcaaa ggtatttgca tgtgaatgtg ggttatgttc ttctatccca ccttgtagca    3197 tattctatga aagttgagtt aaatgatagc taaaatatct gtttcaacag catgtaaaaa    3257 gttattttaa ctgttacaag tcattataca attttgaatg ttctgtagtt tcttttaac     3317 agtttaggta caaggtctg ttttcattct ggtgcttttt attaattttg atagtatgat     3377 gtcacttcct attgaaatgt aagctagcgt gtaccttaga atgtgagctc catgagagca    3437 ggtaccttgt ttgtcttcac tgctgtatct attcccaacg cctcatgaca gtgcctggca    3497 catagtaggc actcaataaa tacttgttga atgaatgaaa aaaaaaaaa a              3548

<210> SEQ ID NO 26
<211> LENGTH: 692
<212> TYPE: PRT
<213> ORGANISM: Mus musculus

<400> SEQUENCE: 26

Met Pro Ser Ala Thr Ser His Ser Gly Ser Gly Ser Lys Ser Gly
1               5                   10                  15

Pro Pro Pro Pro Ser Gly Ser Ser Gly Ser Glu Ala Ala Gly Ala
                20                  25                  30

Ala Ala Pro Ala Ser Gln His Pro Ala Thr Gly Thr Gly Ala Val Gln
            35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95
```

```
Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
```

```
                   515                 520                 525
Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Gln Gln Asn
            580                 585                 590

Thr Gly Phe Pro Arg Ser Ser Gln Pro Tyr Tyr Asn Ser Arg Gly Val
            595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690

<210> SEQ ID NO 27
<211> LENGTH: 3508
<212> TYPE: DNA
<213> ORGANISM: Mus musculus
<220> FEATURE:
<221> NAME/KEY: CDS
<222> LOCATION: (139)..(2217)
<223> OTHER INFORMATION:

<400> SEQUENCE: 27
cccaccgcgc gcgcgcgtag ccgcctgccc gcccgcccgc tgcgcgtttt gtcccgcgtc      60
tctccccgtc cgtctcctga cttgctggtc ttgtccttcc ctcccgcttt tttcctctcc     120
tctcttctcg gtctaaag atg ccc tcg gcc acc agc cac agc gga agc ggc       171
                    Met Pro Ser Ala Thr Ser His Ser Gly Ser Gly
                      1               5                  10 agc aaa tcg tcg gga ccg ccg ccg ccg tcc ggt tcc tcc ggg agt gag      219
Ser Lys Ser Ser Gly Pro Pro Pro Pro Ser Gly Ser Ser Gly Ser Glu
            15                  20                  25 gcg gcg gcc ggg gca gct gcg ccg gct tct cag cat ccg gca acc ggc      267
Ala Ala Ala Gly Ala Ala Ala Pro Ala Ser Gln His Pro Ala Thr Gly
        30                  35                  40 acc ggc gcc gtc cag acc gag gcc atg aag cag att ctc ggc gta atc      315
Thr Gly Ala Val Gln Thr Glu Ala Met Lys Gln Ile Leu Gly Val Ile
    45                  50                  55 gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60                  65                  70                  75 tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90 gat gcc gta tct aag tac cag gaa gtc aca aat aat ttg gag ttt gca      459
Asp Ala Val Ser Lys Tyr Gln Glu Val Thr Asn Asn Leu Glu Phe Ala
            95                 100                 105 aag gaa tta cag agg agt ttc atg gca tta agt caa gat att cag aaa      507
```

```
                Lys Glu Leu Gln Arg Ser Phe Met Ala Leu Ser Gln Asp Ile Gln Lys
                        110                 115                 120 aca ata aag aag aca gca cgt cgg gaa cag ctt atg aga gaa gaa gca              555
Thr Ile Lys Lys Thr Ala Arg Arg Glu Gln Leu Met Arg Glu Glu Ala
            125                 130                 135 gaa cag aag cgc tta aaa act gta ctt gag tta cag tat gta ttg gat              603
Glu Gln Lys Arg Leu Lys Thr Val Leu Glu Leu Gln Tyr Val Leu Asp
140                 145                 150                 155 aag ctg gga gat gat gat gtg aga aca gat ctg aaa caa ggt ttg agt              651
Lys Leu Gly Asp Asp Asp Val Arg Thr Asp Leu Lys Gln Gly Leu Ser
                160                 165                 170 gga gtg cca ata ttg tct gag gag gag ttg tca ttg ctg gat gag ttc              699
Gly Val Pro Ile Leu Ser Glu Glu Glu Leu Ser Leu Leu Asp Glu Phe
            175                 180                 185 tac aag ctc gta gat cct gag cgt gac atg agt tta agg tta aat gag              747
Tyr Lys Leu Val Asp Pro Glu Arg Asp Met Ser Leu Arg Leu Asn Glu
        190                 195                 200 cag tat gaa cat gcc tca att cac ttg tgg gat ttg ctg gaa ggg aaa              795
Gln Tyr Glu His Ala Ser Ile His Leu Trp Asp Leu Leu Glu Gly Lys
    205                 210                 215 gaa aag cct gtg tgt gga aca acc tat aaa gct cta aag gaa att gtt              843
Glu Lys Pro Val Cys Gly Thr Thr Tyr Lys Ala Leu Lys Glu Ile Val
220                 225                 230                 235 gag cgt gtt ttc cag tca aac tac ttt gat agc act cac aat cat caa              891
Glu Arg Val Phe Gln Ser Asn Tyr Phe Asp Ser Thr His Asn His Gln
                240                 245                 250 aat ggg ttg tgt gag gag gaa gag gcg gct tca gcg ccc aca gtg gag              939
Asn Gly Leu Cys Glu Glu Glu Glu Ala Ala Ser Ala Pro Thr Val Glu
            255                 260                 265 gac cag gta gct gaa gct gaa cct gag cca gcg gaa gaa tac aca gag              987
Asp Gln Val Ala Glu Ala Glu Pro Glu Pro Ala Glu Glu Tyr Thr Glu
        270                 275                 280 caa agt gag gtt gaa tca aca gag tat gtc aat agg cag ttc atg gca             1035
Gln Ser Glu Val Glu Ser Thr Glu Tyr Val Asn Arg Gln Phe Met Ala
    285                 290                 295 gaa aca cag ttc agc agt ggt gag aag gag caa gtg gat gag tgg aca             1083
Glu Thr Gln Phe Ser Ser Gly Glu Lys Glu Gln Val Asp Glu Trp Thr
300                 305                 310                 315 gtt gaa aca gtt gag gtt gta aac tca ctc cag cag caa cct cag gct             1131
Val Glu Thr Val Glu Val Val Asn Ser Leu Gln Gln Gln Pro Gln Ala
                320                 325                 330 gcg tcc cct tca gtc cca gag ccc cac tct ttg act cca gtg gct cag             1179
Ala Ser Pro Ser Val Pro Glu Pro His Ser Leu Thr Pro Val Ala Gln
            335                 340                 345 tca gat cca ctt gtg aga agg cag cgt gta caa gat ctt atg gca caa             1227
Ser Asp Pro Leu Val Arg Arg Gln Arg Val Gln Asp Leu Met Ala Gln
        350                 355                 360 atg caa ggg ccc tat aat ttc ata cag gat tca atg ttg gat ttt gaa             1275
Met Gln Gly Pro Tyr Asn Phe Ile Gln Asp Ser Met Leu Asp Phe Glu
    365                 370                 375 aat cag acg ctt gat cct gcc att gta tcc gca cag cct atg aac cct             1323
Asn Gln Thr Leu Asp Pro Ala Ile Val Ser Ala Gln Pro Met Asn Pro
380                 385                 390                 395 acc cag aac atg gat atg cct cag ctg gtt tgc cct cag gtt cat tct             1371
Thr Gln Asn Met Asp Met Pro Gln Leu Val Cys Pro Gln Val His Ser
                400                 405                 410 gaa tct aga ctt gcc caa tct aat caa gtt cct gta caa cca gaa gcc             1419
Glu Ser Arg Leu Ala Gln Ser Asn Gln Val Pro Val Gln Pro Glu Ala
            415                 420                 425 aca cag gtt cct ttg gtt tca tcc aca agt gag ggg tat aca gca tct             1467
```

```
             Thr Gln Val Pro Leu Val Ser Ser Thr Ser Glu Gly Tyr Thr Ala Ser
                     430                 435                 440 cag ccc ttg tac cag cca tct cat gct acg gag cag cgg ccg cag aaa      1515
Gln Pro Leu Tyr Gln Pro Ser His Ala Thr Glu Gln Arg Pro Gln Lys
    445                 450                 455 gag cca atg gat cag att cag gca aca ata tct ttg aat aca gac cag      1563
Glu Pro Met Asp Gln Ile Gln Ala Thr Ile Ser Leu Asn Thr Asp Gln
460                 465                 470                 475 act aca gca tcc tca tcc ctt cct gct gct tct cag cct caa gtg ttc      1611
Thr Thr Ala Ser Ser Ser Leu Pro Ala Ala Ser Gln Pro Gln Val Phe
                480                 485                 490 cag gct ggg aca agt aaa cct ttg cac agc agt gga atc aat gta aat      1659
Gln Ala Gly Thr Ser Lys Pro Leu His Ser Ser Gly Ile Asn Val Asn
            495                 500                 505 gca gct cca ttc cag tcc atg caa acg gtg ttc aat atg aat gct cca      1707
Ala Ala Pro Phe Gln Ser Met Gln Thr Val Phe Asn Met Asn Ala Pro
        510                 515                 520 gtc cct cct gct aat gaa cca gaa acg tta aaa caa cag agt cag tac      1755
Val Pro Pro Ala Asn Glu Pro Glu Thr Leu Lys Gln Gln Ser Gln Tyr
    525                 530                 535 cag gcc act tat aac cag agt ttt tcc agt cag cct cac caa gtg gaa      1803
Gln Ala Thr Tyr Asn Gln Ser Phe Ser Ser Gln Pro His Gln Val Glu
540                 545                 550                 555 caa aca gag ctt caa caa gac caa ctg caa acg gtg gtt ggc act tac      1851
Gln Thr Glu Leu Gln Gln Asp Gln Leu Gln Thr Val Val Gly Thr Tyr
                560                 565                 570 cat gga tcc cag gac cag cct cat caa gtg cct ggt aac cac cag caa      1899
His Gly Ser Gln Asp Gln Pro His Gln Val Pro Gly Asn His Gln Gln
            575                 580                 585 ccc cca cag cag aac act ggc ttt cca cgt agc agt cag cct tat tac      1947
Pro Pro Gln Gln Asn Thr Gly Phe Pro Arg Ser Ser Gln Pro Tyr Tyr
        590                 595                 600 aac agt cgt ggg gta tct cga gga ggg tct cgt ggt gcc aga ggc ttg      1995
Asn Ser Arg Gly Val Ser Arg Gly Gly Ser Arg Gly Ala Arg Gly Leu
    605                 610                 615 atg aat gga tac agg ggc cct gcc aat gga ttt aga gga gga tat gat      2043
Met Asn Gly Tyr Arg Gly Pro Ala Asn Gly Phe Arg Gly Gly Tyr Asp
620                 625                 630                 635 ggt tac cgc cct tca ttc tcg aac act cca aac agt ggt tat tca cag      2091
Gly Tyr Arg Pro Ser Phe Ser Asn Thr Pro Asn Ser Gly Tyr Ser Gln
                640                 645                 650 tct cag ttc act gct ccc cgg gac tac tct ggt tac cag cgg gat gga      2139
Ser Gln Phe Thr Ala Pro Arg Asp Tyr Ser Gly Tyr Gln Arg Asp Gly
            655                 660                 665 tat cag cag aat ttc aag cga ggc tct ggg cag agt gga cca cgg gga      2187
Tyr Gln Gln Asn Phe Lys Arg Gly Ser Gly Gln Ser Gly Pro Arg Gly
        670                 675                 680 gcc cca cga ggt aat ata ttg tgg tgg tga tcctagctcc tatgtggagc        2237
Ala Pro Arg Gly Asn Ile Leu Trp Trp
    685                 690 ttctgttctg gccttggaag aactgttcat agtccgcatg taggttacat gttaggaata   2297
catttatctt ttccagactt gttgctaaag attaaatgaa atgctctgtt tctaaaattt   2357
catcttgaat ccaaatttta attttgaat gactttccct gctgttgtct tcaaaatcag    2417
aacattttct ctgcctcaga aaagcgtttt tccaactgga aatttatttt tcaggtctta   2477
aaacctgcta atgttttta ggaagtacct actgaaactt tttgtaagac attttttggaa   2537 cgagcttgaa catttatata aatttattac cctctttgat ttttgaaaca tgcatattat   2597
atttaggctg agaagccctt caaatggcca gataagccac agttttagct agagaaccat   2657
```

-continued

```
ttagaattga cataactaat ctaaacttga acacttttag gaccaatgtt agtgttctaa    2717
ataccaacat atttctgatg tttaaacaga tctcccaaat tcttaggacc ttgatgtcat    2777
taaaatttag aatgacaagc ttaagaggct ttagtttcat ttgttttca agtaatgaaa     2837 aataatttct tacatgggca gatagttaat ttgttgaaca attacaggta gcatttcatg    2897
taatctgatg ttctaaatgg ttctcttatt gaaggaggtt aaagaattag gtttcttaca    2957 gttttttggct ggccatgaca tgtataaaat gtatattaag gaggaattat aaagtacttt   3017
aatttgaatg ctagtggcaa ttgatcatta agaaagtact ttaaagcaaa aggttaatgg    3077
gtcatctggg aaaaatactg aagtatcaaa ggtatttgca tgtgaatgtg ggttatgttc    3137
ttctatccca ccttgtagca tattctatga aagttgagtt aaatgatagc taaaatatct    3197
gtttcaacag catgtaaaaa gttatttaa ctgttacaag tcattataca attttgaatg     3257
ttctgtagtt tcttttaac agtttaggta caaaggtctg ttttcattct ggtgcttttt     3317
attaattttg atagtatgat gtcacttcct attgaaatgt aagctagcgt gtaccttaga    3377
atgtgagctc catgagagca ggtaccttgt ttgtcttcac tgctgtatct attcccaacg    3437
cctcatgaca gtgcctggca catagtaggc actcaataaa tacttgttga atgaatgaaa    3497
aaaaaaaaaa a                                                         3508
```

<210> SEQ ID NO 28
<211> LENGTH: 692
<212> TYPE: PRT
<213> ORGANISM: Mus musculus

<400> SEQUENCE: 28

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
                20                  25                  30

Ala Ala Pro Ala Ser Gln His Pro Ala Thr Gly Thr Gly Ala Val Gln
            35                  40                  45

Thr Glu Ala Met Lys Gln Ile Leu Gly Val Ile Asp Lys Lys Leu Arg
        50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
                100                 105                 110

Ser Phe Met Ala Leu Ser Gln Asp Ile Gln Lys Thr Ile Lys Lys Thr
            115                 120                 125

Ala Arg Arg Glu Gln Leu Met Arg Glu Glu Ala Glu Gln Lys Arg Leu
        130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Leu Ser Leu Leu Asp Glu Phe Tyr Lys Leu Val Asp
                180                 185                 190

Pro Glu Arg Asp Met Ser Leu Arg Leu Asn Glu Gln Tyr Glu His Ala
            195                 200                 205

Ser Ile His Leu Trp Asp Leu Leu Glu Gly Lys Glu Lys Pro Val Cys
        210                 215                 220
```

```
Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
            245                 250                 255

Glu Glu Glu Ala Ala Ser Ala Pro Thr Val Glu Asp Gln Val Ala Glu
        260                 265                 270

Ala Glu Pro Glu Pro Ala Glu Glu Tyr Thr Glu Gln Ser Glu Val Glu
    275                 280                 285

Ser Thr Glu Tyr Val Asn Arg Gln Phe Met Ala Glu Thr Gln Phe Ser
290                 295                 300

Ser Gly Glu Lys Glu Gln Val Asp Glu Trp Thr Val Glu Thr Val Glu
305                 310                 315                 320

Val Val Asn Ser Leu Gln Gln Pro Gln Ala Ala Ser Pro Ser Val
            325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
            405                 410                 415

Gln Ser Asn Gln Val Pro Val Gln Pro Glu Ala Thr Gln Val Pro Leu
        420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
            485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Gly Thr Tyr His Gly Ser Gln Asp
            565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
        610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
```

```
                          645                 650                 655
        Pro Arg Asp Tyr Ser Gly Tyr Gln Arg Asp Gly Tyr Gln Gln Asn Phe
                        660                 665                 670

Lys Arg Gly Ser Gly Gln Ser Gly Pro Arg Gly Ala Pro Arg Gly Asn
                        675                 680                 685

Ile Leu Trp Trp
                690

<210> SEQ ID NO 29
<211> LENGTH: 2109
<212> TYPE: DNA
<213> ORGANISM: Gallus gallus
<220> FEATURE:
<221> NAME/KEY: CDS
<222> LOCATION: (1)..(2109)
<223> OTHER INFORMATION:

<400> SEQUENCE: 29 atg ccc tcg gct acc aac ggc acc atg gcg agc agc agc ggg aag gcg      48
Met Pro Ser Ala Thr Asn Gly Thr Met Ala Ser Ser Ser Gly Lys Ala
1               5                   10                  15 ggc ccg ggc ggc aac gag cag gcc ccg gcg gcg gca gcg gcc ccg           96
Gly Pro Gly Gly Asn Glu Gln Ala Pro Ala Ala Ala Ala Ala Pro
            20                  25                  30 cag gcg tcg ggc ggc agc atc acc tcg gtt cag acc gag gcc atg aag      144
Gln Ala Ser Gly Gly Ser Ile Thr Ser Val Gln Thr Glu Ala Met Lys
        35                  40                  45 cag atc ttg gga gtg atc gac aaa aag ctc cgc aac ctc gag aag aaa      192
Gln Ile Leu Gly Val Ile Asp Lys Lys Leu Arg Asn Leu Glu Lys Lys
    50                  55                  60 aag agc aaa ctt gac gat tac cag gaa cga atg aac aag ggg gaa cgt      240
Lys Ser Lys Leu Asp Asp Tyr Gln Glu Arg Met Asn Lys Gly Glu Arg
65                  70                  75                  80 cta aat caa gat caa ctg gat gca gtg tca aaa tac cag gaa gtg aca      288
Leu Asn Gln Asp Gln Leu Asp Ala Val Ser Lys Tyr Gln Glu Val Thr
                85                  90                  95 aat aac ctg gaa ttc gct aaa gaa ctg cag agg agc ttt atg gca ctg      336
Asn Asn Leu Glu Phe Ala Lys Glu Leu Gln Arg Ser Phe Met Ala Leu
            100                 105                 110 agc caa gat atc cag aaa aca ata aaa aag acg gct cgc agg gag cag      384
Ser Gln Asp Ile Gln Lys Thr Ile Lys Lys Thr Ala Arg Arg Glu Gln
        115                 120                 125 ctg atg aga gaa gag gct gag cag aag cgt tta aag act gtg cta gag      432
Leu Met Arg Glu Glu Ala Glu Gln Lys Arg Leu Lys Thr Val Leu Glu
    130                 135                 140 ctg cag ttc att ttg gac aag ttg ggt gac gat gaa gtg cgc agt gac      480
Leu Gln Phe Ile Leu Asp Lys Leu Gly Asp Asp Glu Val Arg Ser Asp
145                 150                 155                 160 ttg aaa caa gga tca aat gga gta ccg gta ctg aca gag gag gaa ctg      528
Leu Lys Gln Gly Ser Asn Gly Val Pro Val Leu Thr Glu Glu Glu Leu
                165                 170                 175 aca atg ctg gat gaa ttt tac aag cta gtt tac cct gaa agg gac atg      576
Thr Met Leu Asp Glu Phe Tyr Lys Leu Val Tyr Pro Glu Arg Asp Met
            180                 185                 190 aac atg agg ttg aat gag cag tat gag caa gca tct gtt cac ctg tgg      624
Asn Met Arg Leu Asn Glu Gln Tyr Glu Gln Ala Ser Val His Leu Trp
        195                 200                 205 gac tta ctg gaa ggg aag gaa aaa ccc gtt tgt gga aca acc tat aaa      672
Asp Leu Leu Glu Gly Lys Glu Lys Pro Val Cys Gly Thr Thr Tyr Lys
    210                 215                 220 gcc ctg aag gag gtt gtt gaa cgt att ctt caa act agt tac ttt gat      720
Ala Leu Lys Glu Val Val Glu Arg Ile Leu Gln Thr Ser Tyr Phe Asp
```

```
Ala Leu Lys Glu Val Val Glu Arg Ile Leu Gln Thr Ser Tyr Phe Asp
225                 230                 235                 240 agc acc cat aac cat cag aac ggg tta tgt gag gaa gaa gag gca gca      768
Ser Thr His Asn His Gln Asn Gly Leu Cys Glu Glu Glu Glu Ala Ala
                245                 250                 255 ccc aca cct gca gta gaa gac act gta gca gaa gct gag cct gat cca      816
Pro Thr Pro Ala Val Glu Asp Thr Val Ala Glu Ala Glu Pro Asp Pro
                260                 265                 270 gca gaa gaa ttt act gaa cct act gaa gtt gaa tcg act gag tat gta      864
Ala Glu Glu Phe Thr Glu Pro Thr Glu Val Glu Ser Thr Glu Tyr Val
                275                 280                 285 aac aga caa ttc atg gca gag act cag ttc agc agt agt gag aag gaa      912
Asn Arg Gln Phe Met Ala Glu Thr Gln Phe Ser Ser Ser Glu Lys Glu
        290                 295                 300 cag gta gat gag tgg aca gtt gaa acg gtt gag gtt gta aat tca ctg      960
Gln Val Asp Glu Trp Thr Val Glu Thr Val Glu Val Val Asn Ser Leu
305                 310                 315                 320 cag caa caa aca caa gct aca tct cct cca gtt cct gaa cct cat aca     1008
Gln Gln Gln Thr Gln Ala Thr Ser Pro Pro Val Pro Glu Pro His Thr
                325                 330                 335 ctc act act gtg gct caa gca gat cct ctt gtt aga aga cag aga gta     1056
Leu Thr Thr Val Ala Gln Ala Asp Pro Leu Val Arg Arg Gln Arg Val
                340                 345                 350 cag gac ctt atg gcc cag atg cag ggt cca tat aac ttc atg cag gac     1104
Gln Asp Leu Met Ala Gln Met Gln Gly Pro Tyr Asn Phe Met Gln Asp
                355                 360                 365 tct atg ctg gag ttt gag aac cag aca ctt gat cct gcc att gta tct     1152
Ser Met Leu Glu Phe Glu Asn Gln Thr Leu Asp Pro Ala Ile Val Ser
370                 375                 380 gca cag ccc atg aat cca gca cag aat ttg gac atg ccg caa atg gtc     1200
Ala Gln Pro Met Asn Pro Ala Gln Asn Leu Asp Met Pro Gln Met Val
385                 390                 395                 400 tgc cct cca gtt cat act gag tca aga ctt gcc cag cct aat caa gtt     1248
Cys Pro Pro Val His Thr Glu Ser Arg Leu Ala Gln Pro Asn Gln Val
                405                 410                 415 cct gtg caa cca gaa gct acg cag gtt ccc ttg gtt tca tct aca agt     1296
Pro Val Gln Pro Glu Ala Thr Gln Val Pro Leu Val Ser Ser Thr Ser
                420                 425                 430 gag gga tat aca gcc tcc cag ccc atg tat cag cct tct cat acc aca     1344
Glu Gly Tyr Thr Ala Ser Gln Pro Met Tyr Gln Pro Ser His Thr Thr
                435                 440                 445 gag caa cgg cca cag aag gaa tcc att gac cag att cag gct tca atg     1392
Glu Gln Arg Pro Gln Lys Glu Ser Ile Asp Gln Ile Gln Ala Ser Met
        450                 455                 460 tca ctg aat gca gac cag acc ccg tca tca tca ctt ccc act gca         1440
Ser Leu Asn Ala Asp Gln Thr Pro Ser Ser Ser Leu Pro Thr Ala
465                 470                 475                 480 tcc cag ccg caa gtt ttc caa gct gga tct agc aaa cct ttg cat agc     1488
Ser Gln Pro Gln Val Phe Gln Ala Gly Ser Ser Lys Pro Leu His Ser
                485                 490                 495 agc gga atc aat gtt aat gca gct cca ttc caa tcc atg caa aca gta     1536
Ser Gly Ile Asn Val Asn Ala Ala Pro Phe Gln Ser Met Gln Thr Val
                500                 505                 510 ttc aac atg aat gca cct gtt cct cct gtt aat gag cca gaa gcc ctt     1584
Phe Asn Met Asn Ala Pro Val Pro Pro Val Asn Glu Pro Glu Ala Leu
                515                 520                 525 aag caa caa aat cag tac cag gcc agt tac aac cag agt ttc tcc aat     1632
Lys Gln Gln Asn Gln Tyr Gln Ala Ser Tyr Asn Gln Ser Phe Ser Asn
        530                 535                 540 cag cca cac caa gta gaa caa tca gat ctt cag caa gaa cag ctc cag     1680
```

-continued

```
Gln Pro His Gln Val Glu Gln Ser Asp Leu Gln Glu Gln Leu Gln
545                 550                 555                 560 aca gtt gtt ggt act tac cat ggt tct ccg gac cag acc cat caa gtg    1728
Thr Val Val Gly Thr Tyr His Gly Ser Pro Asp Gln Thr His Gln Val
                565                 570                 575 gca gga aac cac cag caa cct ccc cag cag aat act gga ttt cca cgc    1776
Ala Gly Asn His Gln Gln Pro Pro Gln Gln Asn Thr Gly Phe Pro Arg
            580                 585                 590 aac agt cag cct tat tac aac agt cgg gga gtg tct cgt ggt gga tca    1824
Asn Ser Gln Pro Tyr Tyr Asn Ser Arg Gly Val Ser Arg Gly Gly Ser
        595                 600                 605 cgt ggg act cgt gga ttg atg aat ggt tac agg gga cct gca aat gga    1872
Arg Gly Thr Arg Gly Leu Met Asn Gly Tyr Arg Gly Pro Ala Asn Gly
    610                 615                 620 ttt aga gga gga tat gat ggc tac cgt cct tca ttt tcc aac act ccg    1920
Phe Arg Gly Gly Tyr Asp Gly Tyr Arg Pro Ser Phe Ser Asn Thr Pro
625                 630                 635                 640 aac agt ggt tac acg cag ccc caa ttt aat gct cct cga gat tat tca    1968
Asn Ser Gly Tyr Thr Gln Pro Gln Phe Asn Ala Pro Arg Asp Tyr Ser
                645                 650                 655 aac tac cag cgg gat gga tat cag cag aac ttc aaa cgt ggt tct gga    2016
Asn Tyr Gln Arg Asp Gly Tyr Gln Gln Asn Phe Lys Arg Gly Ser Gly
            660                 665                 670 caa agt ggg cct cgg gga gct cct cga ggt cgt gga ggg ccc cca aga    2064
Gln Ser Gly Pro Arg Gly Ala Pro Arg Gly Arg Gly Gly Pro Pro Arg
        675                 680                 685 cca aac aga ggg atg cct caa atg aac gct cag caa gtg aat taa       2109
Pro Asn Arg Gly Met Pro Gln Met Asn Ala Gln Gln Val Asn
    690                 695                 700

<210> SEQ ID NO 30
<211> LENGTH: 702
<212> TYPE: PRT
<213> ORGANISM: Gallus gallus

<400> SEQUENCE: 30

Met Pro Ser Ala Thr Asn Gly Thr Met Ala Ser Ser Ser Gly Lys Ala
1               5                   10                  15

Gly Pro Gly Gly Asn Glu Gln Ala Pro Ala Ala Ala Ala Ala Ala Pro
                20                  25                  30

Gln Ala Ser Gly Gly Ser Ile Thr Ser Val Gln Thr Glu Ala Met Lys
            35                  40                  45

Gln Ile Leu Gly Val Ile Asp Lys Lys Leu Arg Asn Leu Glu Lys Lys
        50                  55                  60

Lys Ser Lys Leu Asp Asp Tyr Gln Glu Arg Met Asn Lys Gly Glu Arg
65                  70                  75                  80

Leu Asn Gln Asp Gln Leu Asp Ala Val Ser Lys Tyr Gln Glu Val Thr
                85                  90                  95

Asn Asn Leu Glu Phe Ala Lys Glu Leu Gln Arg Ser Phe Met Ala Leu
            100                 105                 110

Ser Gln Asp Ile Gln Lys Thr Ile Lys Lys Thr Ala Arg Arg Glu Gln
        115                 120                 125

Leu Met Arg Glu Glu Ala Glu Gln Lys Arg Leu Lys Thr Val Leu Glu
    130                 135                 140

Leu Gln Phe Ile Leu Asp Lys Leu Gly Asp Asp Glu Val Arg Ser Asp
145                 150                 155                 160

Leu Lys Gln Gly Ser Asn Gly Val Pro Val Leu Thr Glu Glu Leu
                165                 170                 175
```

-continued

```
Thr Met Leu Asp Glu Phe Tyr Lys Leu Val Tyr Pro Glu Arg Asp Met
            180                 185                 190

Asn Met Arg Leu Asn Glu Gln Tyr Glu Gln Ala Ser Val His Leu Trp
        195                 200                 205

Asp Leu Leu Glu Gly Lys Glu Lys Pro Val Cys Gly Thr Thr Tyr Lys
    210                 215                 220

Ala Leu Lys Glu Val Glu Arg Ile Leu Gln Thr Ser Tyr Phe Asp
225                 230                 235                 240

Ser Thr His Asn His Gln Asn Gly Leu Cys Glu Glu Glu Ala Ala
                245                 250                 255

Pro Thr Pro Ala Val Glu Asp Thr Val Ala Glu Ala Glu Pro Asp Pro
            260                 265                 270

Ala Glu Glu Phe Thr Glu Pro Thr Glu Val Glu Ser Thr Glu Tyr Val
        275                 280                 285

Asn Arg Gln Phe Met Ala Glu Thr Gln Phe Ser Ser Glu Lys Glu
    290                 295                 300

Gln Val Asp Glu Trp Thr Val Glu Thr Val Glu Val Val Asn Ser Leu
305                 310                 315                 320

Gln Gln Gln Thr Gln Ala Thr Ser Pro Pro Val Pro Glu Pro His Thr
                325                 330                 335

Leu Thr Thr Val Ala Gln Ala Asp Pro Leu Val Arg Arg Gln Arg Val
            340                 345                 350

Gln Asp Leu Met Ala Gln Met Gln Gly Pro Tyr Asn Phe Met Gln Asp
        355                 360                 365

Ser Met Leu Glu Phe Glu Asn Gln Thr Leu Asp Pro Ala Ile Val Ser
    370                 375                 380

Ala Gln Pro Met Asn Pro Ala Gln Asn Leu Asp Met Pro Gln Met Val
385                 390                 395                 400

Cys Pro Pro Val His Thr Glu Ser Arg Leu Ala Gln Pro Asn Gln Val
                405                 410                 415

Pro Val Gln Pro Glu Ala Thr Gln Val Pro Leu Val Ser Ser Thr Ser
            420                 425                 430

Glu Gly Tyr Thr Ala Ser Gln Pro Met Tyr Gln Pro Ser His Thr Thr
        435                 440                 445

Glu Gln Arg Pro Gln Lys Glu Ser Ile Asp Gln Ile Gln Ala Ser Met
    450                 455                 460

Ser Leu Asn Ala Asp Gln Thr Pro Ser Ser Ser Leu Pro Thr Ala
465                 470                 475                 480

Ser Gln Pro Gln Val Phe Gln Ala Gly Ser Ser Lys Pro Leu His Ser
                485                 490                 495

Ser Gly Ile Asn Val Asn Ala Ala Pro Phe Gln Ser Met Gln Thr Val
            500                 505                 510

Phe Asn Met Asn Ala Pro Val Pro Val Asn Glu Pro Glu Ala Leu
        515                 520                 525

Lys Gln Gln Asn Gln Tyr Gln Ala Ser Tyr Asn Gln Ser Phe Ser Asn
    530                 535                 540

Gln Pro His Gln Val Glu Gln Ser Asp Leu Gln Gln Glu Gln Leu Gln
545                 550                 555                 560

Thr Val Val Gly Thr Tyr His Gly Ser Pro Asp Gln Thr His Gln Val
                565                 570                 575

Ala Gly Asn His Gln Gln Pro Gln Gln Asn Thr Gly Phe Pro Arg
            580                 585                 590

Asn Ser Gln Pro Tyr Tyr Asn Ser Arg Gly Val Ser Arg Gly Gly Ser
        595                 600                 605
```

-continued

```
Arg Gly Thr Arg Gly Leu Met Asn Gly Tyr Arg Gly Pro Ala Asn Gly
    610                 615                 620

Phe Arg Gly Gly Tyr Asp Gly Tyr Arg Pro Ser Phe Ser Asn Thr Pro
625                 630                 635                 640

Asn Ser Gly Tyr Thr Gln Pro Gln Phe Asn Ala Pro Arg Asp Tyr Ser
                645                 650                 655

Asn Tyr Gln Arg Asp Gly Tyr Gln Gln Asn Phe Lys Arg Gly Ser Gly
            660                 665                 670

Gln Ser Gly Pro Arg Gly Ala Pro Arg Gly Arg Gly Pro Pro Arg
        675                 680                 685

Pro Asn Arg Gly Met Pro Gln Met Asn Ala Gln Gln Val Asn
    690                 695                 700

<210> SEQ ID NO 31
<211> LENGTH: 20
<212> TYPE: DNA
<213> ORGANISM: Artificial
<220> FEATURE:
<223> OTHER INFORMATION: T3 primer

<400> SEQUENCE: 31
aattaaccct cactaaaggg                                              20

<210> SEQ ID NO 32
<211> LENGTH: 19
<212> TYPE: DNA
<213> ORGANISM: Artificial
<220> FEATURE:
<223> OTHER INFORMATION: T7 primer

<400> SEQUENCE: 32
taatacgact cactatagg                                               19

<210> SEQ ID NO 33
<211> LENGTH: 18
<212> TYPE: DNA
<213> ORGANISM: Artificial
<220> FEATURE:
<223> OTHER INFORMATION: primer

<400> SEQUENCE: 33
aaggtttgaa tggagtgc                                                18

<210> SEQ ID NO 34
<211> LENGTH: 18
<212> TYPE: DNA
<213> ORGANISM: Artificial
<220> FEATURE:
<223> OTHER INFORMATION: primer

<400> SEQUENCE: 34
tgctcctttt caccactg                                                18

<210> SEQ ID NO 35
<211> LENGTH: 18
<212> TYPE: DNA
<213> ORGANISM: Artificial
<220> FEATURE:
<223> OTHER INFORMATION: GAPDH primer

<400> SEQUENCE: 35
gggctgcttt taactctg                                                18
```

```
<210> SEQ ID NO 36
<211> LENGTH: 18
<212> TYPE: DNA
<213> ORGANISM: Artificial
<220> FEATURE:
<223> OTHER INFORMATION: GAPDH primer

<400> SEQUENCE: 36
ccaggaaatg agcttgac                                                 18

<210> SEQ ID NO 37
<211> LENGTH: 27
<212> TYPE: DNA
<213> ORGANISM: Artificial
<220> FEATURE:
<223> OTHER INFORMATION: primer

<400> SEQUENCE: 37
catatggcat taagtcaaga tattcag                                       27

<210> SEQ ID NO 38
<211> LENGTH: 23
<212> TYPE: DNA
<213> ORGANISM: Artificial
<220> FEATURE:
<223> OTHER INFORMATION: primer

<400> SEQUENCE: 38
ggtacctttg cggcatccct ctg                                           23

<210> SEQ ID NO 39
<211> LENGTH: 21
<212> TYPE: DNA
<213> ORGANISM: Artificial
<220> FEATURE:
<223> OTHER INFORMATION: primer

<400> SEQUENCE: 39
catatgccgt cggccaccag c                                             21

<210> SEQ ID NO 40
<211> LENGTH: 22
<212> TYPE: DNA
<213> ORGANISM: Artificial
<220> FEATURE:
<223> OTHER INFORMATION: primer

<400> SEQUENCE: 40
ggtaccattc acttgctgag tg                                            22

<210> SEQ ID NO 41
<211> LENGTH: 23
<212> TYPE: DNA
<213> ORGANISM: Artificial
<220> FEATURE:
<223> OTHER INFORMATION: primer

<400> SEQUENCE: 41
gagctcatgc cctcggccac cag                                           23

<210> SEQ ID NO 42
<211> LENGTH: 23
<212> TYPE: DNA
<213> ORGANISM: Artificial
<220> FEATURE:
<223> OTHER INFORMATION: primer

<400> SEQUENCE: 42
```
ctcgagttaa ttcacttgct gag                                    23

<210> SEQ ID NO 43
<211> LENGTH: 10
<212> TYPE: PRT
<213> ORGANISM: Homo sapiens

<400> SEQUENCE: 43

Ala Val Gln Thr Glu Ala Met Lys Gln Ile
1               5                   10

<210> SEQ ID NO 44
<211> LENGTH: 9
<212> TYPE: PRT
<213> ORGANISM: Homo sapiens

<400> SEQUENCE: 44

Val Gln Thr Glu Ala Met Lys Gln Ile
1               5

<210> SEQ ID NO 45
<211> LENGTH: 10
<212> TYPE: PRT
<213> ORGANISM: Homo sapiens

<400> SEQUENCE: 45

Thr Glu Ala Met Lys Gln Ile Leu Gly Val
1               5                   10

<210> SEQ ID NO 46
<211> LENGTH: 10
<212> TYPE: PRT
<213> ORGANISM: Homo sapiens

<400> SEQUENCE: 46

Gln Ile Leu Gly Val Ile Asp Lys Lys Leu
1               5                   10

<210> SEQ ID NO 47
<211> LENGTH: 10
<212> TYPE: PRT
<213> ORGANISM: Homo sapiens

<400> SEQUENCE: 47

Arg Leu Asn Gln Asp Gln Leu Asp Ala Val
1               5                   10

<210> SEQ ID NO 48
<211> LENGTH: 9
<212> TYPE: PRT
<213> ORGANISM: Homo sapiens

<400> SEQUENCE: 48

Leu Asn Gln Asp Gln Leu Asp Ala Val
1               5

<210> SEQ ID NO 49
<211> LENGTH: 9
<212> TYPE: PRT
<213> ORGANISM: Homo sapiens

<400> SEQUENCE: 49

Lys Glu Leu Gln Arg Ser Phe Met Ala
1               5

<210> SEQ ID NO 50
<211> LENGTH: 10
<212> TYPE: PRT
<213> ORGANISM: Homo sapiens

<400> SEQUENCE: 50

Met Ala Leu Ser Gln Asp Ile Gln Lys Thr
1               5                   10

<210> SEQ ID NO 51
<211> LENGTH: 9
<212> TYPE: PRT
<213> ORGANISM: Homo sapiens

<400> SEQUENCE: 51

Ala Glu Gln Lys Arg Leu Lys Thr Val
1               5

<210> SEQ ID NO 52
<211> LENGTH: 10
<212> TYPE: PRT
<213> ORGANISM: Homo sapiens

<400> SEQUENCE: 52

Val Leu Asp Lys Leu Gly Asp Asp Glu Val
1               5                   10

<210> SEQ ID NO 53
<211> LENGTH: 9
<212> TYPE: PRT
<213> ORGANISM: Homo sapiens

<400> SEQUENCE: 53

Lys Leu Gly Asp Asp Glu Val Arg Thr
1               5

<210> SEQ ID NO 54
<211> LENGTH: 9
<212> TYPE: PRT
<213> ORGANISM: Homo sapiens

<400> SEQUENCE: 54

Lys Leu Val Asp Pro Glu Arg Asp Met
1               5

<210> SEQ ID NO 55
<211> LENGTH: 10
<212> TYPE: PRT
<213> ORGANISM: Homo sapiens

<400> SEQUENCE: 55

Leu Val Asp Pro Glu Arg Asp Met Ser Leu
1               5                   10

<210> SEQ ID NO 56
<211> LENGTH: 10
<212> TYPE: PRT
<213> ORGANISM: Homo sapiens

<400> SEQUENCE: 56

Glu Gln Tyr Glu His Ala Ser Ile His Leu
1               5                   10

<210> SEQ ID NO 57
<211> LENGTH: 9

```
<212> TYPE: PRT
<213> ORGANISM: Homo sapiens

<400> SEQUENCE: 57

Ser Glu Val Glu Ser Thr Glu Tyr Val
1               5

<210> SEQ ID NO 58
<211> LENGTH: 9
<212> TYPE: PRT
<213> ORGANISM: Homo sapiens

<400> SEQUENCE: 58

Thr Glu Tyr Val Asn Arg Gln Phe Met
1               5

<210> SEQ ID NO 59
<211> LENGTH: 9
<212> TYPE: PRT
<213> ORGANISM: Homo sapiens

<400> SEQUENCE: 59

Phe Met Ala Glu Thr Gln Phe Thr Ser
1               5

<210> SEQ ID NO 60
<211> LENGTH: 9
<212> TYPE: PRT
<213> ORGANISM: Homo sapiens

<400> SEQUENCE: 60

Lys Glu Gln Val Asp Glu Trp Thr Val
1               5

<210> SEQ ID NO 61
<211> LENGTH: 10
<212> TYPE: PRT
<213> ORGANISM: Homo sapiens

<400> SEQUENCE: 61

Gln Val Asp Glu Trp Thr Val Glu Thr Val
1               5                   10

<210> SEQ ID NO 62
<211> LENGTH: 9
<212> TYPE: PRT
<213> ORGANISM: Homo sapiens

<400> SEQUENCE: 62

Trp Thr Val Glu Thr Val Glu Val Val
1               5

<210> SEQ ID NO 63
<211> LENGTH: 9
<212> TYPE: PRT
<213> ORGANISM: Homo sapiens

<400> SEQUENCE: 63

Ser Leu Gln Gln Gln Pro Gln Ala Ala
1               5

<210> SEQ ID NO 64
<211> LENGTH: 10
<212> TYPE: PRT
<213> ORGANISM: Homo sapiens
```

```
<400> SEQUENCE: 64

Gln Gln Pro Gln Ala Ala Ser Pro Ser Val
1               5                   10

<210> SEQ ID NO 65
<211> LENGTH: 9
<212> TYPE: PRT
<213> ORGANISM: Homo sapiens

<400> SEQUENCE: 65

Asn Gln Thr Leu Asp Pro Ala Ile Val
1               5

<210> SEQ ID NO 66
<211> LENGTH: 10
<212> TYPE: PRT
<213> ORGANISM: Homo sapiens

<400> SEQUENCE: 66

Gln Thr Leu Asp Pro Ala Ile Val Ser Ala
1               5                   10

<210> SEQ ID NO 67
<211> LENGTH: 9
<212> TYPE: PRT
<213> ORGANISM: Homo sapiens

<400> SEQUENCE: 67

Thr Leu Asp Pro Ala Ile Val Ser Ala
1               5

<210> SEQ ID NO 68
<211> LENGTH: 10
<212> TYPE: PRT
<213> ORGANISM: Homo sapiens

<400> SEQUENCE: 68

Ala Ala Pro Phe Gln Ser Met Gln Thr Val
1               5                   10

<210> SEQ ID NO 69
<211> LENGTH: 10
<212> TYPE: PRT
<213> ORGANISM: Homo sapiens

<400> SEQUENCE: 69

Phe Asn Met Asn Ala Pro Val Pro Pro Val
1               5                   10

<210> SEQ ID NO 70
<211> LENGTH: 9
<212> TYPE: PRT
<213> ORGANISM: Homo sapiens

<400> SEQUENCE: 70

Asn Met Asn Ala Pro Val Pro Pro Val
1               5

<210> SEQ ID NO 71
<211> LENGTH: 10
<212> TYPE: PRT
<213> ORGANISM: Homo sapiens

<400> SEQUENCE: 71

Gln Ser Phe Ser Ser Gln Pro His Gln Val
```

```
1               5                   10
```

<210> SEQ ID NO 72
<211> LENGTH: 9
<212> TYPE: PRT
<213> ORGANISM: Homo sapiens

<400> SEQUENCE: 72

```
Gln Tyr Glu His Ala Ser Ile His Leu
1               5
```

<210> SEQ ID NO 73
<211> LENGTH: 10
<212> TYPE: PRT
<213> ORGANISM: Homo sapiens

<400> SEQUENCE: 73

```
Gln Tyr Glu His Ala Ser Ile His Leu Trp
1               5                   10
```

<210> SEQ ID NO 74
<211> LENGTH: 10
<212> TYPE: PRT
<213> ORGANISM: Homo sapiens

<400> SEQUENCE: 74

```
Glu Tyr Thr Glu Gln Ser Glu Val Glu Ser
1               5                   10
```

<210> SEQ ID NO 75
<211> LENGTH: 9
<212> TYPE: PRT
<213> ORGANISM: Homo sapiens

<400> SEQUENCE: 75

```
Glu Thr Val Glu Val Val Asn Ser Leu
1               5
```

<210> SEQ ID NO 76
<211> LENGTH: 10
<212> TYPE: PRT
<213> ORGANISM: Homo sapiens

<400> SEQUENCE: 76

```
Gln Tyr Gln Ala Ser Tyr Asn Gln Ser Phe
1               5                   10
```

<210> SEQ ID NO 77
<211> LENGTH: 10
<212> TYPE: PRT
<213> ORGANISM: Homo sapiens

<400> SEQUENCE: 77

```
Arg Ser Tyr Ser Cys Gln Val Met His Glu
1               5                   10
```

<210> SEQ ID NO 78
<211> LENGTH: 109
<212> TYPE: PRT
<213> ORGANISM: Mus musculus

<400> SEQUENCE: 78

```
Pro Arg Ala Ser Leu Gly Val Ser Glu Thr Leu Leu Cys Thr Ser Gly
1               5                   10                  15

Phe Thr Phe Thr Asp Tyr Tyr Met Ser Trp Val Arg Gln Pro Pro Gly
```

-continued

```
                 20                  25                  30
Lys Ala Leu Glu Trp Leu Gly Phe Ile Arg Asn Lys Ala Asn Gly Tyr
            35                  40                  45

Thr Thr Glu Tyr Ser Ala Ser Val Lys Gly Arg Phe Thr Ile Ser Arg
 50                  55                  60

Asp Asn Ser Gln Ser Ile Leu Tyr Leu Gln Met Asn Thr Leu Arg Ala
65                   70                  75                  80

Glu Asp Ser Ala Thr Tyr Tyr Cys Ala Arg Ala Asn Trp Ala Phe Asp
                85                  90                  95

Tyr Trp Gly Gln Gly Thr Thr Val Thr Val Ser Ser Lys
            100                 105

<210> SEQ ID NO 79
<211> LENGTH: 94
<212> TYPE: PRT
<213> ORGANISM: Mus musculus

<400> SEQUENCE: 79

Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
    50                  55                  60

Glu Thr Glu Asp Phe Gly Met Tyr Phe Cys Gln Gln Ser Asn Ser Trp
65                  70                  75                  80

Pro Tyr Thr Phe Gly Gly Gly Thr Lys Leu Glu Ile Lys Gln
            85                  90

<210> SEQ ID NO 80
<211> LENGTH: 24
<212> TYPE: DNA
<213> ORGANISM: Artificial
<220> FEATURE:
<223> OTHER INFORMATION: primer

<400> SEQUENCE: 80
atgccctcgg ccaccagcca cagc                                            24

<210> SEQ ID NO 81
<211> LENGTH: 24
<212> TYPE: DNA
<213> ORGANISM: Artificial
<220> FEATURE:
<223> OTHER INFORMATION: primer

<400> SEQUENCE: 81
ttaattcact tgctgagtgt tcat                                            24
```